United States Patent
Stokes et al.

(10) Patent No.: US 8,187,176 B2
(45) Date of Patent: May 29, 2012

(54) DEVICE FOR INSUFFLATING THE INTERIOR OF A GASTRIC CAVITY OF A PATIENT

(75) Inventors: Michael J. Stokes, Cincinnati, OH (US); Jason L. Harris, Mason, OH (US); Mark S. Zeiner, Mason, OH (US); Lawrence Crainich, Charlestown, NH (US); Daniel E Alesi, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 998 days.

(21) Appl. No.: 12/113,823

(22) Filed: May 1, 2008

(65) Prior Publication Data
US 2009/0023984 A1   Jan. 22, 2009

Related U.S. Application Data

(63) Continuation-in-part of application No. 11/779,325, filed on Jul. 18, 2007, now abandoned.

(51) Int. Cl.
*A61B 1/12* (2006.01)
(52) U.S. Cl. .................. 600/157; 600/151; 600/156
(58) Field of Classification Search .................. 600/156, 600/104, 116, 151, 157; 604/28, 500
See application file for complete search history.

(56) References Cited

U.S. PATENT DOCUMENTS

| | | | |
|---|---|---|---|
| 2004/0082859 A1 | 4/2004 | Schaer | |
| 2006/0265042 A1 | 11/2006 | Catanese | |
| 2007/0073320 A1 | 3/2007 | Mikkaichi | |
| 2007/0112362 A1 | 5/2007 | Mikkaichi | |
| 2007/0135831 A1* | 6/2007 | Burnett | 606/192 |
| 2007/0142846 A1 | 6/2007 | Catanese | |
| 2007/0244359 A1 | 10/2007 | Cabiri et al. | |
| 2008/0140099 A1* | 6/2008 | Ghabrial et al. | 606/157 |

FOREIGN PATENT DOCUMENTS

| | | |
|---|---|---|
| EP | 1884199 | 2/2008 |
| WO | WO 2005/058239 | 6/2005 |
| WO | WO 2007/037335 | 4/2007 |
| WO | WO 2008/156796 | 12/2008 |

OTHER PUBLICATIONS

P. Reissman et al., Colonoscopic-assisted laparoscopic colectomy Apr. 29, 1994, Surg Endosc 8: 1352-1353.*
PCT International Search Report and Written Opinion, Jun. 26, 2009 (15 pgs.).

* cited by examiner

*Primary Examiner* — Jackie Ho
*Assistant Examiner* — Imani Hayman
(74) *Attorney, Agent, or Firm* — Welsh Flaxman & Gitler LLC

(57) ABSTRACT

A method for laparoscopically preventing insufflation of the small bowel during gastric procedures includes applying an obstruction member at the pyloric sphincter to block the passage of gas from the gastric cavity into the small bowel and insufflating the gastric cavity.

6 Claims, 50 Drawing Sheets

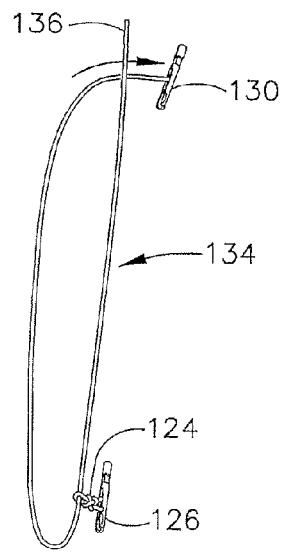
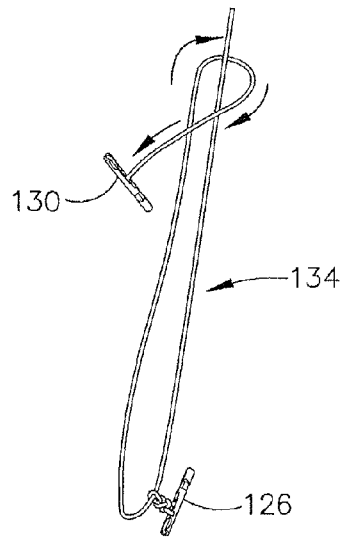
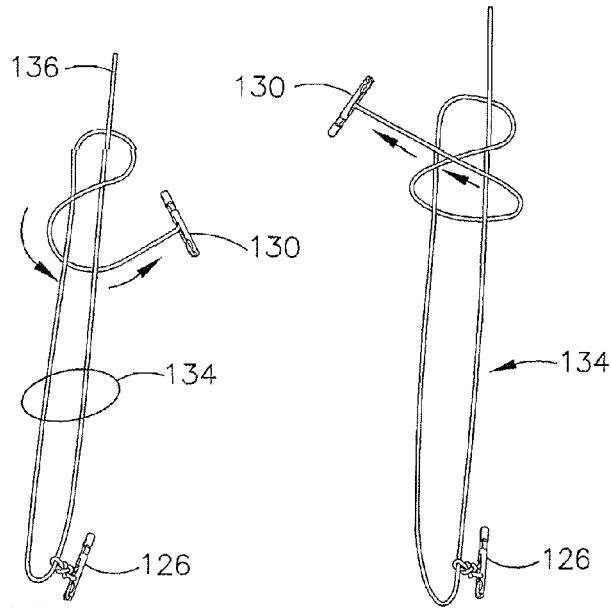
FIG. 12a    FIG. 12b    FIG. 12c    FIG. 12d    FIG. 12e

DEVICE FOR INSUFFLATING THE INTERIOR OF A GASTRIC CAVITY OF A PATIENT

CROSS REFERENCE TO RELATED APPLICATIONS

This application is a continuation-in-part of U.S. patent application Ser. No. 11/779,325, filed Jul. 18, 2007 now abandoned, entitled "A DEVICE FOR INSUFFLATING THE INTERIOR OF A GASTRIC CAVITY OF A PATIENT".

BACKGROUND OF THE INVENTION

1. Field of the Invention

The present invention relates generally to gastric reduction. More particularly, the invention relates to a method and apparatus for laparoscopically preventing the insufflation of the small bowel.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resected portion of the small intestine. This resected portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It also is known to create plications in the gastric cavity for the purpose of reducing the volume of the gastric cavity. While a purely transoral endoscopic approach is desirable from the point of view of minimizing trauma inflicted by the creation of surgical openings as required in laparoscopic procedures, operating solely within the interior of the gastric cavity limits the plication depth that can be achieved without cutting. Furthermore, access and visibility within the gastric and peritoneal cavities is limited in a purely endoscopic procedure as the extent of the reduction increases.

These endoscopic procedures require that gas be injected into a lumen for visibility. During normal upper gastrointestinal testing, the stomach is insufflated so that the entire stomach may be visible with the endoscopic image. This insufflation gas passes into the jejunum through the pylorus, sphincter and insufflates the small bowel. For upper endoscopies, this does not pose a problem.

However, the peritoneal cavity is occluded when the small bowel is inflated. Since hybrid procedures (endoscopic with laparoscopic imaging) require that the medical practitioner have adequate visibility with both the endoscopic and laparoscopic instruments the insufflation of the small bowel during these procedures is undesirable.

With the foregoing in mind, it is desirable to have a surgical weight loss procedure that is inexpensive, with few potential complications, and that provides patients with a weight loss benefit while buying time for the lifestyle changes necessary to maintain the weight loss. Further, it is desirable that the procedure be minimally invasive to the patient, allowing for a quick recovery and less scarring.

As such, and with the problems associated with insufflation particularly in mind, a procedure and apparatus which allow for proper visualization are needed. The present invention provides such a procedure and apparatus

SUMMARY OF THE INVENTION

It is, therefore, an object of the present invention to provide a method for laparoscopically preventing insufflation of the small bowel during gastric procedures. The method includes applying an obstruction member at the pyloric sphincter to block the passage of gas from the gastric cavity into the small bowel and insufflating the gastric cavity.

It is also an object of the present invention to provide a method including the step of inserting a tube into and through the pyloric sphincter to vent or suction any gas that passes into the small bowel.

It is another object of the present invention to provide a method wherein the tube is inserted laparoscopically.

It is a further object of the present invention to provide a method wherein the obstruction member is a fluid injected into the pyloric sphincter.

It is also an object of the present invention to provide a method wherein the fluid is an absorbable material.

It is another object of the present invention to provide a method wherein the obstruction member is a fold formed in tissue of the pyloric sphincter.

It is a further object of the present invention to provide a method wherein the obstruction member is an external clamp for compression of the pyloric sphincter.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 12a-12e show a method of tying the slip knot between the T-tag anchors.

FIG. 16 is an isometric view of a plurality of the buttressing devices of. FIG. 15 interconnected together.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
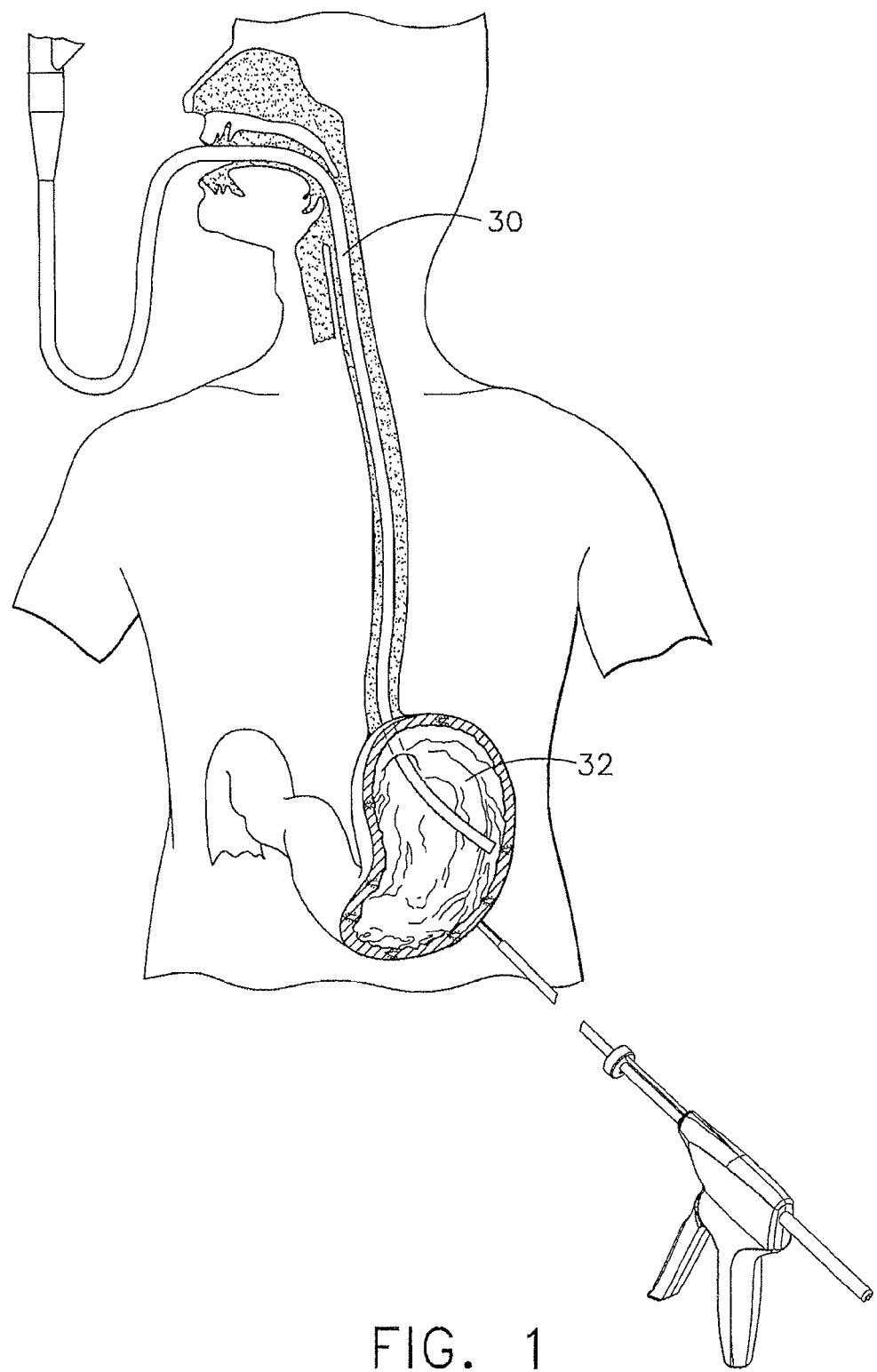
FIG. 1 is a schematic view of a patient during a hybrid endoscopic-laparoscopic procedure.

Referring now to the figures, in which like numerals indicate like elements throughout the views, FIG. 1 is a diagrammatic view of a patient during a hybrid endoscopic-laparoscopic procedure. As used in the present specification, the term endoscopic is intended to refer to medical procedures in which the body is accessed through a natural orifice (for example, transorally) and the term laparoscopic is intended to refer to medical procedures wherein a surgically created open (for example, as created with a trocar) is employed in accessing the body. In the method of the present invention, serosa-to-serosa folds are formed in the anterior wall of the gastric cavity through a hybrid laparoscopic-endoscopic approach. In the hybrid approach, visualization of the one or more serosa-to-serosa fold locations can be achieved by passing an endoscope into the interior of the gastric cavity. As shown in FIG. 1, a flexible endoscope 30 can be passed transesophageally into the gastric cavity 32. The endoscope 30 provides insufflation, illumination, and visualization of the gastric cavity 32, as well as a passageway into the gastric cavity 32. The gastric cavity 32 is insufflated through the endoscope 30 to create a sufficiently rigid working surface that may be pierced without damaging the opposing wall of the gastric cavity 32. Insufflation of the gastric cavity 32 also allows the boundaries of the gastric cavity 32 and the desired location for a serosa-to-serosa fold to be mapped out by external palpation of the abdomen. The pressure on the abdominal wall 42 is observed within the gastric cavity 32 through the endoscope 30 and may aid in determining the appropriate placement of one or more trocars, or other type of port allowing abdominal, laparoscopic access. Using the endoscope 30 to visualize the plication locations may reduce or eliminate the need for visualization on the outside of the gastric cavity 32.

Figure 2:
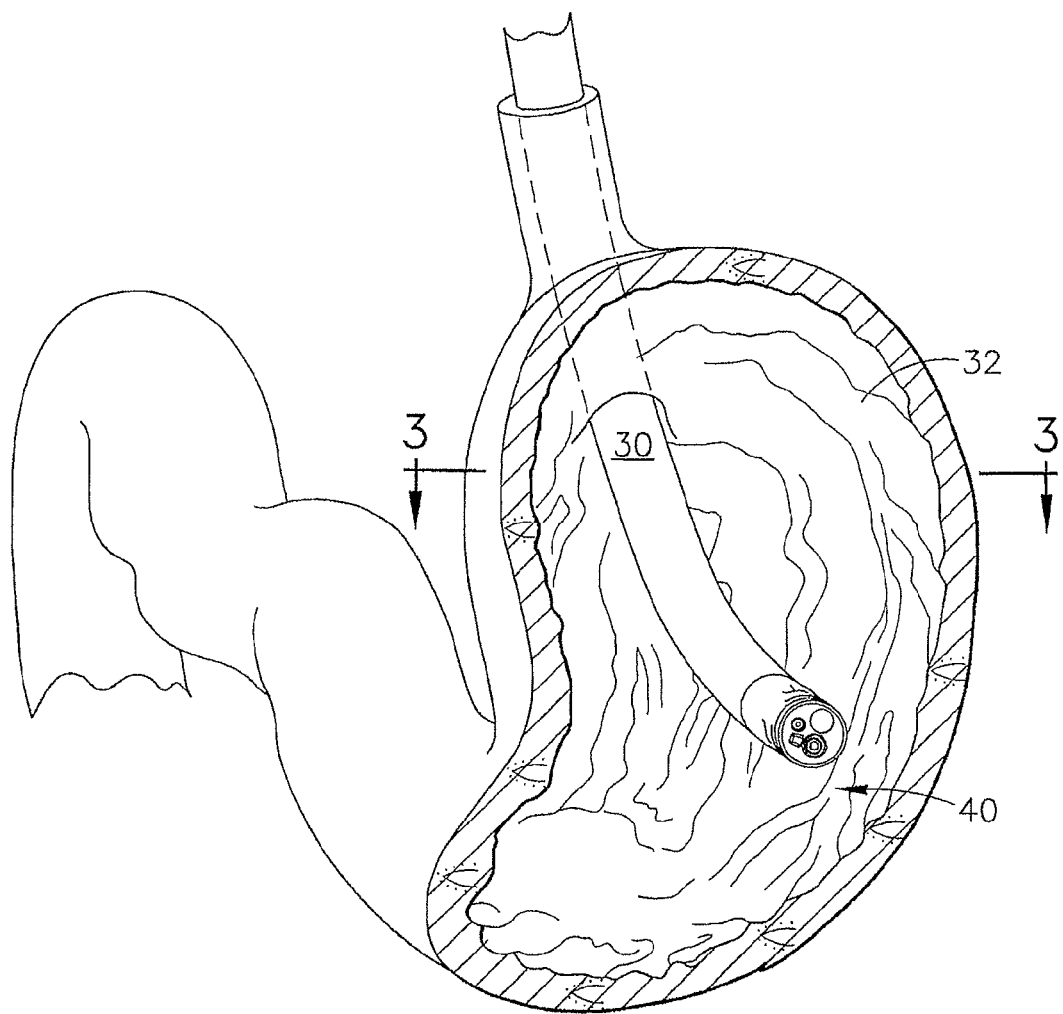
FIG. 2 is a diagrammatic, exterior view of a gastric cavity, partially broken way to show an endoscope positioned against the interior surface of the anterior cavity wall.
Figure 3:
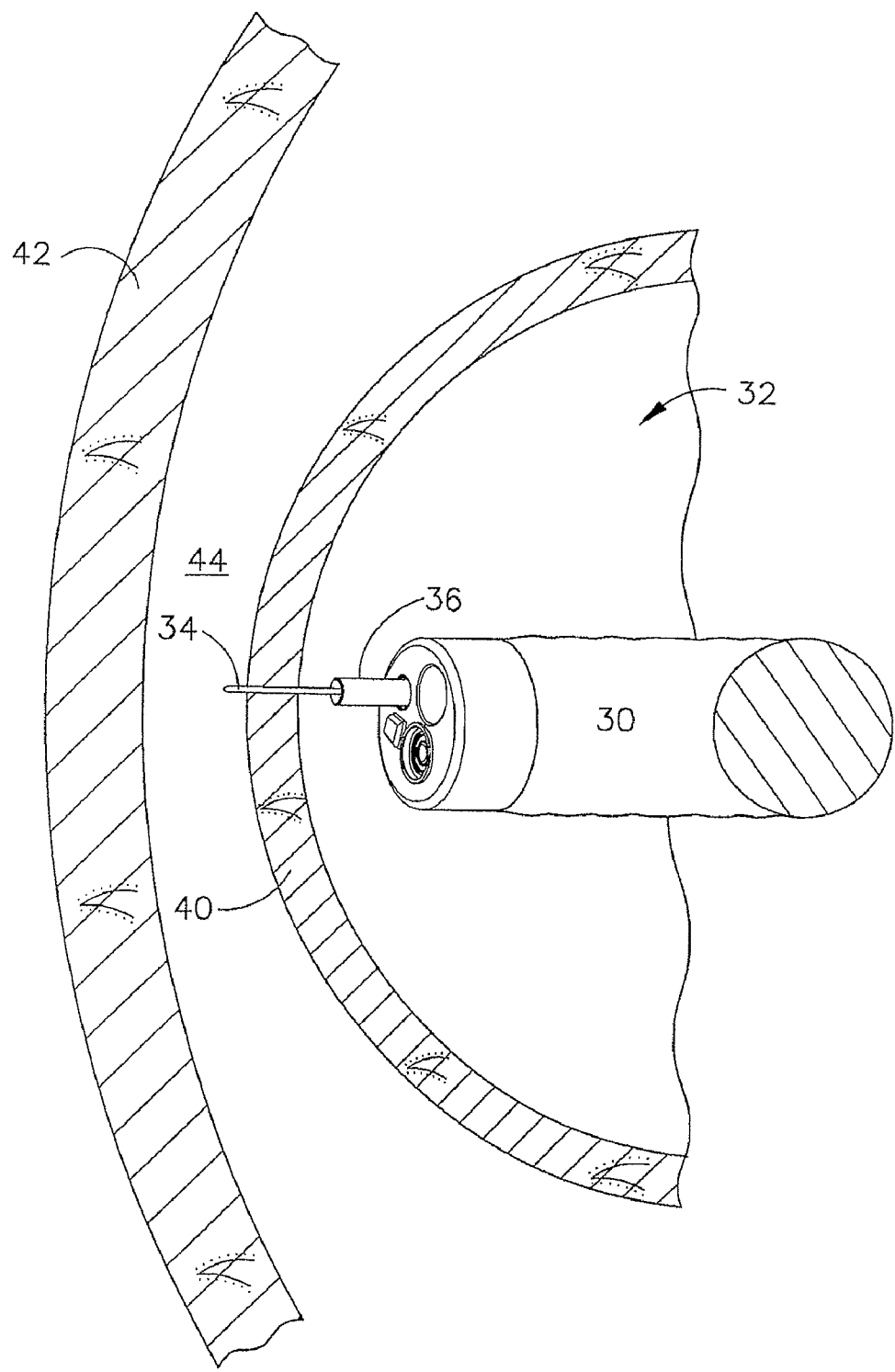
FIG. 3 is a cross-sectional view of an abdominal wall and gastric cavity showing a needle inserted through the gastric cavity wall into the peritoneal cavity.

Eliminating the need to visualize the outside of the gastric cavity 32 also reduces or eliminates the need to insufflate the abdominal cavity. However, where deemed necessary, the abdominal cavity may be insufflated prior to placement of a trocar to expand the working area inside the gastric cavity 32. Typically, the abdominal cavity is insufflated using a Veress needle that is inserted at the umbilicus or left upper quadrant of the gastric cavity 32 in order to introduce carbon dioxide ($CO_2$) into the gastric cavity 32. Although common practices involve using a Veress needle to create additional working space in the abdominal cavity for safer trocar insertion, it introduces a small risk of organ perforation or infection due to the lack of guidance in inserting the needle. An alternative method to potentially reduce this risk involves transorally insufflating the abdomen by inserting a shielded needle into the working channel of the endoscope 30 prior to passage of the endoscope 30 into the gastric cavity 32. Inside the gastric cavity 32, the endoscope 30 is pointed towards the distal anterior surface of the gastric cavity 32, as shown in FIG. 2. The needle 34 is extended out the distal end of the endoscope 30, and a protective shield 36 is withdrawn from the needle tip, so that the needle 34 can be inserted through the anterior cavity wall 40, as shown in FIG. 3. The needle 34 is inserted to a position between the anterior cavity wall 40 of the gastric cavity 32 and the abdominal wall 42. The distal anterior surface of the gastric cavity 32 is a desirable area to puncture with the needle 34 due to the absence of critical organs in this area. With the needle 34 outside of the anterior cavity wall 40 of the gastric cavity 32, a suitable abdominal insufflation gas such as $CO_2$ is pumped through the needle 34 and into the peritoneal cavity 44 to provide an area within the gastric cavity 32 to insert the trocar.

Figure 4:
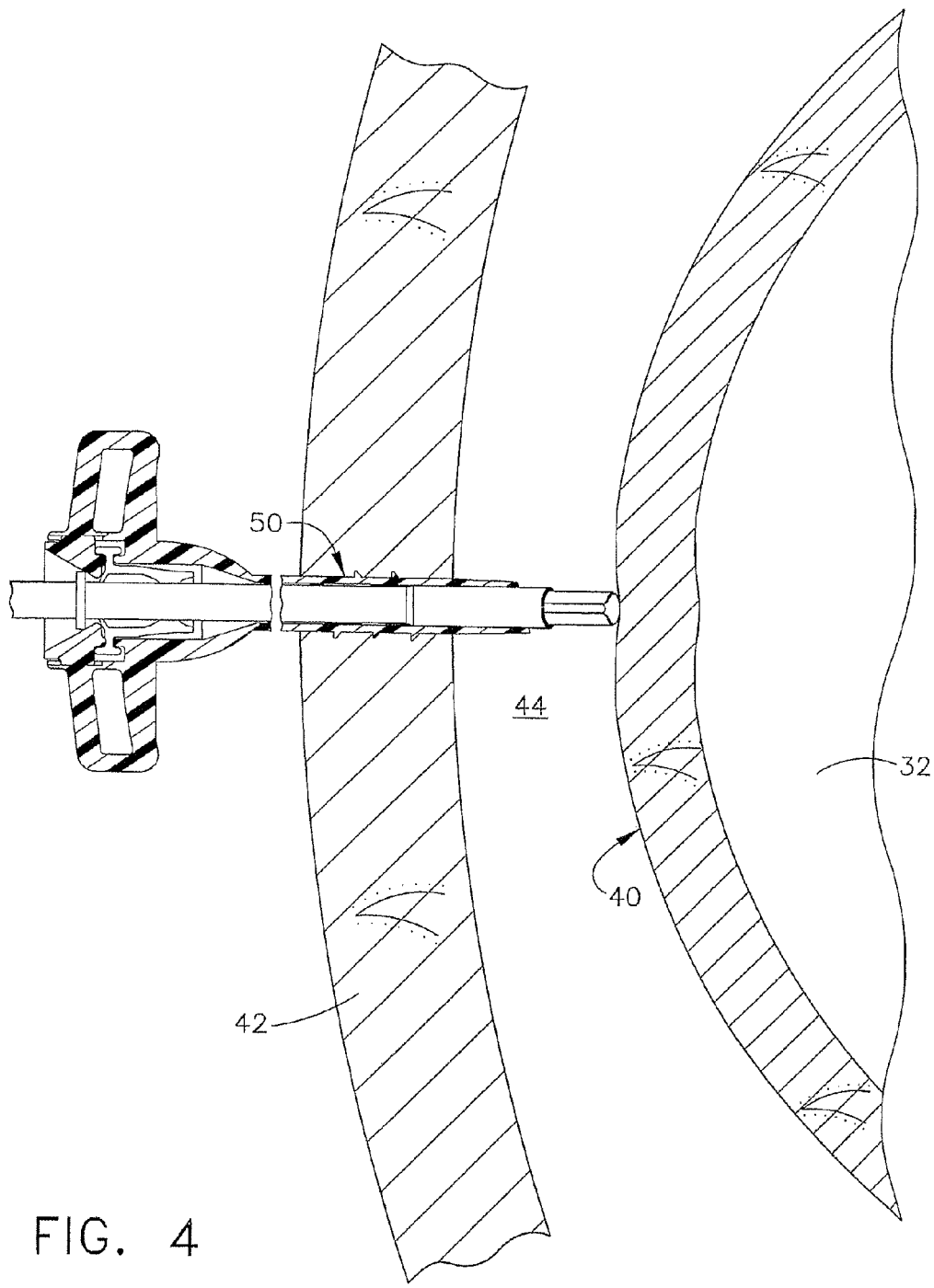
FIG. 4 is a cross-sectional view of an abdominal wall and gastric cavity showing a laparoscopic device probing tissue within the peritoneal cavity.

After the gastric cavity 32 has been mapped through the endoscope 30, and the abdominal cavity insufflated if necessary, a trocar is inserted into the abdominal wall 42 to provide access to the peritoneal cavity. FIG. 4 shows a trocar 50 inserted through an incision in the abdominal wall 42. The trocar 50 is inserted directly above the gastric cavity 32. The trocar placement can also be in the same zones as would be utilized for RYGB or gastric banding. The placement of the trocar 50 will depend upon the intended location of the serosa-to-serosa fold. The trocar 50 preferably has a small diameter to allow an adequate passageway for instruments while minimizing the size of the incision. Trocars with diameters in the range of approximately 3-5 mm provide suitable access to the gastric cavity 32. Percutaneous approaches with device diameters less than approximately 3-5 mm remain a possibility however, with the size of the hole defined by the diameter of the suture anchor (if penetrating anchors are used) or the diameter of the piercing needle. With the trocar 50 inserted into abdominal wall 42, a suture anchor deployment device 52 is passed through the trocar and into the peritoneal cavity 44 to facilitate and secure a serosa-to-serosa fold.

Alternative trocar placements may of course be used at the preference of the practitioner. As one skilled in the art will recognize, three 5 mm trocars readily allow the simultaneous use of a laparoscopic camera, tissue manipulation instrument (grasper, etc.) and tissue approximation and fixation device (suture anchor deployment device, etc.). When needed a fourth 5 mm incision may be used for liver retraction. Standard laparoscopic techniques often require higher abdominal insufflation pressures to provide adequate laparoscopic visualization and ease to freely manipulate laparoscopic instrumentation. Higher abdominal insufflation pressures may require the procedure to be performed under general anesthesia. Conscious sedation procedures require lower sustained abdominal insufflation pressures. One method to avoid general anesthesia, or maintain conscious sedation as a viable option is to sustain low abdominal insufflation pressures and temporarily increase pressures for short periods only when needed.

As natural orifice procedures and the tools that enable them become more commonplace, procedures requiring fewer skin incisions will become more prevalent. One natural orifice method to accomplish external cavity wall folding includes passing a flexible endoscope or colonoscope into the colon, creating a colotomy, and guiding the endoscope to a hollow body organ such as the stomach. Once in position, a T-tag anchor, or other tissue anchor, delivery system delivers multiple anchor sets in the desired pattern into or through the cavity wall. Cinching, tying, or otherwise securely apposing anchor sets can create tissue folds having the desired effect.

There are multiple minimally invasive methods available to permit the desired folding procedure including the hybrid endoscopic and laparoscopic procedures discussed. Percutaneous access approaches may also be used to further reduce incision sizes. Ultimately, natural orifice procedures (involving transgastric, transcolonic, transvaginal, etc) will be performed eliminating skin incisions. However, one skilled in the art will readily acknowledge that there are a multitude of surgical approaches to gain access to the peritoneal cavity involving one or more abdominal incisions. A completely feasible option remains performing this procedure in an open surgical setting.

FIGS. 5, 6A, 6B, 7 and 8 illustrates an exemplary suture anchor deployment device 52 for use during a cavity wall folding procedure. The exemplary device shown and described below deploys multiple T-tag type suture anchors for facilitating a tissue fold. However, T-tag anchors are only one of numerous types of tissue fasteners that can be utilized for forming a cavity wall fold. Various other tissue fasteners which are suitable for apposing and securing tissue such as, for example, simple suture knots and laparoscopically deployable suture anchors, may also be utilized without departing from the scope of the invention. As one skilled in the art will recognize, examples of fasteners suitable for this task include but are not limited to the T-type anchors (mentioned above and described in more detail below), reconfigurable "basket"-type anchors (which generally comprise a number of configurable struts or legs extending between two collars or support members), and linear anchors (elongate anchors which are configured to fold or become compressed into a bowed or expanded configuration). In general, anchor characteristics are such that prior to deployment they can easily be placed into or through tissue(s), but after deployment, have an altered configuration providing at least one dimension sufficiently large to maintain the anchor in place.

Figure 5:
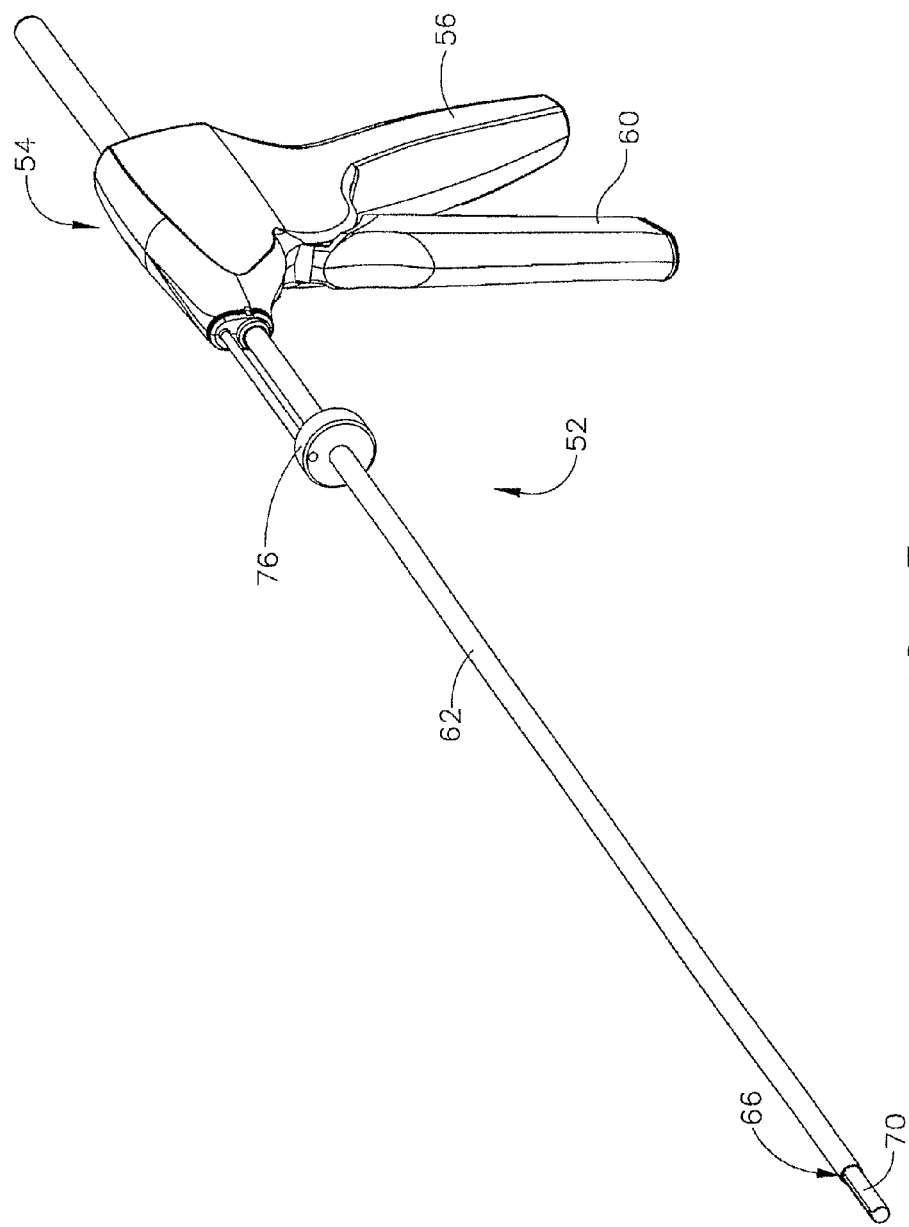
FIG. 5 is an isometric view of an exemplary suture anchor deployment device.

Referring to FIG. 5, the exemplary suture anchor deployment device 52 includes a handle 54 having a pistol grip 56 and a movable trigger 60. An elongated, tubular deployment device housing 62 extends distally from handle 54. The deployment device housing 62 has sufficient length (on the order of 18") to enable use within an obese patient at numerous trocar access sites. Likewise, the deployment device housing 62 is sized to allow for passage through a small (3-5 mm) diameter trocar.

Figure 6A:
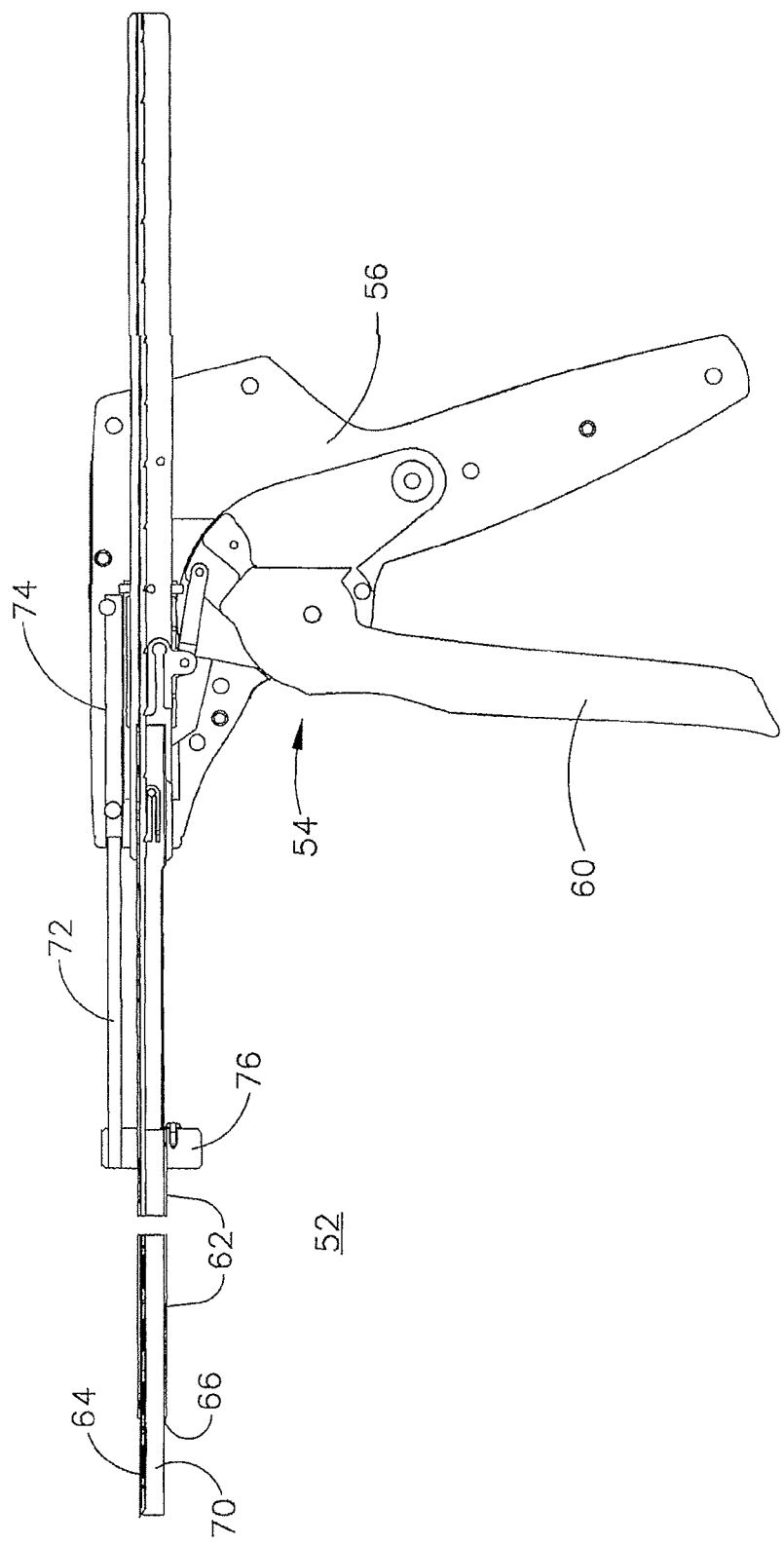
FIGS. 6a and 6b are side cross-sectional views of the suture anchor deployment device shown in FIG. 5.
Figure 6B:
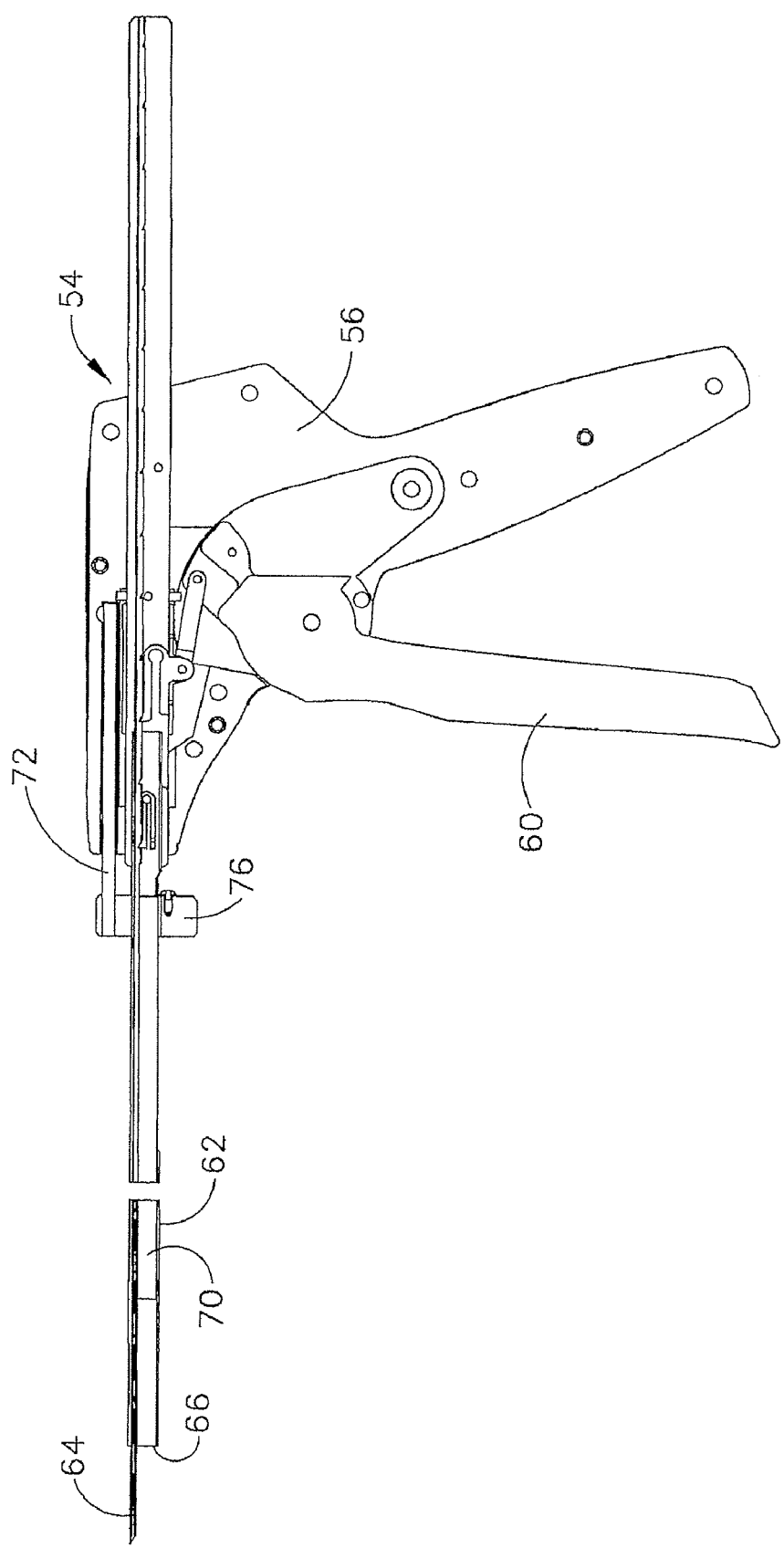
Figure 21A:
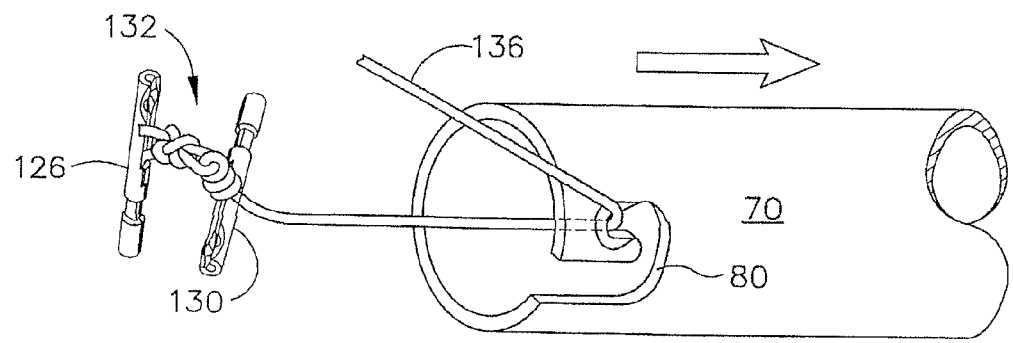
FIGS. 21a and 21b show detailed, perspective views of two separate distal cutting edges of the protective sheath, shown severing a suture.
Figure 21B:
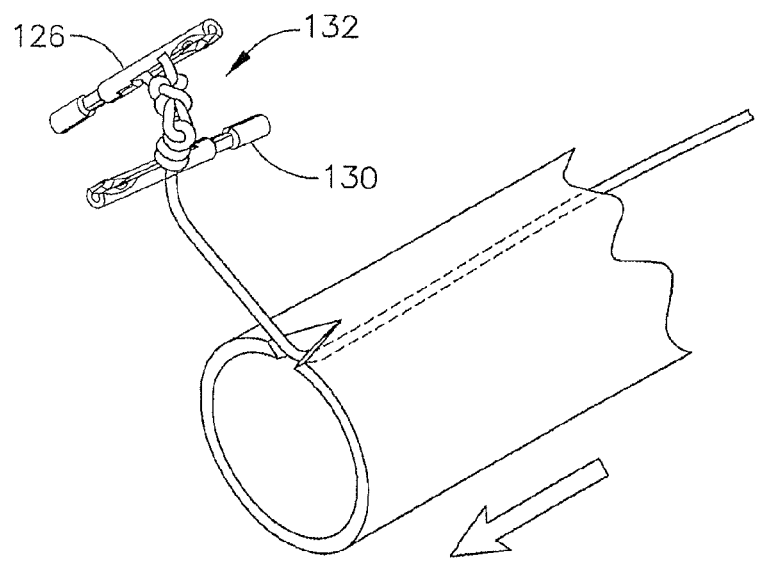

As shown in FIG. 6A, a needle 64 extends distally within the lumen of deployment device housing 62 from the handle 54 through the open distal housing tip 66. A retractable, protective sheath 70 extends distally through the deployment device housing 62 and over the exposed tip of needle 64. A rod 72 is attached to protective sheath 70 by a ring 76 that extends about the circumference of the deployment device housing 62. To retract the sheath, the ring 76 is pulled proximally, causing the rod 72 to slide along a track 74 in the handle 54. As the rod 72 slides along the track 74, the attached protective sheath 70 is drawn in a proximal direction away from the tip of the needle 64. The rod 72 bottoms out within the track 74 when the protective sheath 70 is in a fully retracted position, as shown in FIG. 6B. The rod 72 is bent slightly so that the rod 72 must be manually manipulated to slide it through the track 74 (see FIG. 6B). This slight bend in the rod 72 prevents the rod 72 from unintentionally retracting into the track 74 and leaving the tip of the needle 64 exposed. Numerous methods to protect the needle and to shield the needle from accidental sticks may be employed as those skilled in the art will recognize. The suture anchor deployment device 52 preferably includes a cutting edge for severing a suture following T-tag anchor deployment. In the device shown in FIGS. 5-7, the cutting edge is a hook shaped cutout 80 formed into the distal end of the protective sheath 70. The suture extending through the deployment device housing 62 can be drawn into the stem of the cutout 80 and trapped and severed at the hook tip. The cutting may be accomplished by shaping the stem of the hook shaped cutout 80 so that it necks down in a sharp 'V' shape, so that when the suture anchor deployment device 52 pulls the suture into the 'V', it is cut (FIG. 21A). Alternatively, with the suture seated in the stem, a separate sheath may be translated (linear or rotational translation) shearing in a scissors fashion the suture within the stem. Yet another variant is to have a 'V' shaped slit at the distal end of the protective sheath 70 with the open end of the 'V' located distal on the device (FIG. 21B). By simply advancing the device so that the suture is forced into the 'V', the suture may be cut. Numerous other methods involving slicing, shearing, and heating the suture causing it to separate may be employed.

The needle 64 includes a slotted lumen that extends proximally from the sharpened tip through the deployment device housing 62 for retaining T-tag anchors. The needle 64 can retain and deploy from one to twenty (or more depending on anchor length) T-tag anchors, with the particular number of T-tag anchors loaded into the needle 64 dependent upon the selected deployment scheme. Multiple T-tag anchors (that is, a stack of T-tag anchors), indicated by reference numeral 82, can be stacked one against another within the lumen of the needle 64. The T-tag anchors are stacked such that the suture 84 from each T-tag anchor (see FIG. 8), exits the T-tag anchor in the midsection, perpendicular to the axis of the T-tag anchor. The T-tag anchors and needle slot 86 are aligned so that the suture 84 from the T-tag anchors passes through the needle slot 86.

Figure 7:
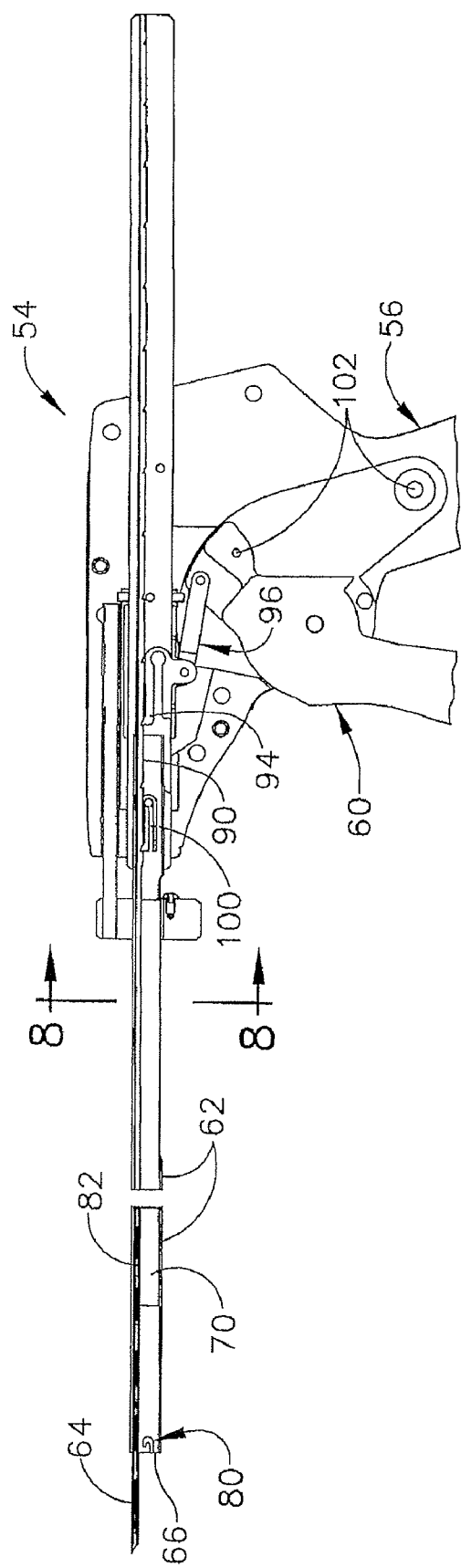
FIG. 7 is a more detailed, cross-sectional view of the suture anchor deployment device of FIG. 5.
Figure 8:
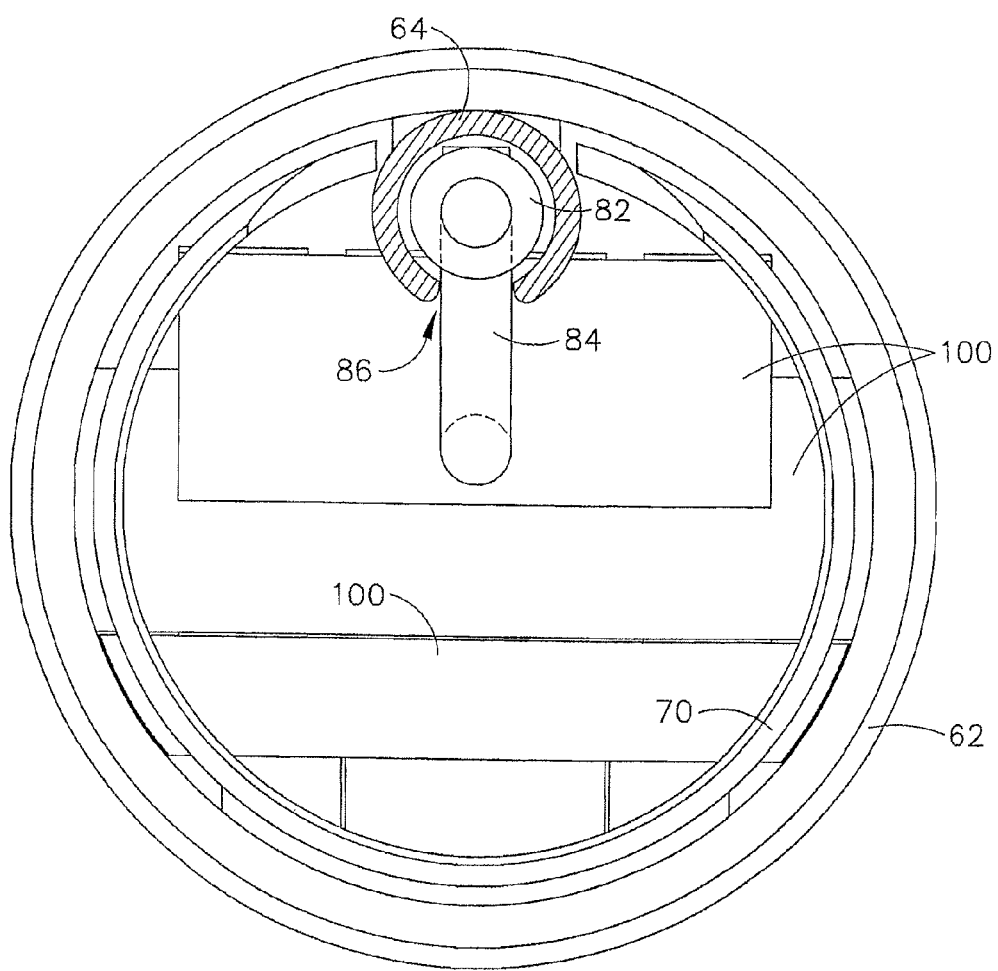
FIG. 8 is a cross-sectional view taken along line 8-8 of FIG. 7, showing the needle shaft and handle portions of the suture anchor deployment device.

As shown in FIG. 7, the suture anchor deployment device 52 includes an actuating mechanism for expelling T-tag anchors. The actuating mechanism includes a pushrod 90 at the proximal end of the T-tag anchor stack 82 for advancing and expelling the T-tag anchors from the needle 64. The pushrod 90 includes a plurality of notches which engage a drive pawl 94 for advancing the pushrod 90 distally. A drive pawl 94 is in turn connected through a link 96 to the trigger 60. As the trigger 60 is pivoted towards the pistol grip 56, the pushrod 90 is advanced distally (through the link and drive pawl) against the proximal most T-tag anchor in the T-tag anchor stack 82. The contact force of the pushrod 90 propels the T-tag anchor stack 82 towards the open distal end of the needle 64. For each squeeze of the trigger 60, a single T-tag anchor is expelled through the distal tip of the needle 64 and into the adjacent tissue as the T-tag anchor stack 82 is advanced distally the length of one T-tag anchor. As a T-tag anchor is released, the attached suture exits the suture anchor deployment device 52 through the needle slot 86. An anti backup pawl 100 in the handle 54 prevents the push rod 90 from moving proximally when the trigger 60 is released. An extension spring (not shown) extends between the connection points 102 on the handle 54 and the trigger 60 to provide the necessary force to return the trigger 60, drive pawl 94 and link 96 to their initial positions when the manual pressure on the trigger 60 is released. The suture anchor deployment device 52 disclosed herein in accordance with a preferred embodiment includes the capability to store and deliver multiple T-tag anchors during a procedure. Preferably, the suture anchor deployment device 52 can be reloaded with additional T-tag anchors when the initial stack is depleted, so that the suture anchor deployment device 52 may be reused as necessary during the procedure.

Figure 9:
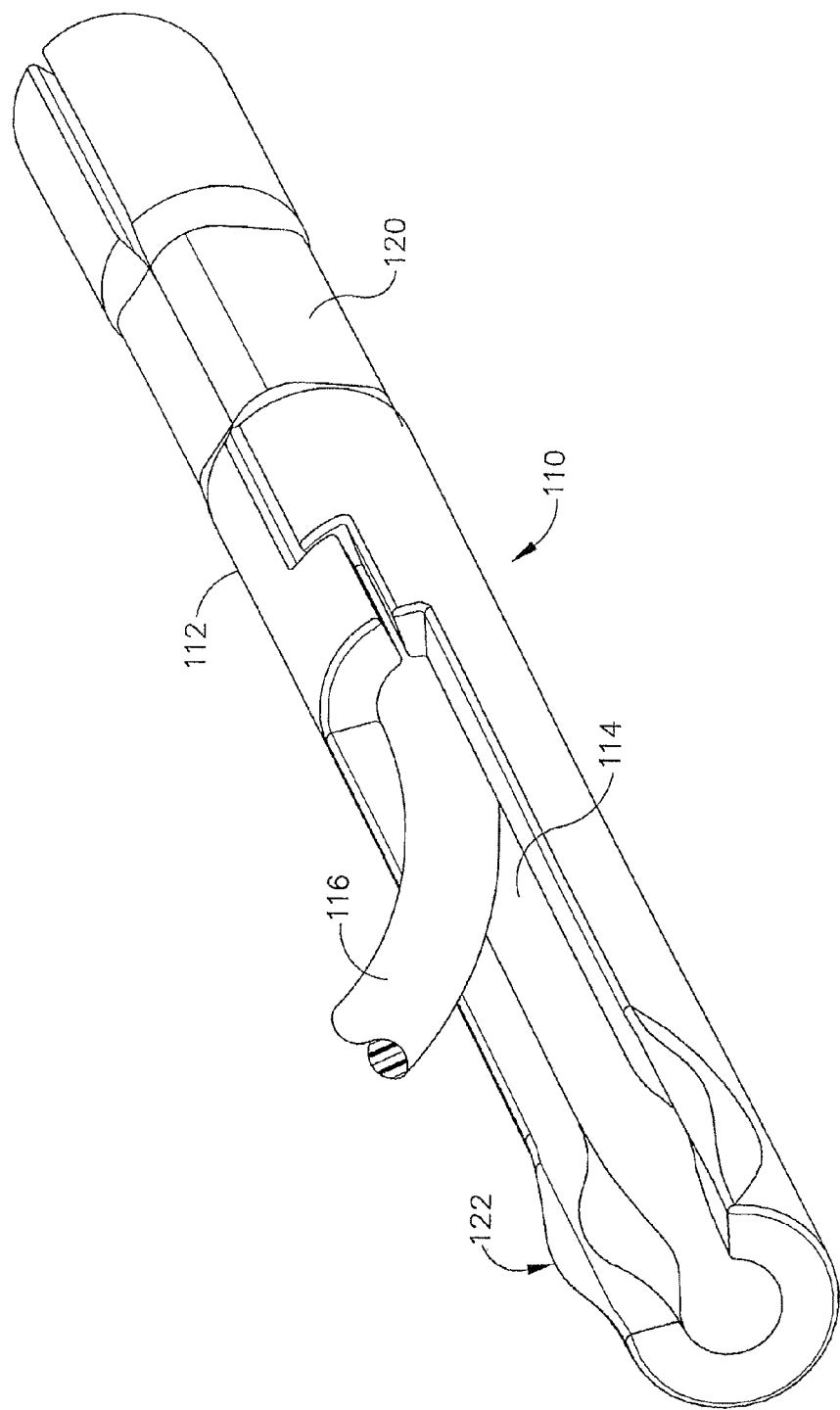
FIG. 9 is an isometric view of an exemplary T-tag anchoring device.

FIG. 9 shows a first exemplary T-tag anchor 110 for deployment from the suture anchor deployment device 52. As shown in the Figure, the T-tag anchor 110 comprises an elongated tube 112 having an opening or slot 114 extending approximately one-half the length of the tube 112. The remaining length of the tube 112 is closed into a cylindrical shape. One end of a length of flexible material, such as suture 116, is inserted into the closed length of the tube 112. The end is retained within the tube 112 by crimping the midsection of the cylindrical length, as indicated by 120. The remaining portion of suture 116 protrudes freely out the slot 114. The T-tag anchor 110 may be formed in this manner from flat sheet stock that is curled into a small diameter tube. A gap may be left in the sheet stock to form a slot 114 when the sheet is curled. The T-tag anchor 110 can also be formed from alternative materials such as, for example, injection molded plastics; or can be manufactured as a solid cylindrical tube with a hole drilled or otherwise formed through the midsection for the suture to protrude through. As shown in FIG. 9, an outwardly extending projection or bulge 122 is preferably formed along the length of T-tag anchor 110. The bulge 122 creates friction between the inner diameter of the needle 64 and the T-tag anchor 110 when the T-tag anchor 110 is held within the suture anchor deployment device. This friction between the needle and T-tag anchor prevents the T-tag anchor from being unintentionally released from the suture anchor deployment device. Alternatively, friction between the needle and a single T-tag anchor may be applied by reducing the needle inner diameter at a distal location so that only the most distal T-tag anchor is in contact with the high friction area. When loaded into the needle 64, the T-tag anchor 110 is positioned so that the slot 114 extends adjacent to the needle slot 86, so that the free end of the suture 116 passes from the T-tag anchor 110 through the needle slot 86. Additional alternative embodiments of the T-tag anchor 110 are described in further detail in commonly owned and pending U.S. patent application Ser. No. 11/274,352, filed on Nov. 15, 2005, U.S. patent application Ser. No. 11/274,358, filed on Nov. 15, 2005, and U.S. patent application Ser. No. 11/437,441, filed on May 19, 2006; each of which is hereby incorporated herein by reference in its entirety. Further embodiments of T-tag anchor 110 are described in U.S. Application Publication No. 2006/0025819, the contents of which is hereby incorporated herein by reference in its entirety.

Figure 10:
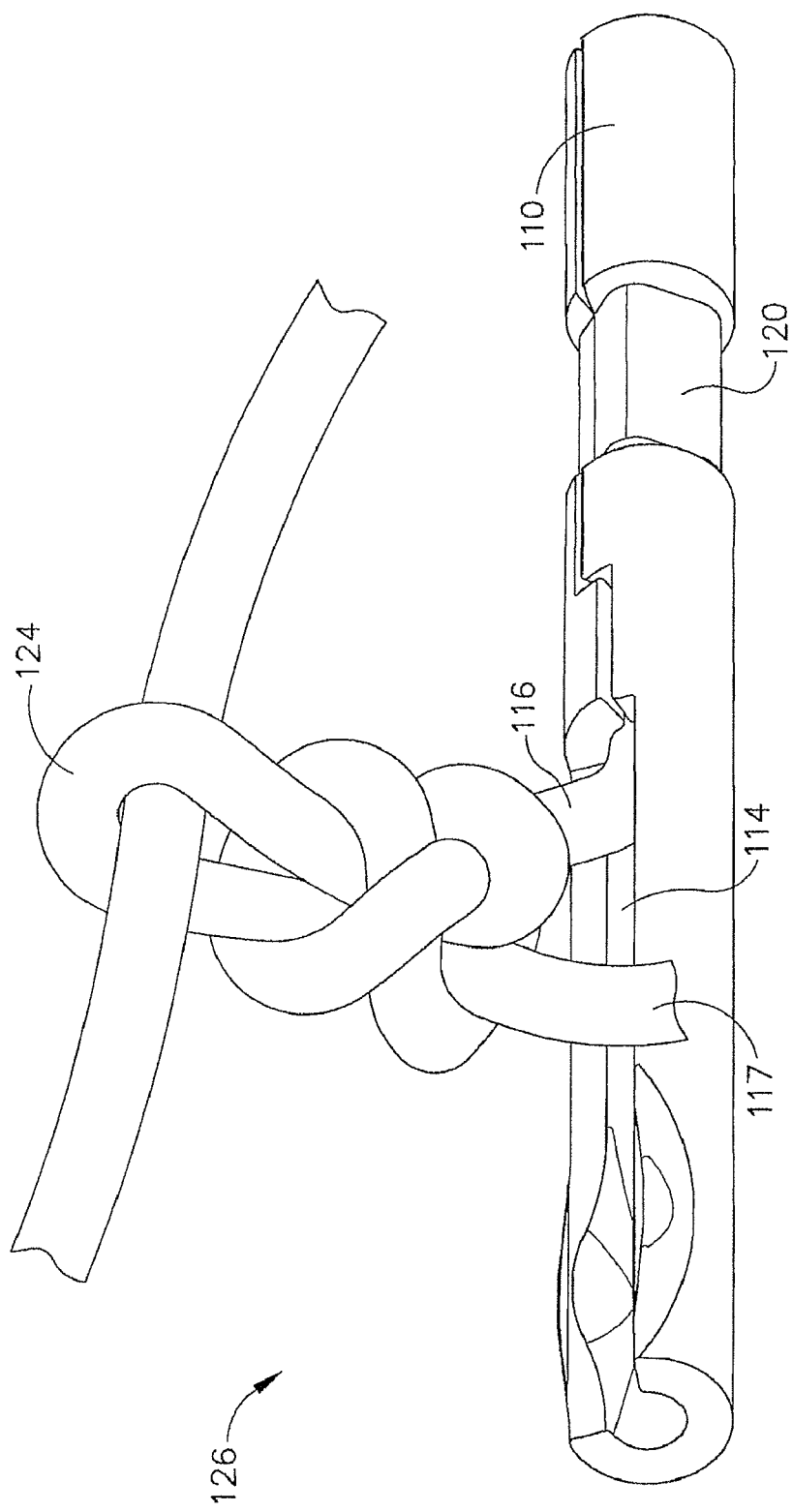
FIG. 10 is a side view of the T-tag anchoring device of FIG. 9, showing a first method for forming a suture loop.
Figure 13:
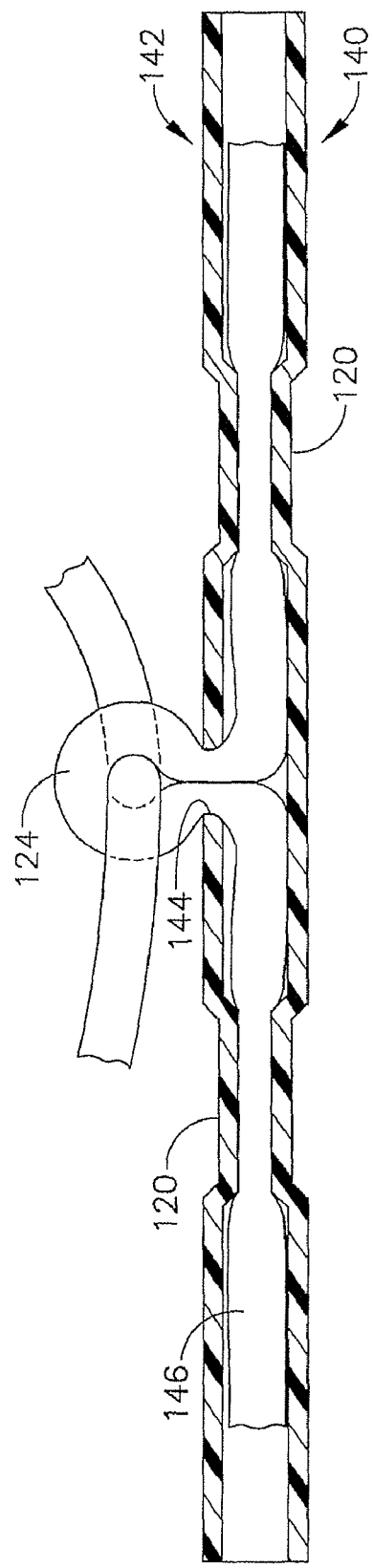
FIG. 13 is a side view of a second exemplary T-tag anchoring device, showing a second method for forming a suture loop.

In a first preferred embodiment for forming a tissue plication, a pair of T-tag anchors is pre-tied together prior to loading the tags into the suture anchor deployment device. To tie the T-tag anchors together, a suture loop or other slidable connecting member 124, such as shown in FIG. 10, is formed in the suture of a first T-tag anchor. One skilled in the art will clearly recognize that suture loop 124 may be formed by a variety of different types of knots, such as, for example, a square knot, one or more half hitch knots, or a hangman's knot. Alternatively, the suture loop 124 can be formed by drawing the suture through an opening 144 in a T Tag anchor, such as shown in FIG. 13. In this second loop embodiment, a short length of suture 146 extends within an anchor tube 142, and is crimped within the tube at opposite ends, as indicated by 120. Between the crimped ends, the suture is pulled through opening 144 to form suture loop 124.

In an alternative embodiment, an opening can be formed through a first T-tag anchor so that the T-tag anchor itself serves as the slidable member, thereby eliminating the need for a suture loop. In this embodiment, the suture from the second T-tag anchor is passed through the opening in the first T-tag anchor to allow the first anchor to slide relative to the second anchor along the length of the suture.

The second T-tag anchor of the pair is attached at the end of a length of suture. To connect the anchor pair, the suture from the second T-tag anchor is passed through the suture loop 124 of the first T-tag anchor to allow the first T-tag anchor to slide relative to the second T-tag anchor along the length of the suture. After the first T-tag anchor has been slidingly attached to the suture from the second T-tag anchor, a one-way slip knot is formed within the suture. The suture knot serves to pull together and lock the T-tag anchors when the anchors are under load following deployment.

Figure 11:
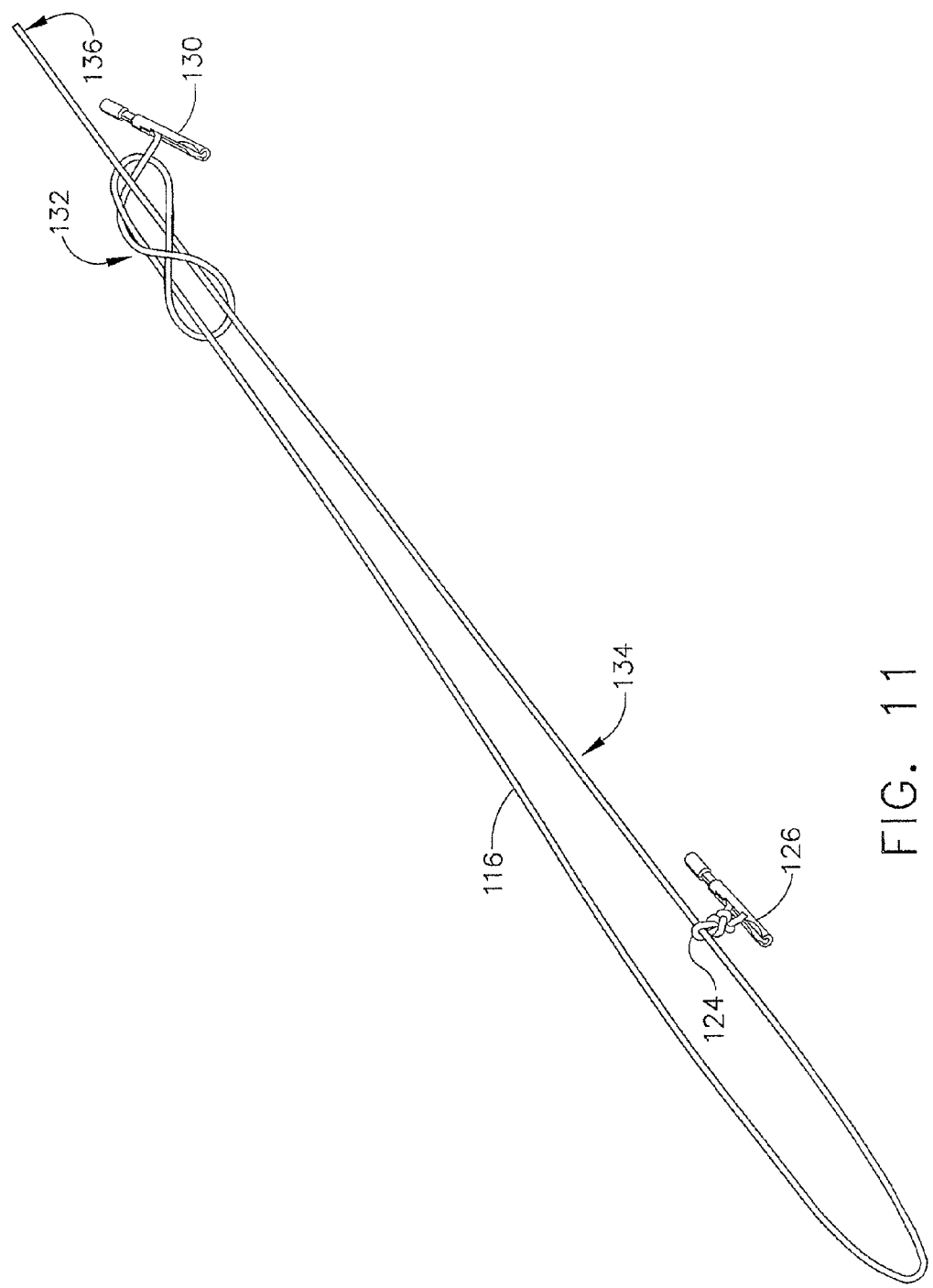
FIG. 11 is an isometric view of a slip knot formed between a pair of T-tag anchors, showing the knot in a loosened form

FIG. 11 illustrates an exemplary suture slip knot 132 for drawing together and securing a pair of T-tag anchors 126, 130. To form the slip knot 132, which is one variation of a hangman's noose, the suture length attached to the second T-tag anchor 130 is doubled over, as indicated by reference numeral 134, and the second T-tag anchor 130 is passed under the suture, as shown in FIG. 12A. The second T-tag anchor 130 is then encircled back over the doubled suture length 134, as shown in FIG. 12B, and passed back under the doubled suture, as shown in FIG. 12C. To complete the encircling of the doubled suture length 134, the second T-tag anchor 130 is brought over the top of the encircling suture, as shown in FIG. 12D. To complete the slip knot, the second T-tag anchor 130 is brought under the doubled suture length 134 and back over the first encircling pass, as shown in FIG. 12E. When the slip knot 132 is fully formed, as shown in FIGS. 11 and 12E, the knot 132 is tightened setting the distance between the knot 132 and T-tag anchor 130, while allowing the doubled suture length 134 to be reduced. Once the T-tag anchors 126, 130 are deployed into tissue, pulling on loose suture end 136 relative to the fixed T-tag anchors 126, 130 reduces the size of the doubled suture length 134 until it cannot be further reduced because of the suture loop 124. As the slip knot 132 is tightened, first and second T-tag anchors 126, 130 are drawn together. The final distance between first and second T-tag anchors 126, 130 is defined by the distance from suture loop 124 to the T-tag anchor 126 and the distance from knot 132 to the T-tag anchor 130. The size of the suture loop 124 may also be used to adjust this overall distance. Additionally, where the suture loop 124 is formed by tying a knot in the suture of a first T-tag anchor 126, the suture knot 132 may be pre-tied in the length of suture before the T-tag anchors 126, 130 are attached. Following formation of the slip knot 132, the first T-tag anchor 126 is attached to doubled suture length 134 by tying a knot to form suture loop 124. The second T-tag anchor 130 is attached to an end of the suture length by crimping the end within the T-tag anchor, and may be done after the knot 132 is created and tightened. The slip knot 132 is only one example of a suitable knot for fastening together a pair of deployed T-tag anchors. One skilled in the art will recognize that other slip knots tied such that one T-tag anchor is slidably attached to a doubled over portion of the slip knot (such as 134) while the other T-tag anchor is secured to a tail or free end of the slip knot remain cinched when forces seeking to loosen the knot are applied only to the T-tag anchors in the system. Additionally evident, although not shown, is that a single piece of suture may be used to create the slip knot 132 and the suture loop 124. This is accomplished by connecting suture end 136 and 117.

After the suture knot and T-tag anchor pair are assembled, the T-tag anchor pair is preferably loaded into suture anchor deployment device 52, such that the first "looped" T-tag anchor 126 deploys initially, followed by the second "attached" T-tag anchor 130 although the order may be switched. Multiple pairs of the pre-tied T-tag anchors may be loaded into the suture anchor deployment device for use during a procedure. For each T-tag anchor pair, the loose suture end 136 extends from the needle slot 86 proximally through the interior of the deployment device housing 62. Outside the proximal end of the deployment device housing 62, the loose suture lengths from the multiple pairs of T-tag anchors are color-coded, labeled, or otherwise distinguished to identify the order of the pairs within the needle stack.

With the pre-tied T-tag anchor pairs loaded into laparoscopic deployment needle 64, the sheathed tip of the needle is pressed against the anterior cavity wall 40 of the gastric cavity 32 to probe the outside surface of the gastric cavity 32, as shown in FIG. 4. The cavity wall indentation can be visualized through the endoscope 30 to determine the proper location to insert the needle. Laparoscopic visualization may be used in addition to or in place of the endoscopic view to determine the proper location. After the proper insertion location is determined, the protective sheath 70 is drawn proximally along the shaft of the needle 64, and the tip of the needle is inserted into anterior cavity wall 40 to reach the interior of gastric cavity 32. The needle 64 is inserted into gastric cavity 32 with sufficient force to prevent the needle 64 from glancing off of the exterior surface of anterior cavity wall 40. Appropriate gastric insufflation pressures ideally provide a sufficiently rigid surface through which the needle may be passed. To prevent the gastric wall from tenting into the cavity interior as needle 64 is inserted (which may allow the posterior gastric wall to be pierced), a grasper may be passed through the endoscope 30 and placed against the inside surface of the wall of the gastric cavity. The grasper provides support on the inside wall of the gastric cavity as the laparoscopic needle is inserted through the anterior wall of the gastric cavity. Laparoscopic instruments may alternatively be used alone, or in conjunction with endoscopic assistance to allow the needle to safely penetrate a single gastric wall.

Figure 14:
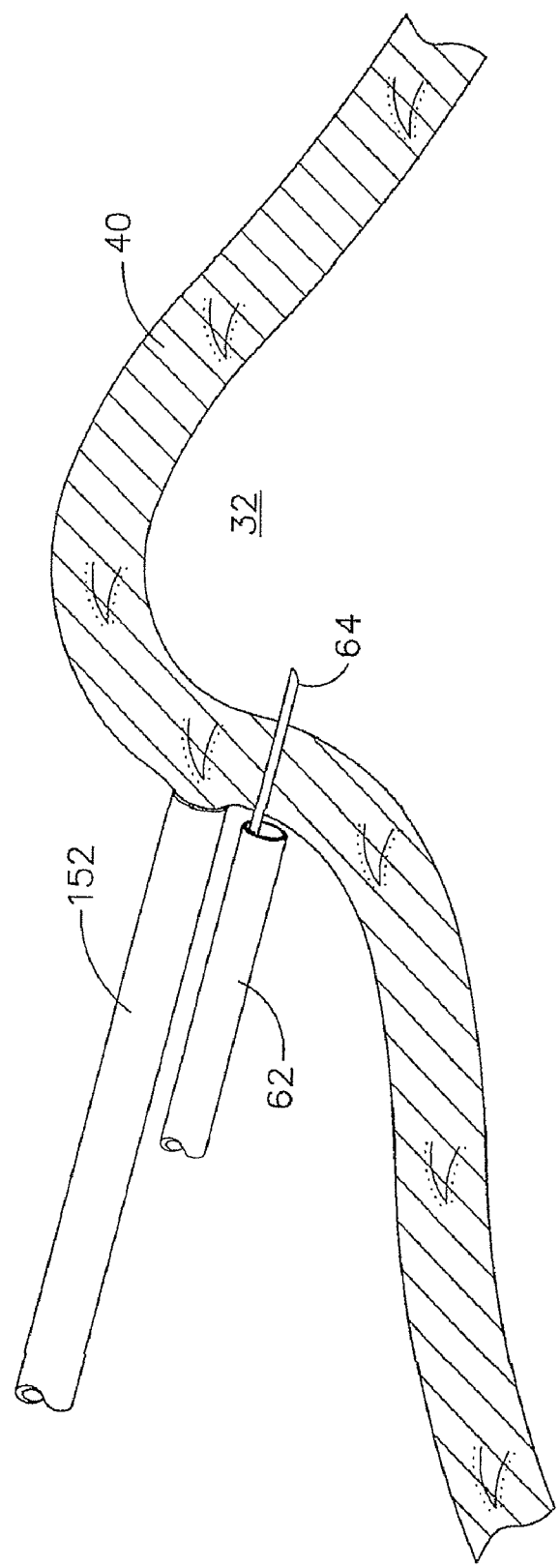
FIG. 14 is a cross-sectional view of an isolated area of the gastric cavity wall during needle insertion.

When inserting the needle 64 through the anterior wall of the gastric cavity, it is desirable to have as close to normal an angle as possible between the needle tip and the targeted surface of the anterior wall of the gastric cavity. To facilitate a more direct needle insertion angle, a vacuum assist may be used in conjunction with suture anchor deployment device 52 to draw the targeted gastric cavity surface against the face of the suture anchor deployment device just prior to T-tag anchor deployment. The vacuum assist may be connected to the suture anchor deployment device, with a vacuum tube extended through the lumen of the deployment device housing 62 alongside the needle 64. Alternatively, a vacuum tube 152 may be run along the outside of deployment device housing 62 through the trocar 50. The tip of the vacuum tube 152 and the tip of the suture anchor deployment device 52 simultaneously act upon the same area of tissue, as shown in FIG. 14, to draw the tissue against the face of the suture anchor deployment device. Following delivery of the T-tag anchor, the vacuum moves along with the suture anchor deployment device to additional targeted tissue surfaces.

Sutures or suture anchoring devices deployed into and/or through the anterior wall of the gastric cavity occasionally pull out of the tissue and fail due to the contact pressure between the suture or suture anchoring device and the impacted tissue. This tendency is particularly acute when tension is consistently applied to the suture anchoring devices by large food volumes caused by patient noncompliance with dietary requirements. To reduce the potential for suture anchoring device failure in the hybrid cavity wall folding procedure, a buttressing device may be used in conjunction with the T-tag suture anchors. The buttressing device distributes the load from the T-tag anchors across a wider area of the cavity tissue, thereby reducing the possibility that tension will pull an anchor through the cavity wall. The cavity wall folding procedure can, however, also be performed without the application of a buttressing device or material.

Figure 15:
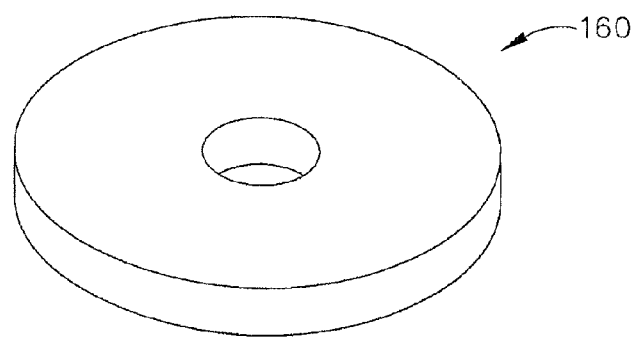
FIG. 15 is a perspective view of an exemplary buttressing device.
Figure 16:
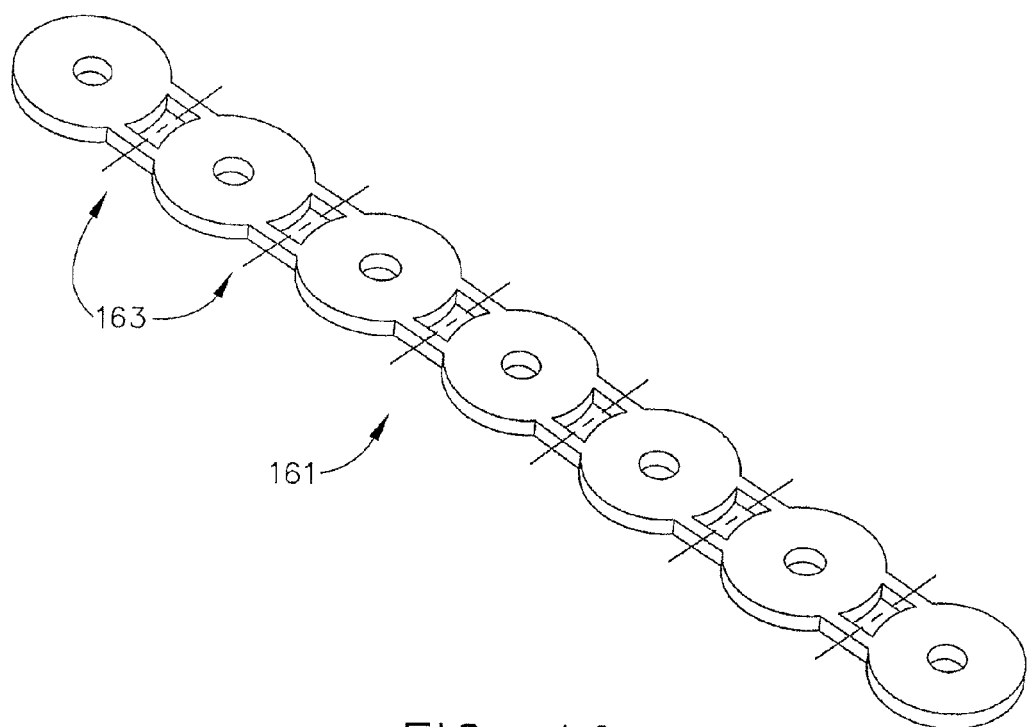

A number of different types of material and configurations can be utilized to form a buttressing device. FIG. 15 shows an embodiment in which a buttressing device 160 has a washer-type shape with a center hole for insertion of the laparoscopic deployment needle. The washer-type device can be made from silicone, closed-cell foam, PEEK, or any other biocompatible, elastically-deformable material. Additionally, buttressing device 160 may be made from an absorbable material, and/or contain medicinal agents that promote healing or scarring to increase the strength of the surrounding tissue. As shown in FIG. 16, in addition to an individual unit, the buttressing devices 160 can be formed as a continuous strip 161 which can include segmented perforations, indicated by dashed lines 163, to break or tear upon application.

Figure 17:
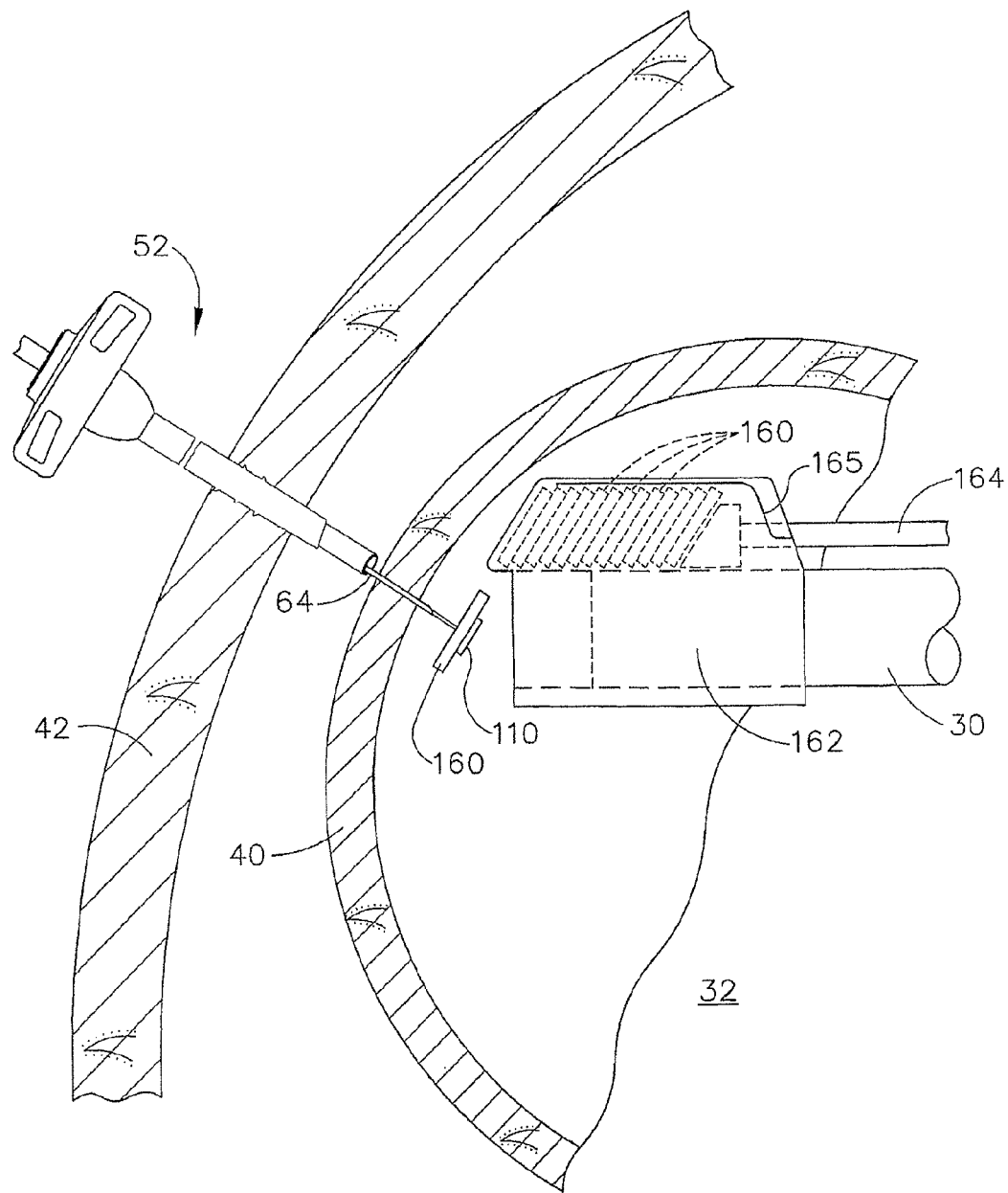
FIG. 17 is a cross-sectional view of a portion of the abdominal and anterior cavity walls during deployment of a T-tag anchor and exemplary buttressing device.

In a hybrid cavity wall folding procedure, buttressing devices are delivered to the interior of the gastric cavity transorally using the endoscope. The buttressing devices may be delivered by use of a conveyor, pull string, or endoscopic cartridge, among other mechanisms. FIG. 17 depicts a first exemplary buttress delivery mechanism in which washer-like buttressing devices 160 are passed transorally into gastric cavity 32 through a cartridge 162. The cartridge 162 is attached to the distal end of the endoscope 30. Multiple buttressing devices 160 are stacked along a track within cartridge 162. An advancement rod 164 applies distal pressure to the proximal most device in the stack, to advance the devices towards the distal end of the cartridge. At the distal most end of the cartridge, a pushrod 165 is positioned to individually advance individual buttressing devices 160 one at a time. The pushrod 165 is preferably made out of a superelastic material such as Nitinol, but one skilled in the art will recognize that multiple mechanisms may be used to dispense individual buttressing devices 160 one at a time. The endoscope 30 may be positioned adjacent the anterior cavity wall 40 of the gastric cavity to align the discharging buttressing device with the insertion location of needle 64. Once aligned, the needle 64 is passed through the discharging buttressing device 160 to deploy a T-tag anchor 110 on the interior side of the device. The needle 64 may of course be first passed through the gastric wall in which case the buttressing device is guided over the needle, however, the buttressing device may also be positioned against the gastric wall in the desired location. In the latter circumstance, the needle 64 is guided to the correct location and then pierces the gastric wall and buttressing device. The cartridge 162 may have features that aid in guiding the needle to the correct location. One skilled in the art will recognize that the shape of the cartridge, as well as light from the endoscope or cartridge may also aid in locating the correct location.

Figure 18:
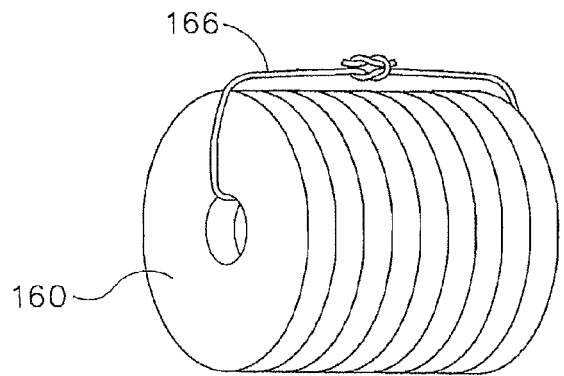
FIG. 18 is a perspective view of a second exemplary embodiment for delivering buttressing devices.
Figure 19:
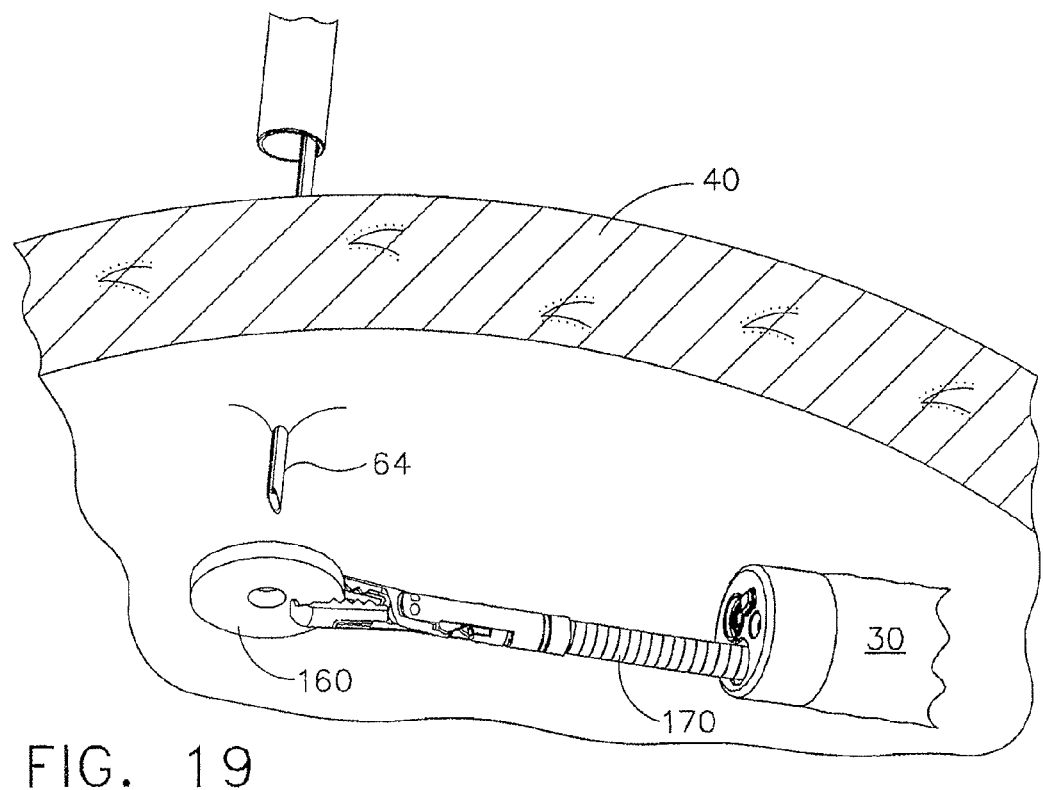
FIG. 19 is a perspective view of the gastric cavity interior during deployment of a T-tag anchor and second exemplary buttressing device.

FIG. 18 depicts a second exemplary buttress delivery method. In this method, multiple buttressing devices 160 are delivered as a unit transorally into the gastric cavity. The devices can be delivered using the endoscope 30 or through an ancillary channel (not shown) into the gastric cavity. Inside the gastric cavity 32, buttressing devices 160 are separated by releasing or freeing (cutting, untying, unhooking, etc) the connecting suture or cable 166. An endoscopic grasper 170 is passed through the working channel of endoscope 30 and utilized in conjunction with the endoscope 30 to individually place and hold buttressing devices 160 against the interior stomach surface, as shown in FIG. 19. Each buttressing device 160 is positioned at an intended needle insertion location. With the buttress in place, the needle 64 is inserted through the anterior cavity wall 40 of the gastric cavity 32. Inside gastric cavity 32, the needle 64 is pushed through the buttressing device. A T-tag anchor or other suture anchoring device is deployed on the interior side of buttressing device 160, so that the attached suture extends through the buttress before passing through the cavity wall. The needle may pass through a hole in the buttress if present, or it may pierce through the buttress.

In yet another exemplary buttress delivery method, multiple buttressing devices 160 can be placed on the distal end of an endoscopic grasper prior to passage of the grasper into gastric cavity 32. The grasper jaws are opened to prevent the buttressing devices from falling off the distal end of the grasper. With the buttressing devices loaded on, the grasper is passed transorally into the gastric cavity. Inside the gastric cavity 32, the grasper jaws are closed to release the buttressing devices inside the gastric cavity 32. The buttressing devices are retrieved as needed from inside the gastric cavity 32 for reinforcement during the plication procedure. If support is desired on the exterior (serosal) surface of the cavity wall, a buttressing device can be passed into the peritoneal cavity through a trocar. The buttressing device can be positioned against the exterior wall surface by a grasper passed through a secondary trocar. In this scenario, the deployment needle is passed through the buttressing device prior to puncturing the cavity wall.

In all cases, the buttress as well as the anchors themselves may be comprised of materials that permit the delivery of therapeutic agents that promote healing, prevent infection, reduce nausea, prevent erosions, induce weight loss, or otherwise provide the patient with a beneficial outcome. The therapeutic agent may be disposed in the implant so as to diffuse or degrade over time in order to advance the treatment or promote healing. U.S. Pat. No. 7,217,425, which is hereby incorporated herein by reference in its entirety, describes implantable devices that incorporate a medicinal agent as a coating. Exemplary medicinal agents for use in the present cavity wall folding procedure include Topomax® brand topiramate, available from Ortho-MeNeil Neurologics, Inc., in Titusville, N.J. Topiramate can reduce the need for food and can be used as an adjunct to the surgical procedure. One skilled in the art will recognize that oral medications may also be used to supplement these effects and that these combination therapies may promote synergies that ultimately greatly increase the efficacy of the surgical procedure.

As an alternative to the washer-like device shown in FIG. 15, a buttressing device can be formed of a solid material that is easily penetrated by a suture anchor deployment needle. A buttressing device can also be formed from a sheet of mesh material having a plurality of spaced openings. When using a mesh or solid material, the material may be configured into a first insertion shape that is sufficiently small to be inserted transorally. After insertion, the material may be reconfigured into an expanded shape or form for use. This shape transformation may be made using different methods including shape memory materials, mechanical compression, folding, tying or a combination of the above.

In addition to buttressing devices, the serosal tissue on the outside surface of the gastric cavity 32 may be treated to reinforce the plication anchors. These treatments may also serve to promote healing between serosal surfaces. Treatment may include abrasion, thermal damage, electrical damage or chemical damage which has the effect of creating scar tissue along the serosal surface. When the treated tissue areas are joined together into a fold, the trauma, treatment, or damage induces an earlier and more rapid healing response that may also serve to promote a stronger, more durable bond. Another method for reinforcing the serosa-to-serosa fold is to inject a chemical solution into the cavity wall. The injected solution toughens the surrounding tissue area to decrease the likelihood of the T-tag anchors eroding through the cavity wall. Chemical solutions (or bulking agents) suitable for this application include chiersoants, tgf-bea, keratin, PMMA (polymethymethaccrolade) among others. Medications that promote healing, such as Vitamin C which raises ascorbic acid levels in the body may also be used to aid in the rapid and durable serosa-to-serosa healing. A vitamin C regime may be started far in advance of the day of surgery. Such medications may also be delivered through the buttress, anchors, or taken orally.

Figure 20:
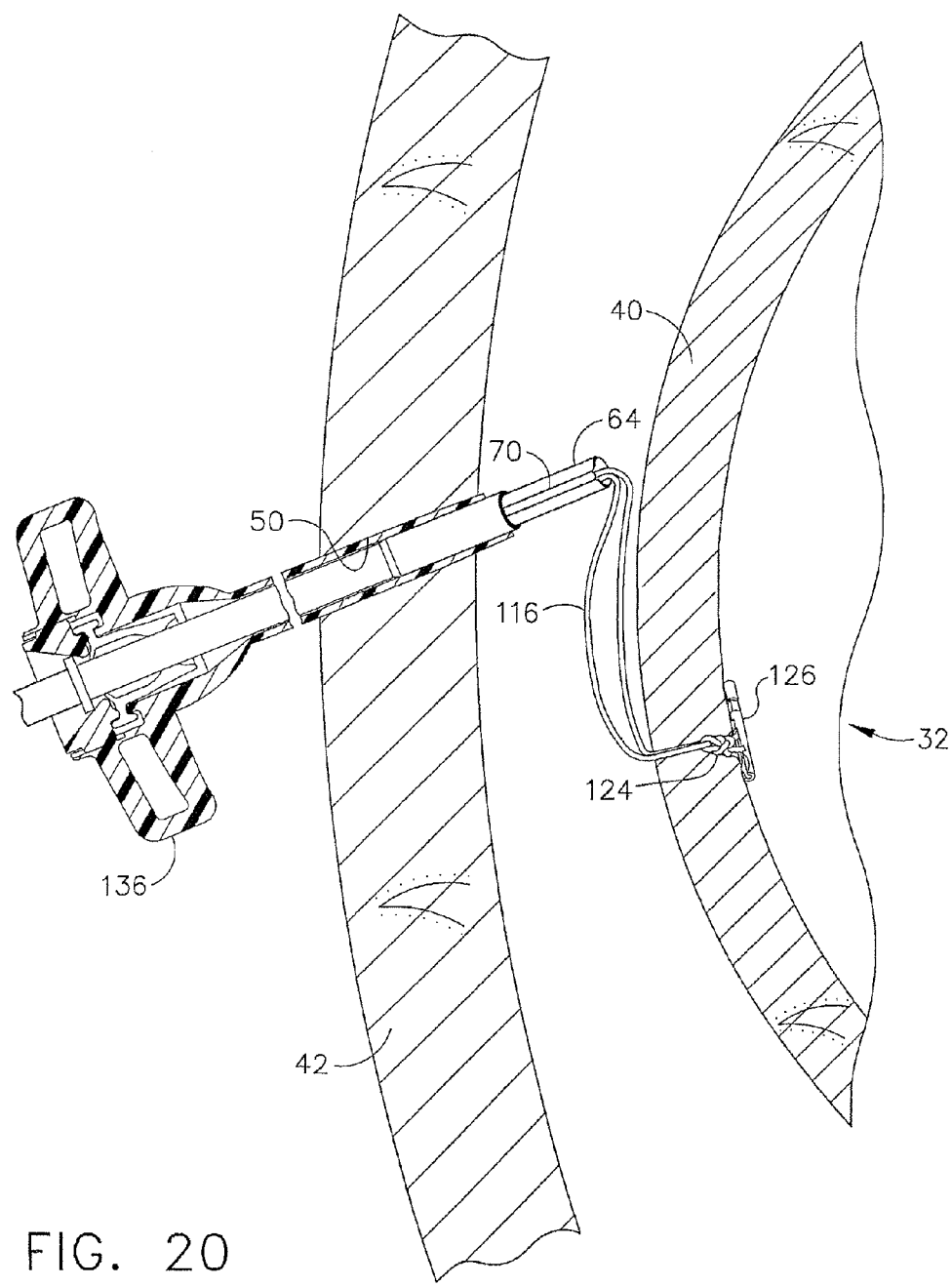
FIG. 20 is a cross-sectional view of an abdominal wall and gastric cavity showing a needle probing the gastric cavity for a second suture anchor location.

After the first T-tag anchor 126 is deployed into gastric cavity 32, either with or without a buttressing device, the needle 64 is removed from the gastric cavity 32. In the preferred case where the suture loop 124 tightly surrounds the suture of the doubled over section 134, when the needle 64 is removed, a portion of the doubled over section 134 remains in the gastric wall. Alternatively, if the suture loop 124 is sufficiently large, as the needle 64 is removed, the suture loop 124 is drawn from T-tag anchor 126 back through the cavity wall. After the needle 64 is removed from the gastric cavity 32, the protective sheath 70 is preferably drawn back over the tip of the needle. The anterior wall of the gastric cavity is again probed with the sheathed needle tip, as shown in FIG. 20, to determine the location for the second T-tag anchor. To facilitate the anterior wall probing, trocar 50 may be flexed at different angles within abdominal wall 42, as shown in FIG. 20, without removing the trocar from the abdominal wall. The trocar 50 is angled within the abdominal wall 42 to enable the needle 64 to enter the gastric cavity 32 at different locations and in as direct an angle as possible to the exterior cavity surface. Once the proper placement location is determined, the needle 64 is once again inserted through anterior cavity wall 40 into gastric cavity 32. With needle 64 inside the gastric cavity 32, the second of the pre-tied T-tag anchors 130 is deployed into the interior of the gastric cavity 32. The second T-tag anchor 130 can be deployed with or without a buttressing device.

Figure 22:
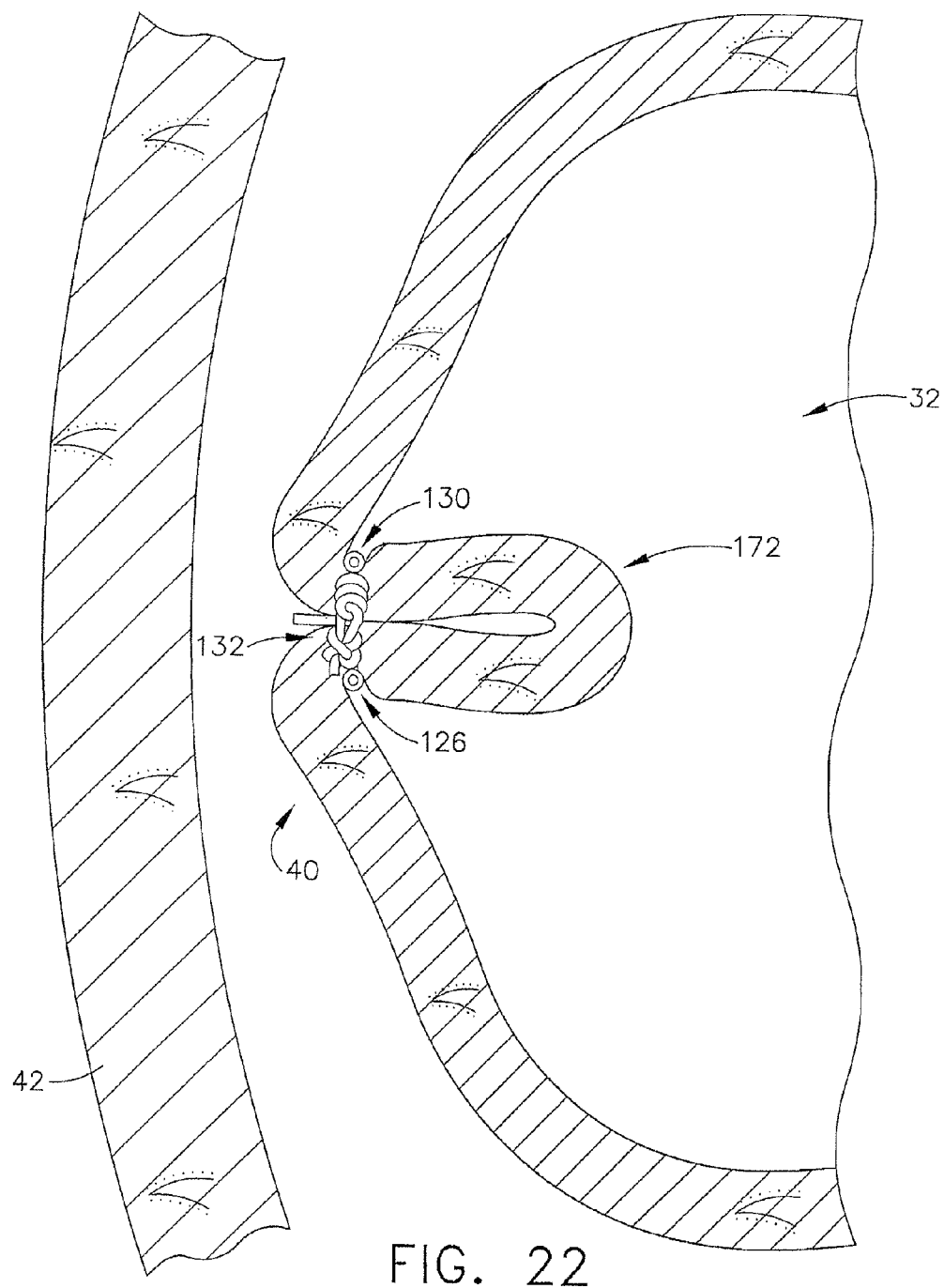
FIG. 22 is a cross-sectional view of an abdominal wall and gastric cavity showing a first embodiment for forming and locking a fold in a gastric cavity wall.

After the second T-tag anchor 130 is deployed, the needle 64 is removed from the anterior cavity wall 40, drawing the attached suture 116 back through the anterior cavity wall 40. With the two T-tag anchors deployed through the cavity wall, tension is applied to loose suture end 136 through the deployment device housing 62, to reduce the size of the doubled suture length 134. As this occurs, the T-tag anchors 126, 130 are drawn together, apposing the serosal tissues surrounding each T-tag anchor. After the T-.Tag anchors and connecting suture have been utilized to appose the cavity wall, the loose suture end 136 is maneuvered into the stem of cutout 80 and around the angled cutting edge as shown in FIG. 21A. With tension applied to the proximal, loose end of the suture from outside the suture anchor deployment device, the protective sheath 70 is retracted in the direction indicated by the arrows, to draw the suture taut within cutout 80 and sever the suture. Following severing, the loose suture end 136 is withdrawn proximally through the trocar 50. FIG. 22 shows gastric cavity 32 with the T-tag anchors 126, 130 cinched and locked together by a slip knot 132 to appose the exterior, serosal layer of the gastric cavity wall and form a fold 172. Of course, laparoscopic cutting instruments (such as scissors) may also be used to cut the suture.

As an alternative to using pre-tied T-tag anchor pairs, T-tag anchors having separate, attached lengths of suture may be deployed in a spaced relationship through the cavity wall. In this approach, the separate strands of suture from each of the T-tag anchors extends through the anterior wall and proximally through deployment device housing 62. Tension is applied to the proximal ends of the suture strands outside of the deployment device to appose the cavity wall tissue surrounding the T-tag anchors. To lock the suture strands and surrounding tissue in a tensioned, apposed state, a knotting element can be applied to the proximal suture ends and advanced through the trocar to the exterior edge of the cavity wall fold. A knotting element is applied by passing the loose, proximal ends of the suture strands through a knotting element applier, such as the knotting element device which is described in commonly owned and pending U.S. patent application Ser. No. 11/437,440, filed May 19, 2006, which is hereby incorporated herein by reference in its entirety.

Figure 23:
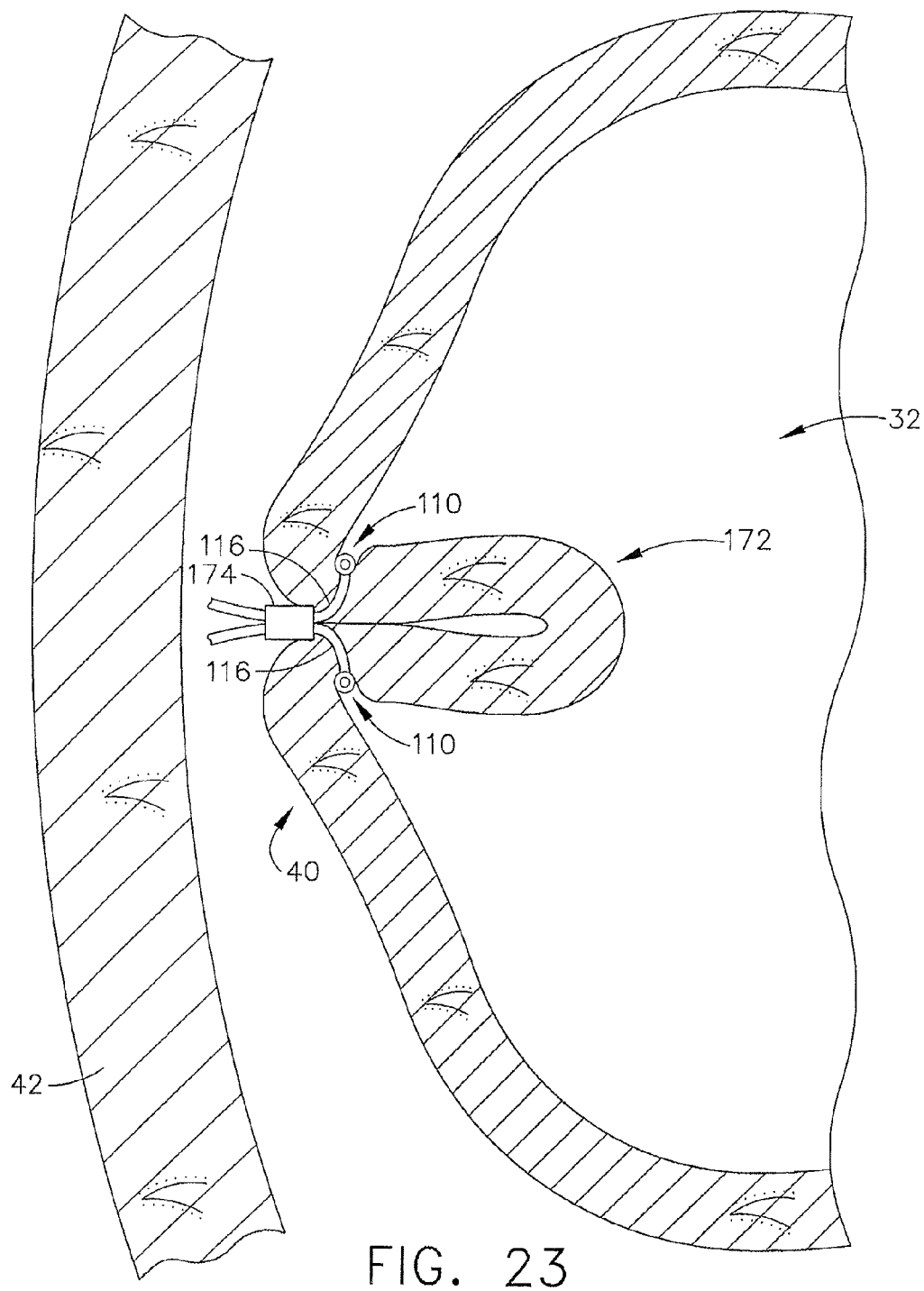
FIG. 23 is a cross-sectional view of an abdominal wall and gastric cavity showing a second embodiment for forming and locking a fold in a gastric cavity wall.

As an alternative for applying a knotting element, the knotting element applier can be loaded or otherwise incorporated into deployment device housing 62 along with a pair of T-tag anchors, so that the T-tag anchors and knotting element are all delivered through the suture anchor deployment device. In this case, the suture anchor deployment device 52 is loaded with the two T-tag anchors, and the suture strands from the anchors are extended out needle slot 86. The suture strands are loaded through the knotting element applier, and the applier passed through a slot in deployment device housing 62 and inside protective sheath 70. After the pair of T-tag anchors is deployed, the knotting element applier is extended distally from the open end of deployment device housing 62. The proximal ends of the suture strands are pulled to appose the tissue surrounding the T-tag anchors. When satisfactory apposition is achieved, the knotting element device is deployed to fasten the sutures together and cut the sutures. FIG. 23 shows gastric cavity 32 with a pair of T-tag anchors 110 deployed through the cavity wall. Suture strands 116 from each of the T-tag anchors are tensioned to pull the surrounding wall tissue into a fold 172. A knotting element 174 is shown applied to the tensioned suture 116 to maintain the cavity wall in the apposed, folded position. Knotting element 174 may also serve as a delivery means for therapeutic agents that provide the patient with an improved outcome.

In addition to separately loading T-tag anchors and a knotting element applier into a suture anchor deployment device, the T-tag anchors and knotting element applier can be assembled together as a cartridge. The cartridge releasably mates with a suture anchor deployment device so that a single deployment device can fire multiple sets of T-tag anchors from multiple cartridges. Likewise, a pair of T-tag anchors and a knotting element applier may be combined together into a single use, disposable deployment device that fires a pair of anchors, cinches suture from the anchors, and then deploys a knotting element to fasten and cut the suture. In another embodiment, a deployment device cartridge may incorporate a Suture Assistant type knot to cinch and fasten suture from T-tag anchors. As discussed previously, one skilled in the art will recognize variations of knots that can be easily tailored for this application. In this embodiment, the elements of the design for delivering the knot in the Suture Assistant comprise the top half of the device, and the bottom half of the device contains a pair of T-tag anchors, a retractable needle, a length of suture connecting the T-tag anchor, and a hook/gaff for grabbing and tensioning the suture after T-tag anchor deployment to appose tissue. More description in further detail on the Suture Assistant can be found in U.S. Pat. No. 5,846,254, which is herein incorporated herein by reference.

In addition to applying a knotting element, suture strands 116 can be locked in a tensioned state by tying a knot in the proximal ends of the suture strands. The knot may be tied laparoscopically through a trocar 50. Alternatively, the knot may be tied external of the body, and the finished knot passed back through the trocar 50 to a point between the abdominal wall 42 and the anterior cavity wall 40 of the gastric cavity 32.

Figure 24:
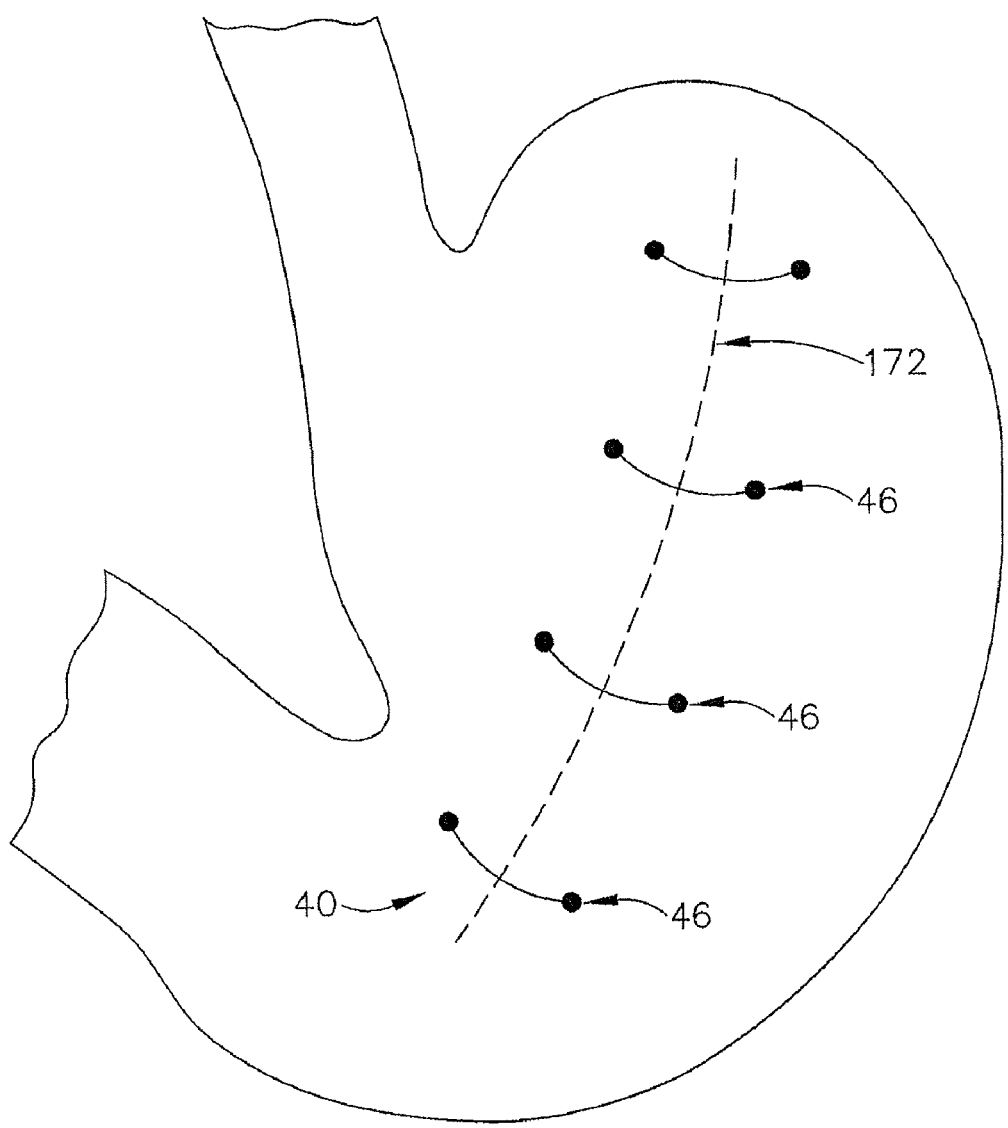
FIG. 24 is a diagrammatic, exterior view of a gastric cavity showing the placement of a first series of suture anchors.

As shown diagrammatically in FIG. 24, one or more additional pairs of suture anchoring devices, indicated by reference numeral 46, may be deployed along the longitudinal length of the cavity wall. The trocar may be flexed within the abdominal wall, or removed and repositioned within the abdominal wall as necessary, in order to reach all of the desired suture anchor locations. Suture material is cinched together between each pair of the devices to extend the length of the cavity wall fold 172. The number of suture anchor pairs used to form a fold will depend upon the desired length for the fold and the desired spacing selected between anchor pairs. Preferably, each of the pairs of suture anchors is evenly spaced apart along the length of the desired fold line. Likewise, within each individual pair the suture anchors are evenly spaced apart across the fold line, so that a uniform tissue fold is formed without distortion or bunching. The proper relative spacing of the suture anchoring devices can be ascertained through the endoscope. Alternatively, an additional trocar may be inserted into the abdominal wall and used in conjunction with an optical instrument to visually determine the proper locations for the suture anchoring devices laparoscopically.

Figure 25:
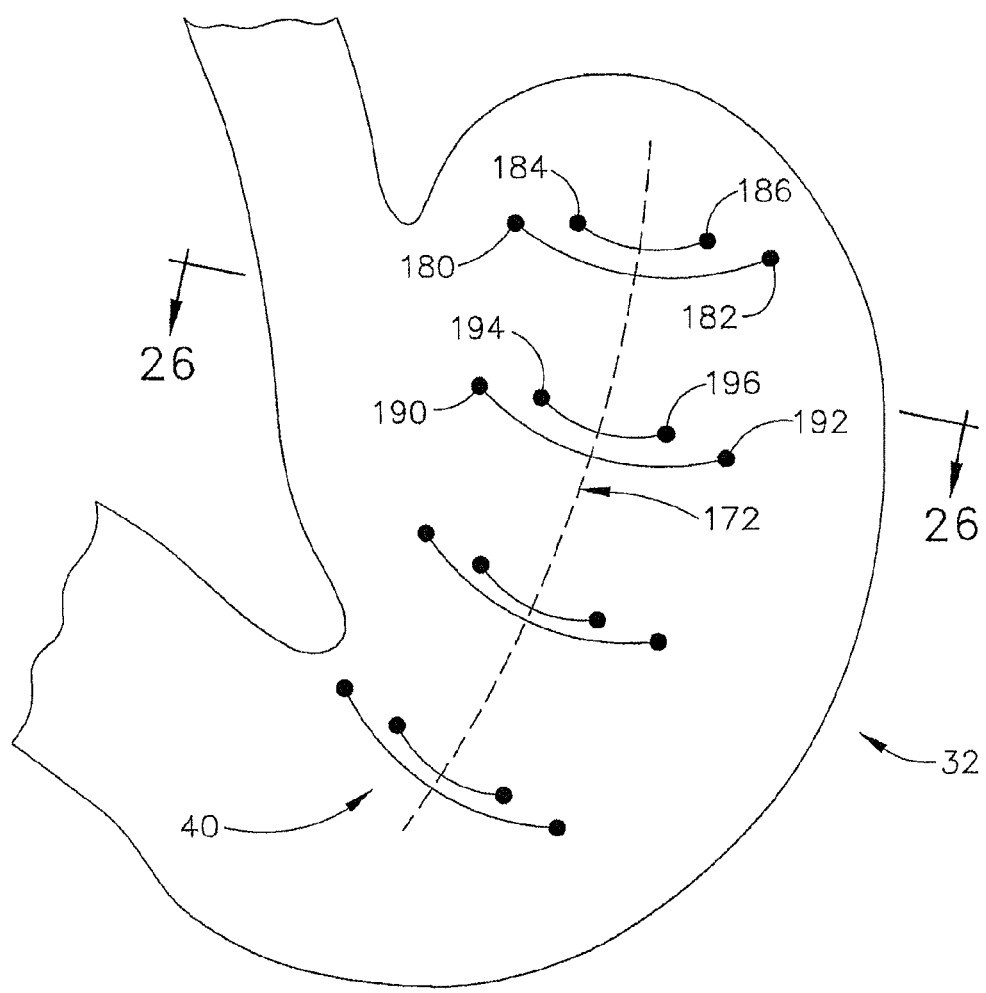
FIG. 25 is a diagrammatic, exterior view of a gastric cavity showing the placement of two series of suture anchors.

After an initial series of T-tag anchor pairs are deployed into the anterior cavity wall 40 and cinched together to form a fold 172, a second series of T-tag anchor pairs is preferably deployed. The second series of T-tag anchor pairs is deployed to form a second fold about the first fold, increasing the depth of the fold. The depth of fold 172 is determined by the distance between pairs of T-tag anchors located at the same point along the length of the fold. FIG. 25 shows the exterior surface of anterior cavity wall 40 with a second series of T-tag anchors deployed to increase the depth of fold 172. In the second series of T-tag anchors, the anchors are deployed in a spaced relationship from the initial series of T-tag anchors in a direction away from fold line 172. Accordingly, in the second series of anchoring devices, T-tag anchors 180, 182 are deployed outside of the initial pair of anchoring devices identified by reference numbers 184, 186. Likewise, the second series anchors 190, 192 are deployed outside of the first series anchors identified as 194, 196. Each of the second series of T-tag anchors are positioned and deployed in the same manner as the initial series of T-tag anchors. After deployment of each second series T-tag anchor pair, the anchors are cinched together by tensioning the loose suture end to appose the surrounding cavity wall tissue. The cinched T-tag anchors are held in place either by a suture knot, such as slip knot 132, by a knotting element, or by other secure means such as the Lapra-Ty® Absorbable Suture Clip, available from Ethicon Endo-Surgery in Cincinnati, Ohio.

Figure 26:
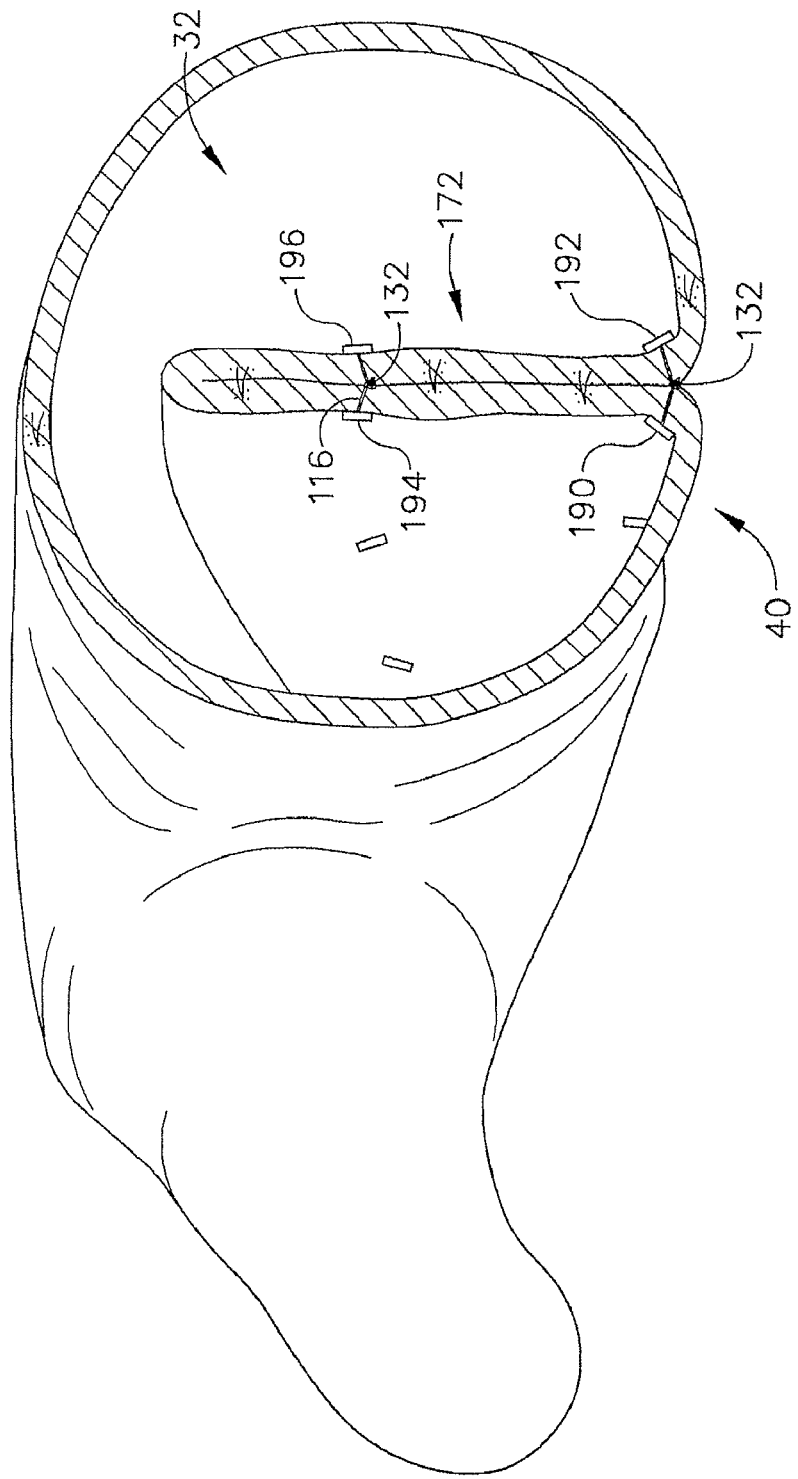
FIG. 26 is a cross-sectional view taken along line 26-26 of FIG. 25, showing the interior of a gastric cavity with a uniform wall fold.

As shown in FIG. 25, the second series of suture anchoring devices preferably includes the same number of anchoring pairs as the first series, so that a uniform depth fold is created. Each of the pairs of anchoring devices in the second series is aligned longitudinally along the length of the fold with the other pairs of anchoring devices to maintain a uniform line for the fold. FIG. 26 shows two rows of longitudinally spaced T-tag anchor pairs forming fold 172 in the interior of gastric cavity 32. As shown in this Figure, fold 172 involutes into the interior of the gastric cavity so that the serosal layer of the cavity wall is brought into contact with itself along the center of the fold. As shown in FIG. 26, each pair of T-tag anchors is pulled together by the attached suture, and the tension in the suture locked in by tightening a slip knot 132. Alternatively, tension may be locked into the suture to hold the cinched tissue together by a knotting element or other type of suture knot. The T-tag anchoring devices are placed through the cavity wall to maintain the serosal to serosal contact within the fold during healing.

To promote healing along fold 172, the serosa may be affected where the cavity wall portions abut within the fold. The serosa may be affected physically by abrading, or thermally or electrically damaging the targeted areas of the serosa, via the trocar, prior to drawing the tissue areas together. The serosa may also be affected chemically by applying shcelorsants, TOF Beta, Keratin or other known surface affecting agents. Traumatizing the serosa in this fashion, either to induce an injury (abrasion), or to enhance healing (Keratin), produces a healing response within the tissue producing a more rapid and potentially more durable formation of an adhesive bond between the contacting serosal surfaces.

Following deployment of the second series of anchoring devices, additional series of anchoring devices may be deployed to further increase the depth of the fold The additional series of anchoring devices are deployed in a spaced relationship from the previous series of suture anchoring devices in a direction away from the fold line. Additional series of anchoring devices may be deployed to permanently increase the depth of the fold in which case the spacing between anchor sets is small resulting in a dense line of anchor sets. Alternatively, an additional series of anchoring devices may be deployed to provide reinforcement during the healing process. Following formation of the serosa-to-serosa fold, healing may not occur over the full depth of the fold due to less than full contact between the abutting serosa layers. Accordingly, where deeper healing is desired, a reinforcement series of suture anchors may be deployed to temporarily increase the depth of the fold.

Figure 27A:
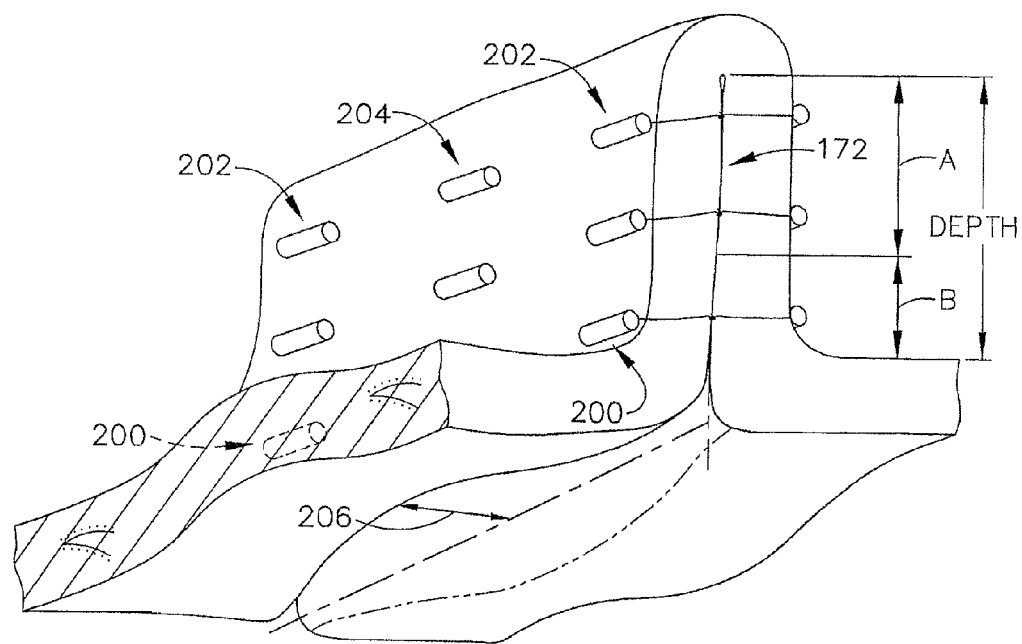
FIGS. 27a and 27b show a perspective and an external view of a portion of a gastric cavity wall fold showing three rows of anchors, the third of which are spaced farther apart than the previous two rows.
Figure 27B:
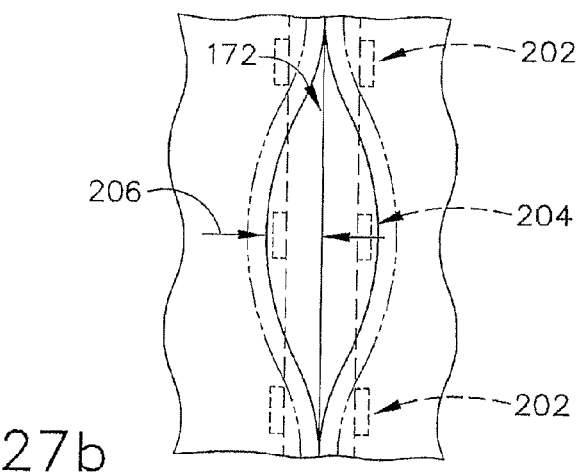

FIG. 27A shows a gastric wall fold section in which a third series of T-tag anchoring devices is deployed to temporarily increase the fold depth. The third series of anchoring devices, indicated by reference number 200, may be placed at a lower density than the initial series of anchors, yet still promote deeper healing within the fold than would occur without the reinforcement anchors. In FIGS. 27A and 27B, the reinforcement series of anchoring devices 200 is shown with anchors placed only at every other location of the permanent anchors. Thus, three series of suture anchors are deployed at locations 202, while only two series of suture anchors are deployed at location 204. In this example, good serosa-to-serosa healing would occur in zone A, while only marginal healing would occur in zone B, due to the lack of an additional row of suture anchors. Portions of the tissue fold opening may bulge, as indicated by reference numeral 206, due to the reduced number of anchoring devices in the reinforcement series. Bulges 206 coincide with the areas of the fold line that lack a reinforcement anchor. The reinforcement anchors may be designed to fail, be absorbed into the body, or otherwise degrade over time after healing has occurred along the primary depth of the fold. In addition to deploying extra rows of suture anchors through the exterior surface of the gastric cavity 32, the fold may be reinforced by applying fastening devices including anchors, staples, etc. to the internal side of the cavity wall.

Figure 28:
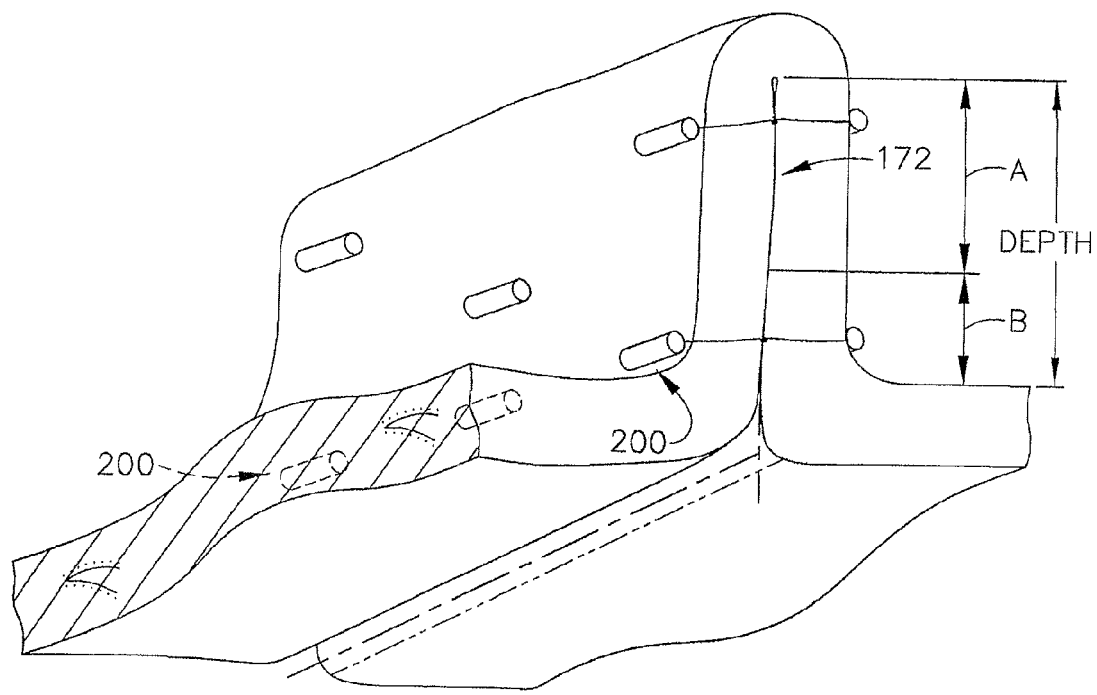
FIG. 28 shows a perspective view of a portion of a gastric cavity wall fold showing three rows of anchors, the third of which is spaced closer together than the previous two rows.

T-tag pairs in Zone B are exposed to gastric wall tensions whereas T-tag pairs in Zone A are likely exposed to much lower stresses. The pattern deployed in FIG. 27A may serve to ensure serosa-to-serosa healing in Zone A, while sacrificing it in Zone B. To increase the likelihood of serosa-to-serosa healing in Zone B, buttress may be selectively used in the region. Yet another alternative to the pattern in FIG. 27A is to have a very dense suture anchor pattern in Zone B, and a less dense pattern in Zone A (see FIG. 28). Numerous patterns can be employed with patterns including numerous combinations of high and low density regions. Buttress may be deployed randomly (if at all), or targeted to high stress areas such as the ends of rows or partially or completely through a load bearing row.

Figure 29:
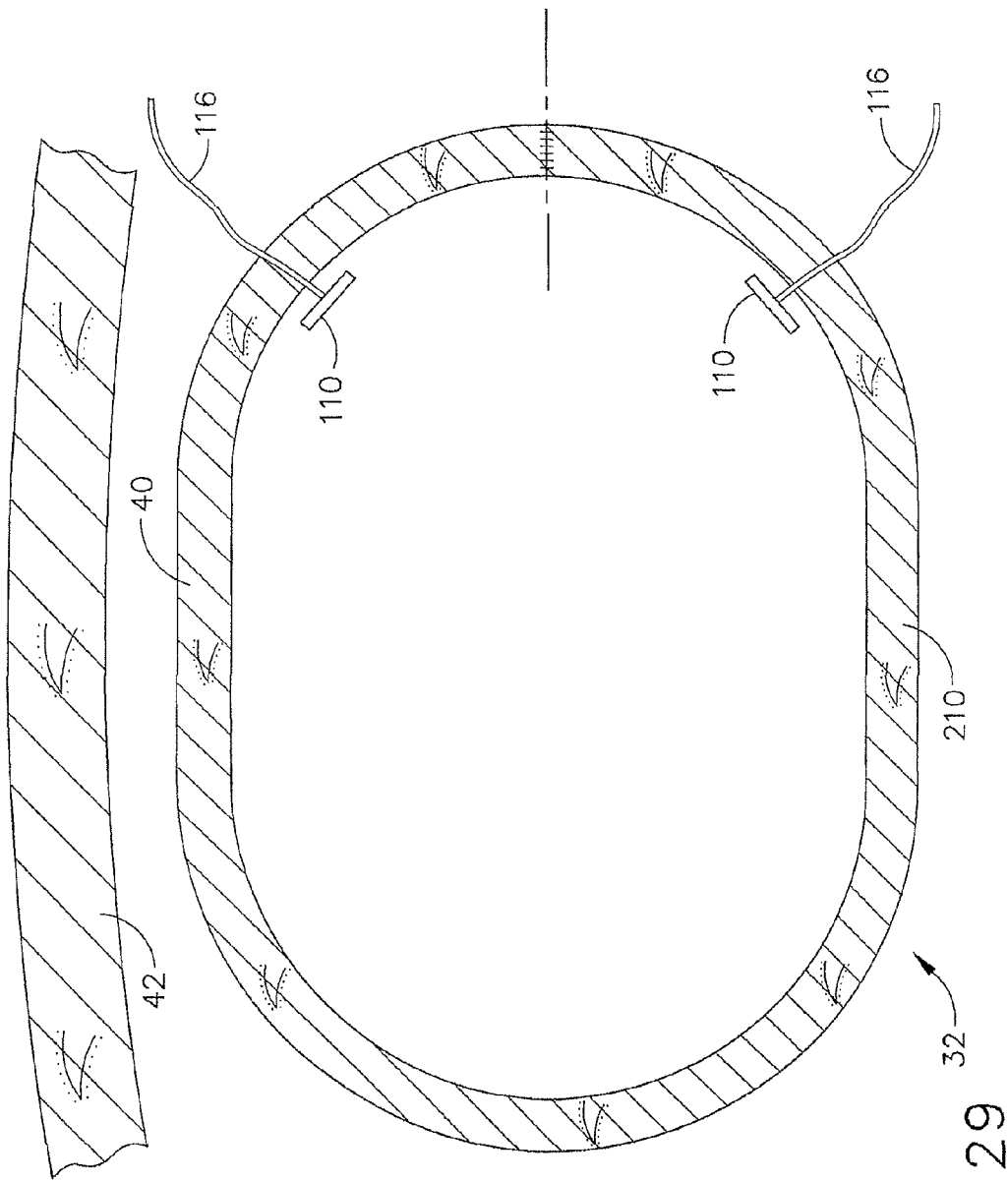
FIG. 29 is a cross-sectional view of a gastric cavity showing T-tag anchors deployed into the anterior and posterior cavity walls.
Figure 30:
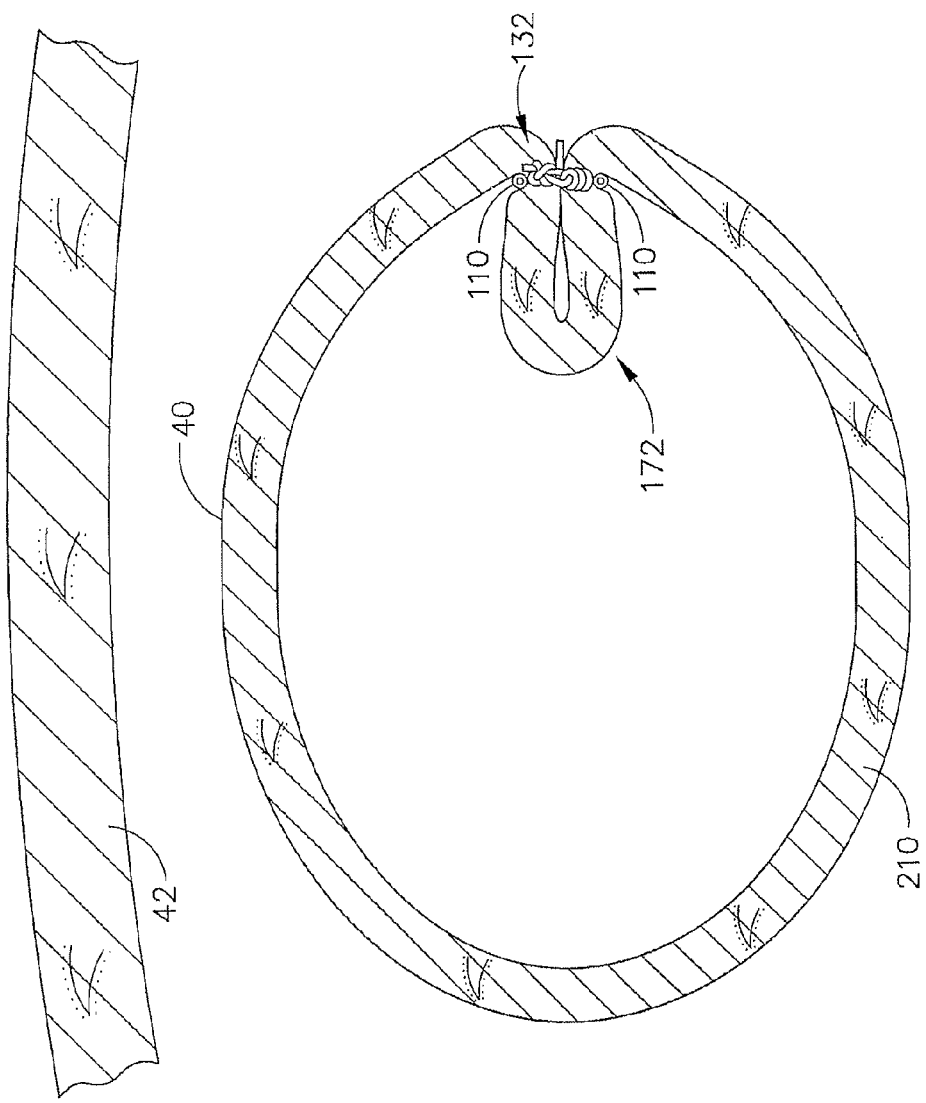
FIG. 30 is a cross-sectional view of a gastric cavity similar to FIG. 29, showing the anterior and posterior walls cinched together into a fold.

As an alternative to a single, centralized fold in the anterior wall, a large fold may be formed apposing the anterior and posterior walls along the greater curve of the cavity. To form this larger fold, T-tag anchors 110 are deployed into both anterior cavity wall 40 and posterior cavity wall 210 as shown in FIG. 29. Posterior wall 210 can be accessed through the laparoscope by cutting through the cavity attachment points along the greater curvature. The attachment points can be safely severed provided one of the many redundant blood supplies to the gastric cavity remains intact. After T-tag anchors 110 are placed in both the anterior and posterior walls, suture attached to the anchors is cinched together and secured by a knot or knotting element to form a deep fold 172 along the greater curve, as shown in FIG. 30.

As an alternative to using T-tags or other suture anchoring devices as described above, cavity wall folds may be formed using suture material alone, without an additional anchoring device. In this alternative method, serosa-to-serosa folds are formed by manipulating needles and suture to create suture bites through the cavity wall. Pairs of the suture bites may be cinched together to approximate the tissue into a fold. This suture only method can be accomplished through manual open/laparoscopic techniques, or through the use of open/laparoscopic/endoscopic suturing devices. A number of different commercially available suture applying devices may be utilized to form suture bites in this method. These devices include, but are not limited to, the Ethicon Endo-Surgery Suture Assistant, Auto-Suture (manufactured by Tyco), Endo-Stitch (manufactured by U.S. Surgical), Pare Surgical Quick Stitch, Ethicon Endo-Surgery Endoscopic Suturing System, Pare Surgical Flexible Endoscopic Suturing System, and the LSI Solutions Sew-Right suturing system. Following cinching of the suture bites, the cavity wall fold may be secured by laparoscopically tying knots or applying knotting elements as described above.

Figure 31:
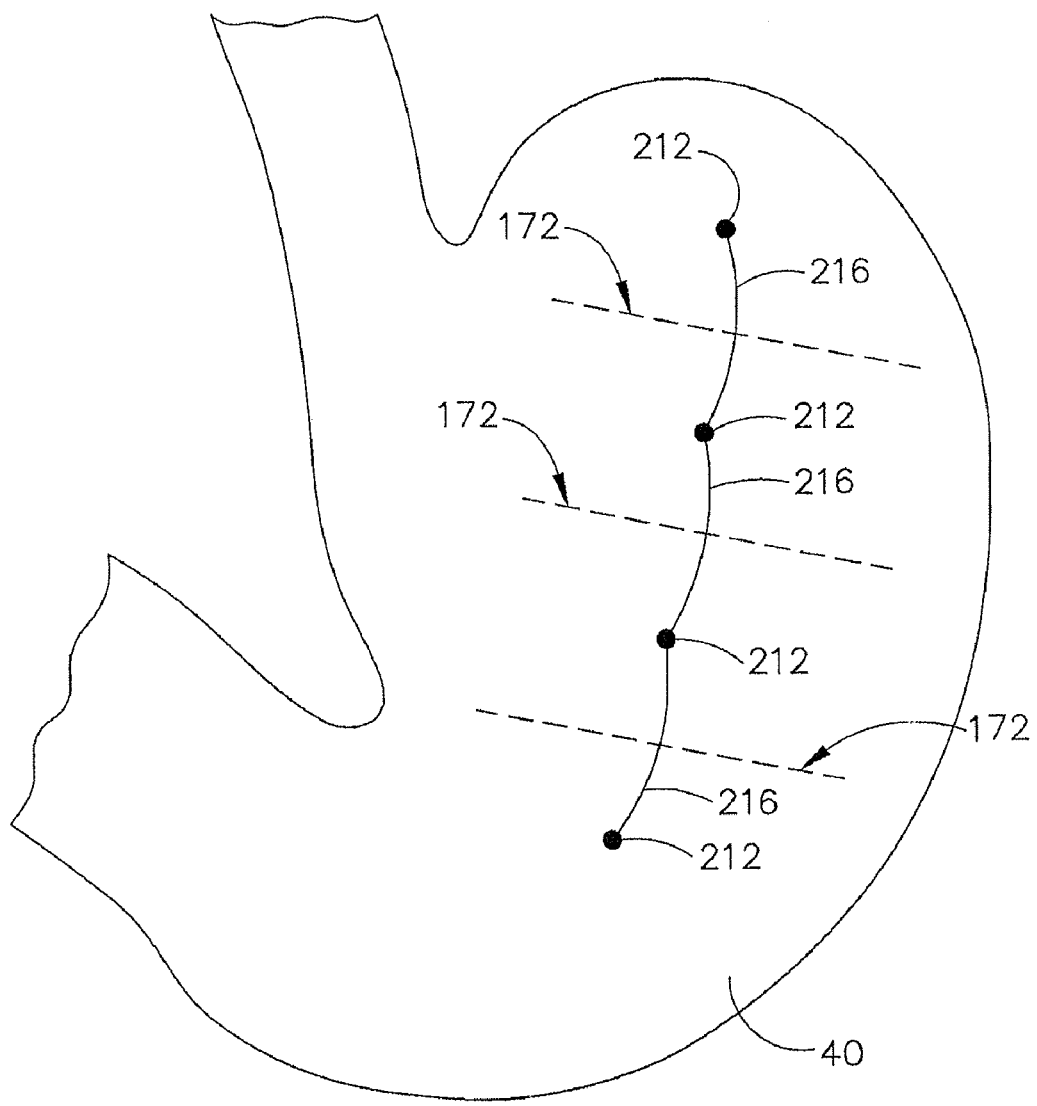
FIG. 31 is an exterior view of a gastric cavity showing a first alternative wall folding embodiment.

FIG. 31 shows an alternative embodiment for forming folds in anterior cavity wall 40. In this embodiment, a plurality of suture anchoring devices 212 are longitudinally spaced along the length of anterior cavity wall 40. Suture anchoring devices 212 may be T-tag anchors, as described above, or any of a variety of other types of tissue fastening devices. Suture material, identified as 216, is cinched and secured between each of the anchoring devices 212 to produce one or more, parallel folds 172 extending across the width of anterior cavity wall 40. In this embodiment, volume reduction is achieved by creating a number of smaller tissue folds, rather than creating a single, long fold. In this example, fold lines do not run proximal to distal, but roughly perpendicular to the midline of the stomach. Of course, any range of angles relative to the midline can be used. One skilled in the art will recognize that orientation as well as length and depth of these one or more folds can be easily varied to achieve the desired effect. As an example and in addition to volume reduction, one or more of these folds may be positioned to create inlet or outlet restrictions.

Figure 32:
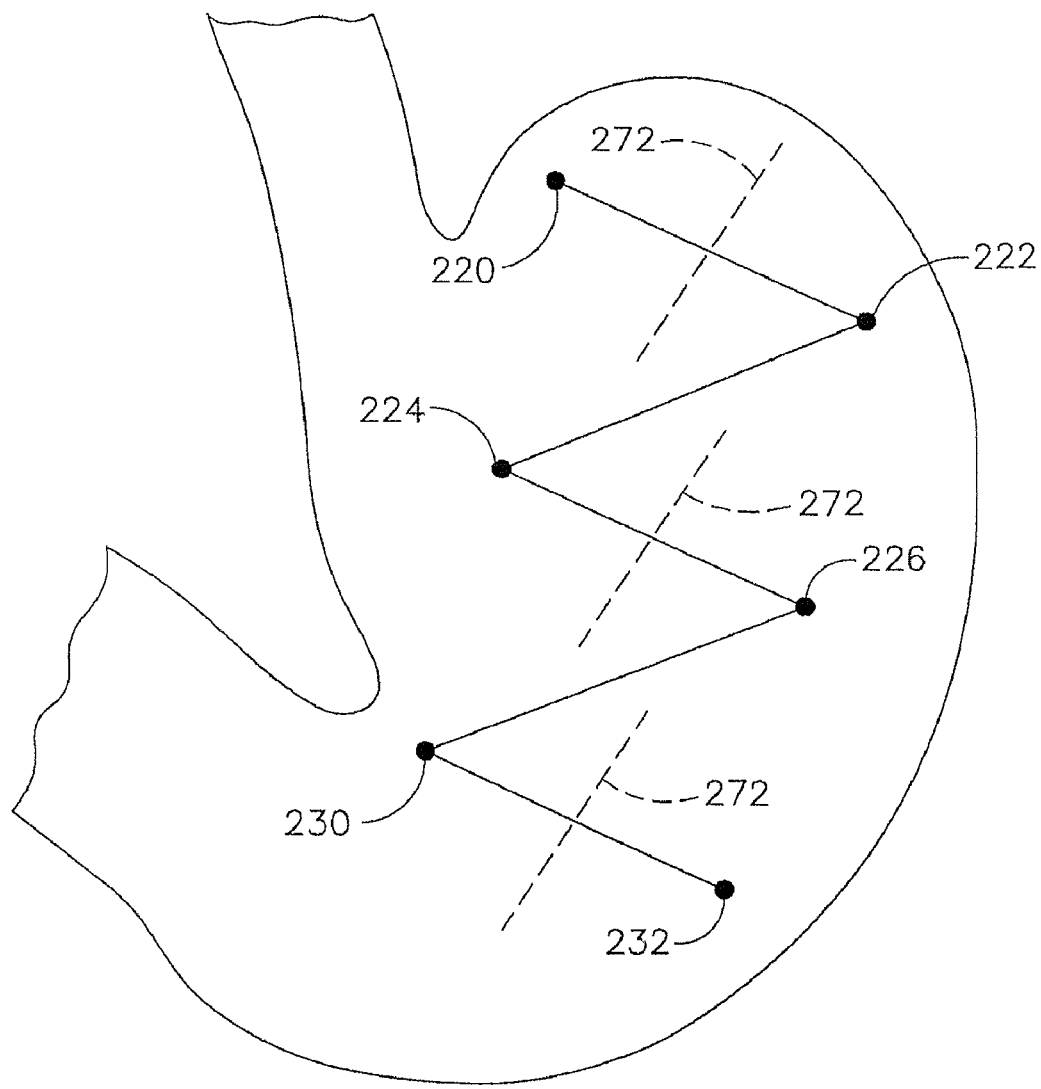
FIG. 32 is an exterior view of a gastric cavity showing a second alternative wall folding embodiment.
Figure 33:
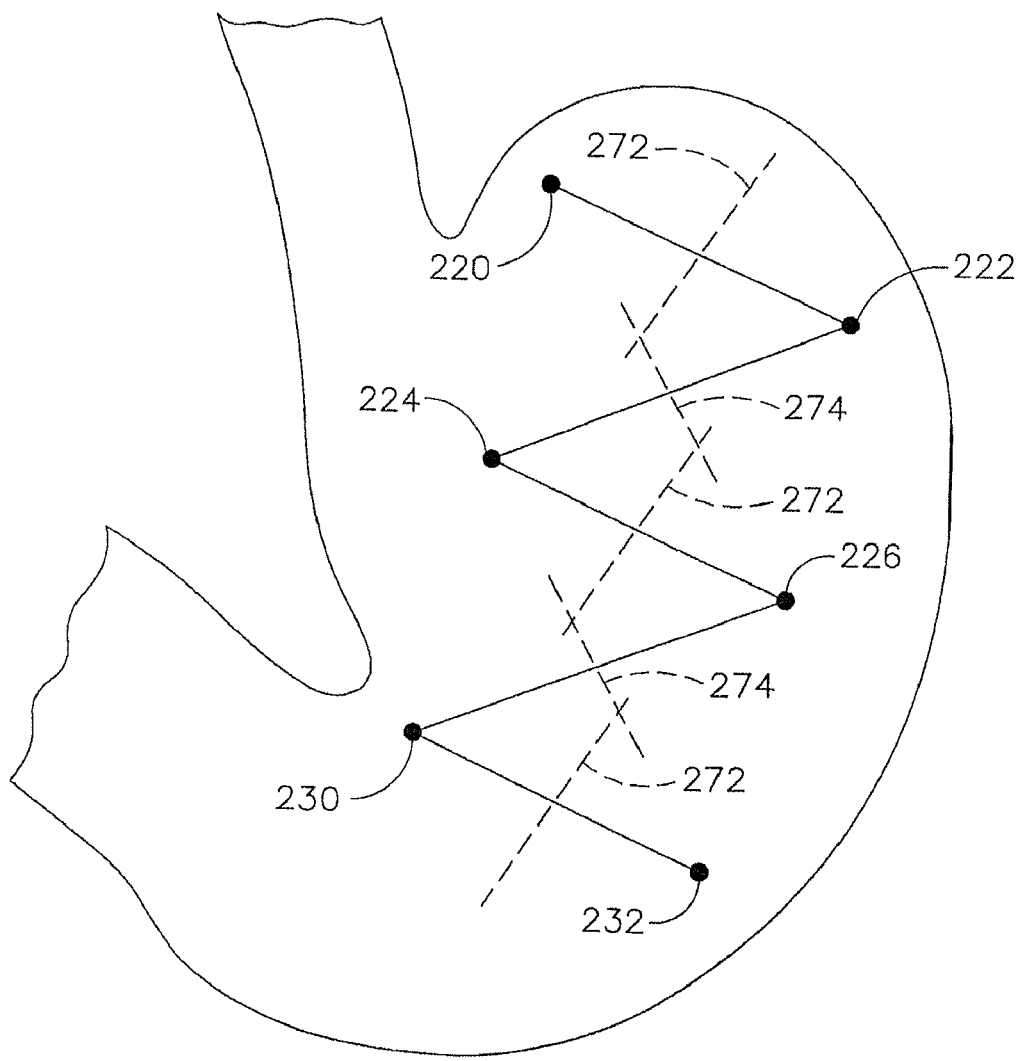
FIG. 33 is an exterior view of a gastric cavity similar to FIG. 32, showing suture tensioned to form an additional set of wall folds.

FIGS. 32 and 33 show a third alternative embodiment for achieving volume reduction through gastric wall folding. In this embodiment, a series of suture anchoring devices is deployed in anterior cavity wall 40. Individual pairs of suturing anchoring devices are diagonally spaced across the width and length of gastric cavity 32 to form a plurality of folds. In FIG. 32, suture extending between each of the anchoring device pairs 220-222, 224-226, and 230-232 is tensioned to form parallel-extending, diagonal folds 272. In the embodiment shown in FIG. 33, suture is also cinched between anchoring device pairs 222-224, and 226-230 to form an additional set of parallel extending folds 274. Suture extending between the anchoring device pairs may be cinched together and held in place by tightening the pre-tied slip knots between the suture anchor pairs. Where alternative types of suture anchors are utilized, the suture may be cinched and secured by knotting elements, standard suture knots, or the like. In the embodiment shown in FIG. 33, the two different sets of parallel extending fold lines 272, 274 are in different planes, thereby creating a bunching effect within the gastric cavity which reduces the available food volume.

Figure 34:
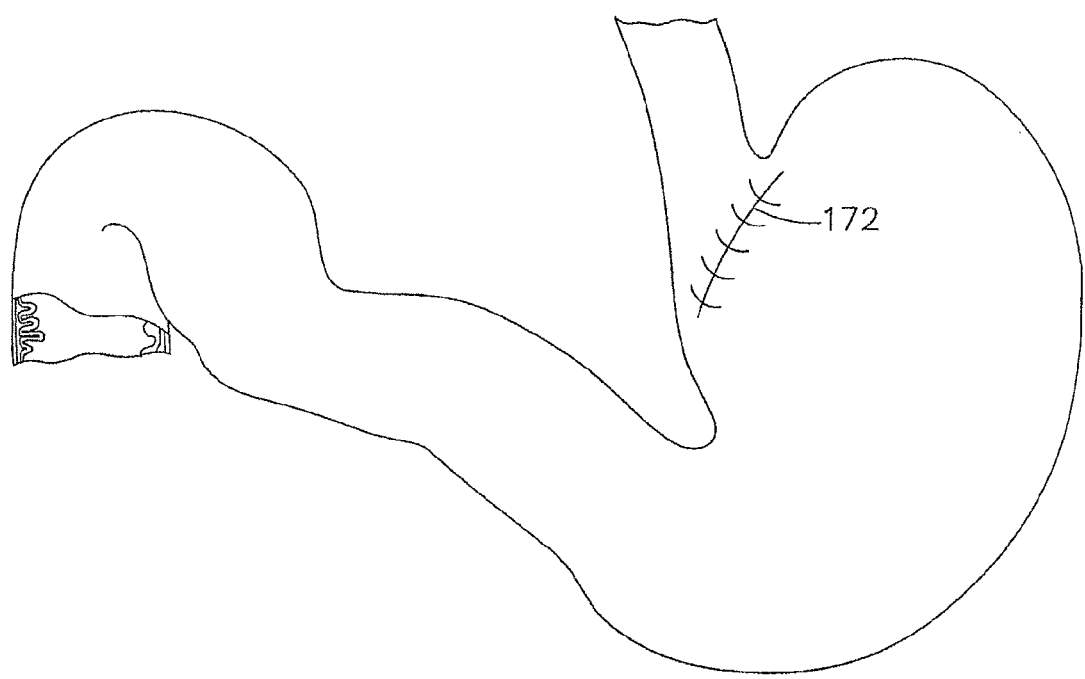
FIG. 34 is an exterior view of a gastric cavity showing a fold placed near the gastroesophageal junction to create a reduced size food pouch or inlet restriction.
Figure 35:
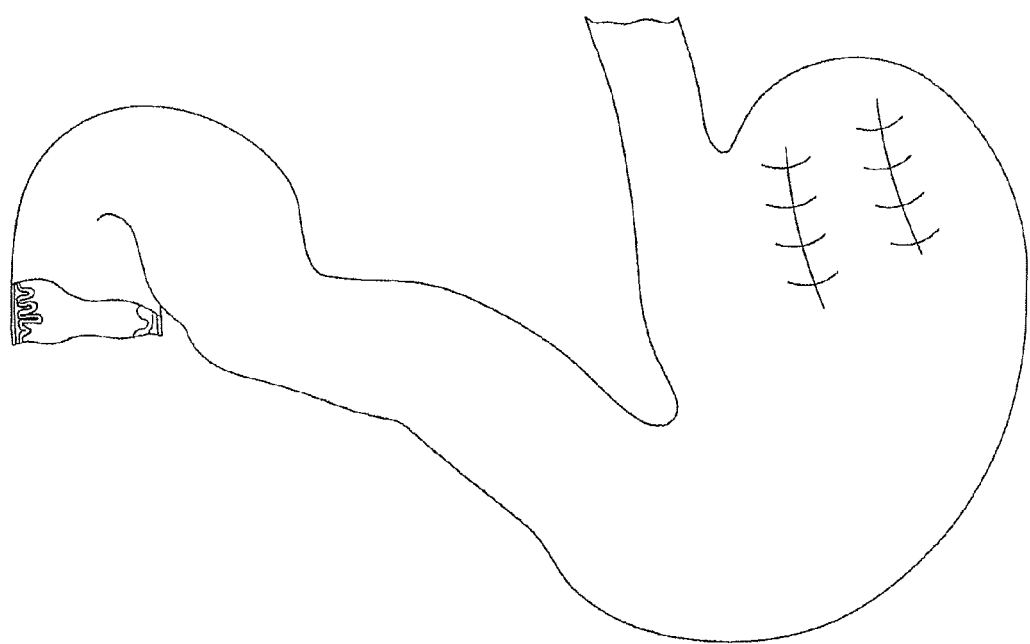
FIG. 35 is an exterior view of a gastric cavity showing folds placed in the fundic region of the cavity reducing gastric capacity and interfering with fundic pressures forcing food into the antral pump.
Figure 36:
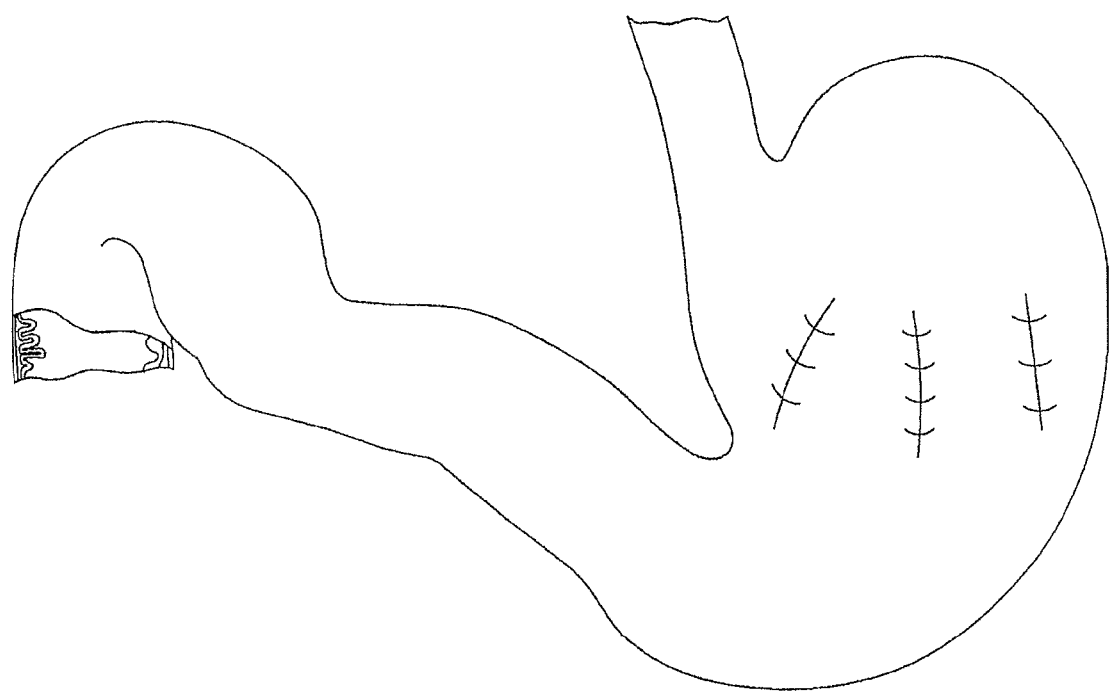
FIG. 36 is an exterior view of a gastric cavity showing folds placed between fundic and distal portions of the cavity reducing volume capacity and altering organ motility.
Figure 37:
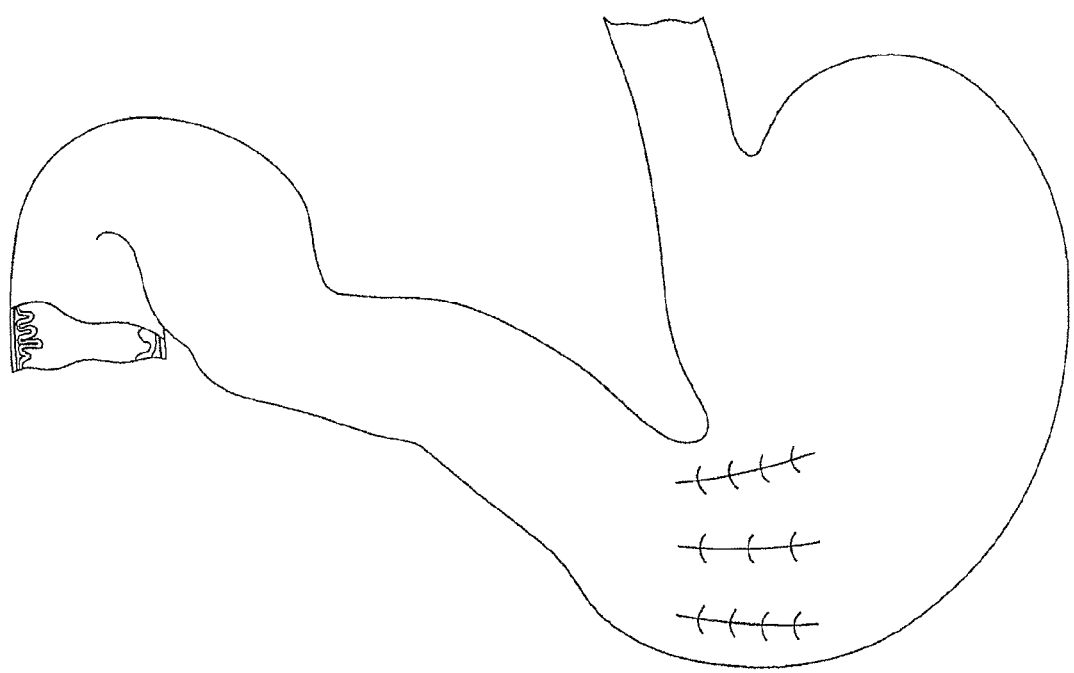
FIG. 37 is an exterior view of a gastric cavity showing a plurality of folds placed in the antrum region of the cavity reducing volume capacity while altering gastric motility and/or introducing an outlet restriction.
Figure 39:
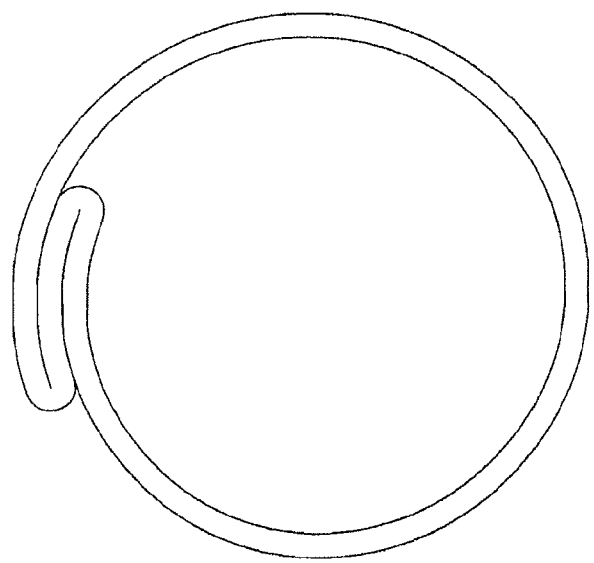
FIGS. 38-43 show several cross-sectional views of different folding patterns.
Figure 38:
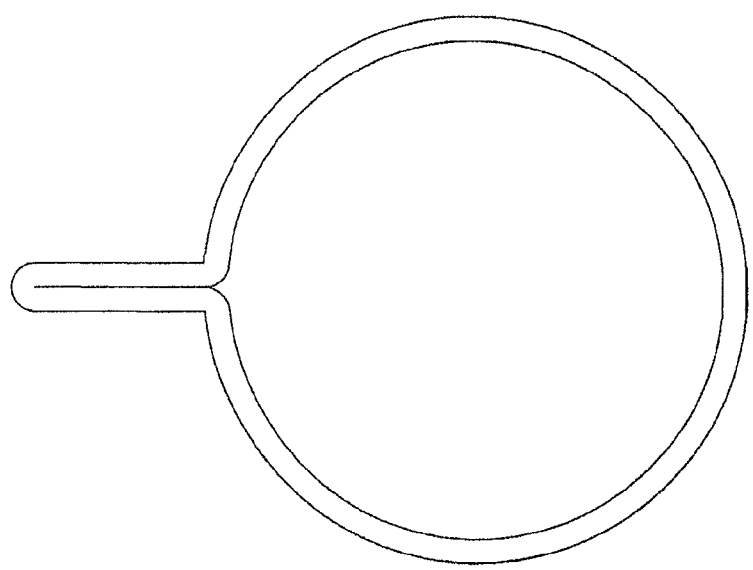
Figure 41:
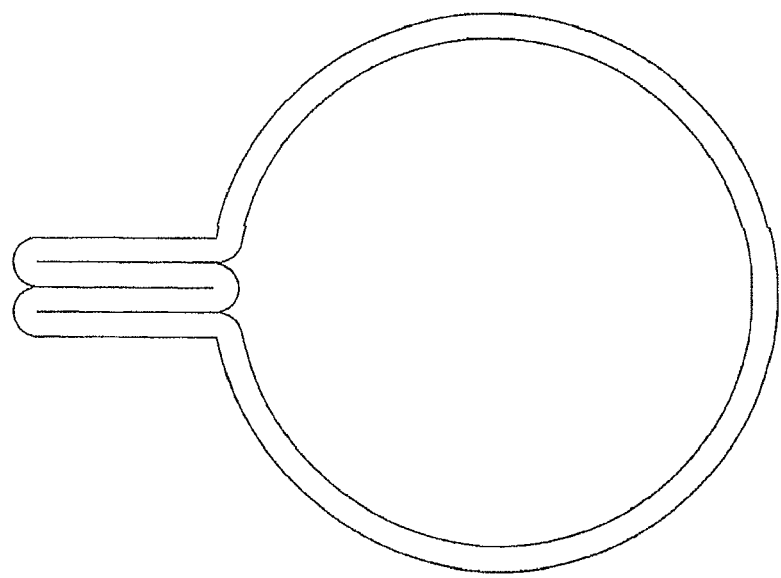
Figure 40:
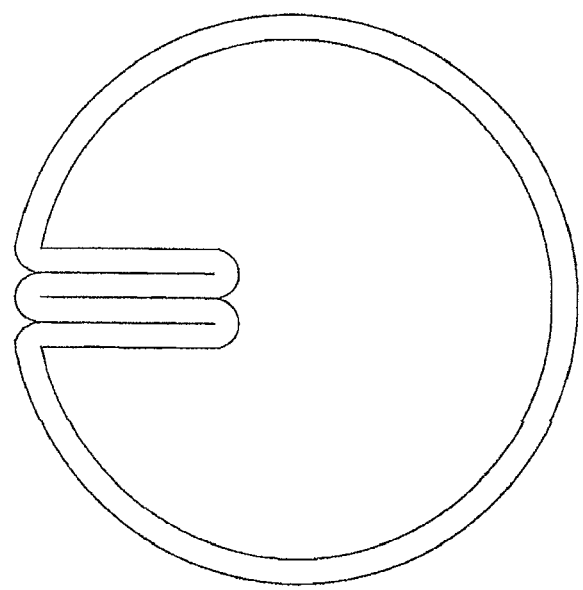
Figure 43:
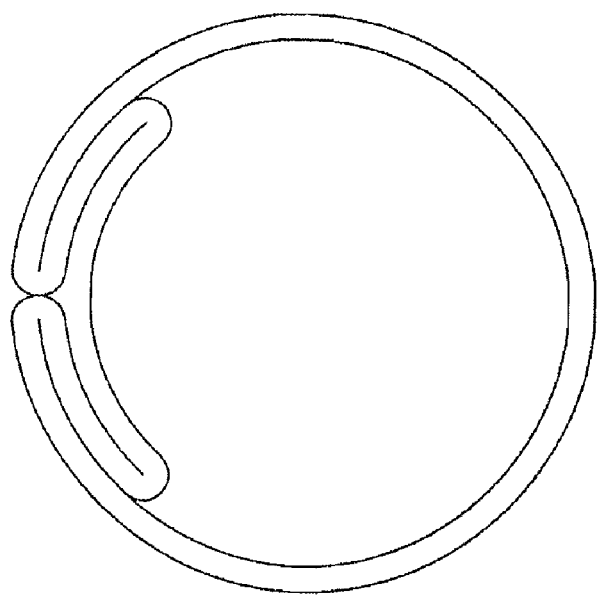
Figure 42:
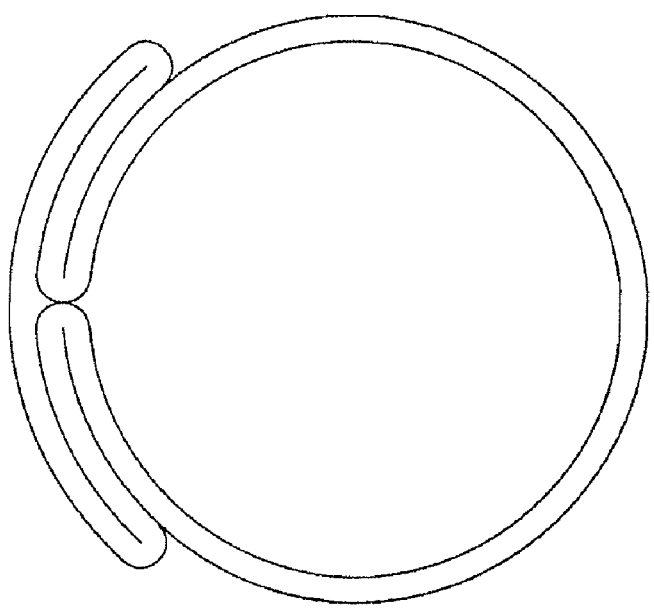

In addition to the embodiments described above, numerous other patterns and locations may be utilized for folding the gastric cavity wall. For example, a fold 172 may be formed in a location between the gastroesophageal junction and the lesser curve of the cavity, as shown in FIG. 34. The fold may be angled towards the lesser curve relative to the gastroesophageal junction to create a reduced-size pouch for food intake and digestion. As discussed above, this type of fold may also create a restriction to food entering the gastric cavity forcing the patient to more thoroughly chew their food. FIG. 35 shows another alternative placement for cavity wall folds. In this example, a pair of folds is placed in the fundic region of the gastric cavity. Locating the folds in the fundic region may lessen distension of the region in response to food intake. The folds may also inhibit the fundic reservoirs ability to produce contractions by either attenuating or baffling the frequency and or intensity of the contractions, to slow digestion and reduce gastric emptying time. FIGS. 36 and 37 show other alternative placements for cavity wall folds. In these examples, a plurality of folds is placed in the lower region of the gastric cavity. In this location, the folds slow gastric motility by interfering with the pumping action within the region. In FIG. 36, the folds are placed within the lower region of the cavity extending angularly between the fundic region and a distal portion of the cavity. In FIG. 37, the folds are placed in the antrum region of the cavity. In addition to the above-described embodiments, numerous other fold placements may be utilized without departing from the scope of the invention. The locations, angles and numbers of cavity wall folds may vary depending upon the particular outcome or treatment sought from the procedure. The effects of these folds may include one or more of the following, all of which serve as aids for the patient to lose weight: reduce gastric capacity; restrict passage of food into the gastric cavity; impair breakdown and movement of food within the gastric cavity; restrict passage of food from the gastric cavity; increase production of satiety producing hormones; etc.

One skilled in the art will quickly realize that a wide range of folds shapes and sizes can be used to induce one or more of the effects described above. FIGS. 38-43 show several examples of alternative fold patterns that may also be created with the present invention.

In the cavity wall folding procedures described above, the suture may be coated with a medicinal or antimicrobial agent to promote healing and treatment or to prevent infection. Methods to prepare a packaged antimicrobial medical device are described in further detail in pending U.S. patent application Ser. No. 11/301,364, filed on Dec. 13, 2005 and U.S. patent application Ser. No. 11/301,365, filed on Dec. 13, 2005; each of which is hereby incorporated herein by reference in its entirety. The suture may also be coated to facilitate passage of the suture through the gastric cavity wall. Exemplary suture coatings and coating methods are described in U.S. Pat. No. 6,712,838, the entire contents of which is hereby incorporated herein by reference. In addition to coating the suture, a medicinal agent may be disposed within the suture anchoring device or applied as a coating on the outside of the anchoring device.

In the above-described embodiments, the gastric cavity may require insufflation through the endoscope to provide satisfactory visualization and maintain adequate internal pressure against the cavity walls. During insufflation of the gastric cavity (either transesophageal insufflation in the case of some open and laparoscopic access approaches or transgastric insufflation in the case of some natural orifice approaches), a portion of the pressurized gas may pass into the jejunum through the pyloric sphincter and insufflate the lumen of the small bowel. This insufflation of the bowel lumen can hinder the gastric wall folding procedure by occluding a laparoscopic view of the peritoneal cavity. Accordingly, for gastric wall folding procedures in which the abdominal cavity is visualized through a laparoscope, it is desirable to either block the passage of the gas into the small bowel, or to vent the bowel. The present invention presents a variety of mechanisms for blocking the passage of gas into the small bowel. These techniques can be achieved laparoscopically, (that is, via a surgically created opening) endoscopically, (that is, via a natural orifice, for example, transorally) or by a hybrid laparoscopic/endoscopic approach.

Figure 44:
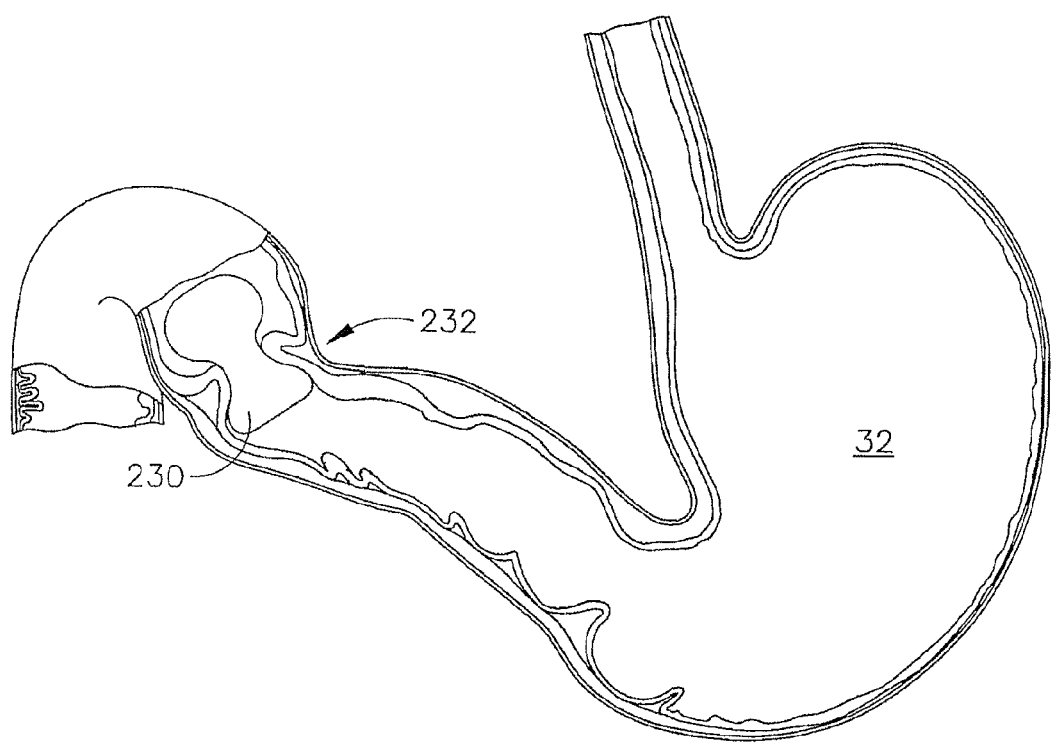
FIG. 44 is a cross-sectional view of a gastric cavity showing a small bowel obstructing member.

FIG. 44 depicts an exemplary technique for blocking the passage of pressurized gas into the small bowel. In this technique, an obstructing member 230 is inserted into the pyloric sphincter 232 transorally (that is, endoscopically). The endoscope 30 may be used to deliver the obstructing member 230 through a working channel within endoscope 30. It may also be delivered to the site by the endoscope 30 in such a way that obstructing member 230 is all or partially external to the endoscope 30. The endoscope 30 may also be used to deliver a guidewire over which obstructing member 230 is simultaneously or subsequently passed. The obstructing member 230 may be inflatable, or made of a conformable material that can be compressed during passage through the endoscope and later expanded to fill the area within the pyloric sphincter. The obstructing member 230 may have a "dog-bone" type shape that enables the member to be more easily retained within the muscular band of the sphincter, preventing migration of obstructing member 230 through the gastrointestinal tract.

Figure 45:
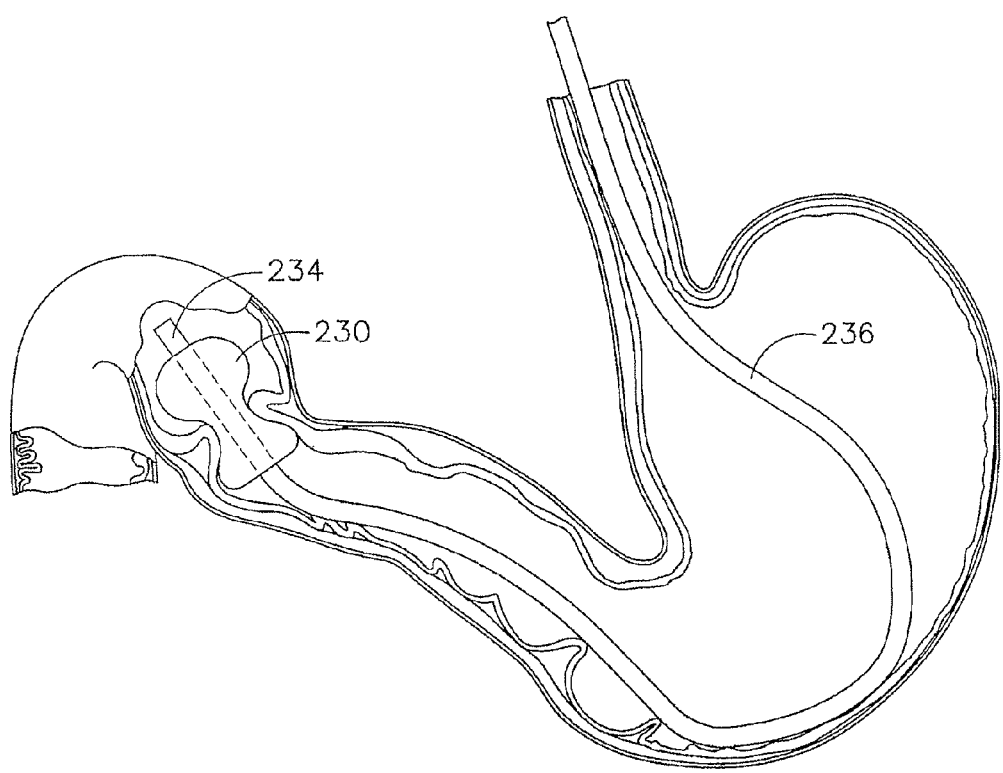
FIG. 45 is a cross-sectional view of a gastric cavity showing a small bowel obstructing member with a venting or evacuation tube.
Figure 46:
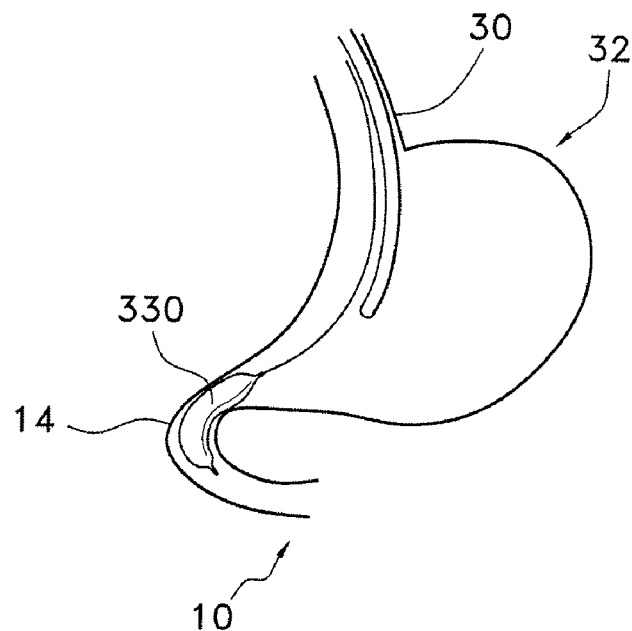
FIG. 46 is a cross sectional view of a gastric cavity showing a small bowel obstructing member positioned within the pyloric sphincter.

FIG. 45 depicts another exemplary technique for reducing bowel insufflation, in which an obstructing member 230 is again placed into pyloric sphincter 232. In this technique, an elongated lumen such as a vent 234 is passed through the obstructing member 230 to suction or release any fluid that may have bypassed the obstructing member 230 into the jejunum. The vent 234 may contain a one-way valve permitting fluid flow in a preferred direction. Fluids from the vent 234 are released outside of the body through a transorally extending tube 236. Vacuum assist may be used to evacuate gas through a tube 236. As with the embodiment shown with reference to FIG. 44, this procedure is also accomplished endoscopically.

With reference to FIGS. 46 to 60, alternate embodiments for preventing insufflation of the small bowel 10 upon insufflation of the gastric cavity 32 are disclosed. In accordance with preferred embodiments as discussed below in greater detail, an obstructing member is inserted into, or an obstruction is created in, the pyloric sphincter 14 from within the gastric cavity 32 to block the passage of gas from the gastric cavity 32 into the small bowel 10. In this manner, the gastric cavity 32 may be insufflated while the gas is prevented from entering the small bowel 10.

As will be discussed below, it is contemplated blockage or obstruction of the pyloric sphincter 14 in a manner separating the small bowel 10 from the gastric cavity 32 may be accomplished in a variety of manners. In accordance with a first embodiment, and with reference to FIG. 46, the obstructing member 330 is a balloon positioned within the pyloric sphincter 14 and inflated to securely position it at a desired location. In accordance with a preferred embodiment, the balloon 330 is a conventional dilatation balloon shaped and dimensioned for positioning within the pyloric sphincter 14. In practice, the dilatation balloon 330 is deployed transorally by running the dilation balloon along the outside of an endoscope 30 and positioning the balloon 330 within the pyloric sphincter 14 while the endoscope 30 remains within the gastric cavity 32 for completion of the procedure.

Figure 47:
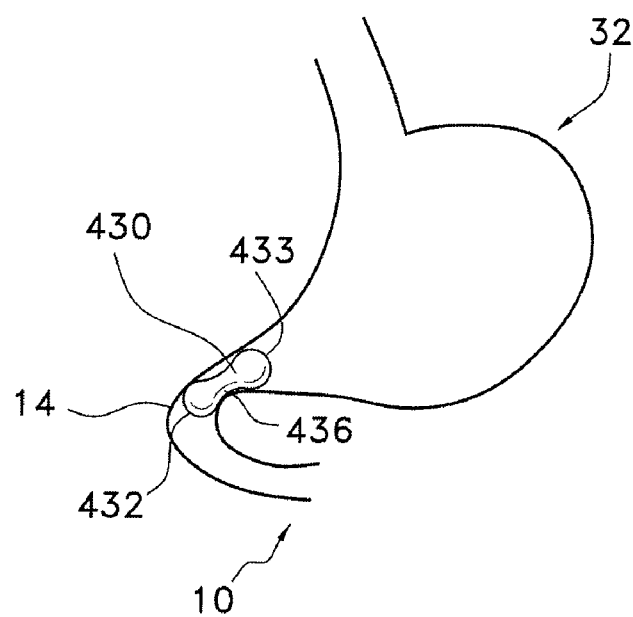
FIG. 47 is an alternate embodiment of an obstructing member positioned within the pyloric sphincter in accordance with the present invention.

Referring to FIG. 47, and in accordance with an alternate embodiment, the obstructing member 430 may also be a drop off balloon which is endoscopically positioned and released at the pyloric sphincter 14 prior to the initiation of the endoscopic procedure. It is contemplated such a balloon 430 may be conformable, and preshaped into a dog bone shaped structure; that is, the balloon 430 includes a leading end 432 and a trailing end 433 with a central section 436 therebetween. The leading end 432 and the trailing end 433 are enlarged relative to the central section 436. The leading end 432 and the trailing end 433 are preferably spherical while the central section 436 is substantially cylindrical. It is contemplated the balloon 430 may also be provided with a barbed section(s) for assisting in retention of the balloon within the pyloric region.

Figure 48:
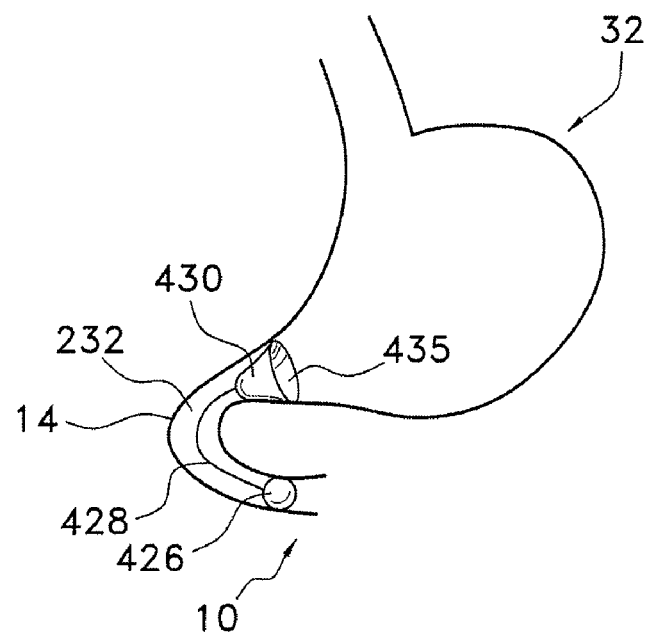
FIG. 48 is a perspective view of yet a further embodiment of an obstructing member positioned within the pyloric sphincter.
Figure 49:
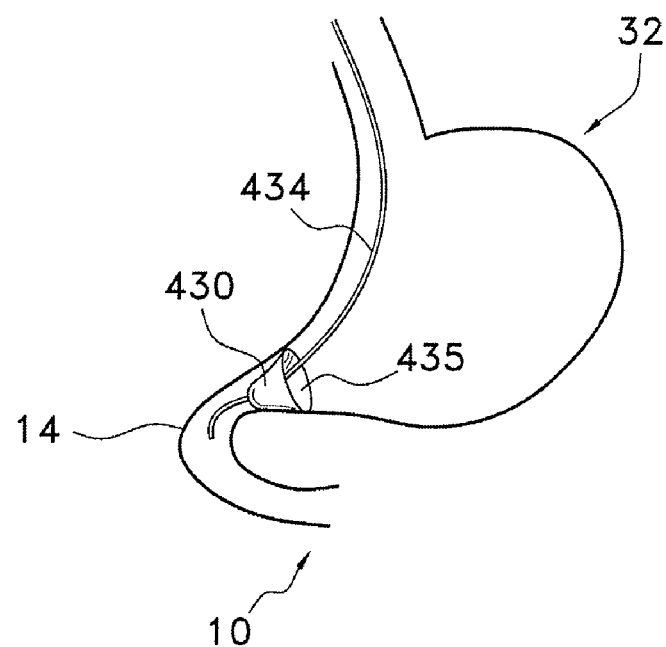
FIG. 49 is a cross sectional view of still a further embodiment of an obstructing member positioned within the pyloric sphincter.

Referring to FIG. 48, and in accordance with yet another embodiment, the obstructing member 430 is shaped like an endoscopically deployed diaphragm, that is, a disc shaped member which is concave along one surface thereof and convex along the opposite surface of the disc shaped member. Although the embodiment shown with reference to FIG. 48 is provided with a balloon 426 extending toward the small bowel 10 from the diaphragm 216 and connected thereto by a tether 428, it is contemplated the diaphragm 430 may be formed with or without the balloon 426 without departing from the spirit of the present invention. The balloon may, however, also be replaced with any object that can be propelled distally by the peristaltic movements of the gastrointestinal track keeping the diaphragm pressed against the pylorus. More particularly, the diaphragm 430 includes a seal member 435 that seats in the stomach side of the pyloric sphincter 14 in a manner creating the desired closure between the gastric cavity 32 and the small bowel 10. The seal member 435 is drawn into contact with the pyloric sphincter as a result of the distal tension applied as the peristaltic motion acts upon the balloon 426 tethered thereto. Referring to FIG. 49, the diaphragm 430 may further include a tube 434 that passes through the center of the seal member 435 (and function as a tether when used in conjunction with a balloon) to vent or suction any gas that may pass through the pyloric sphincter 14 and into the small bowel 10.

Figure 47A:
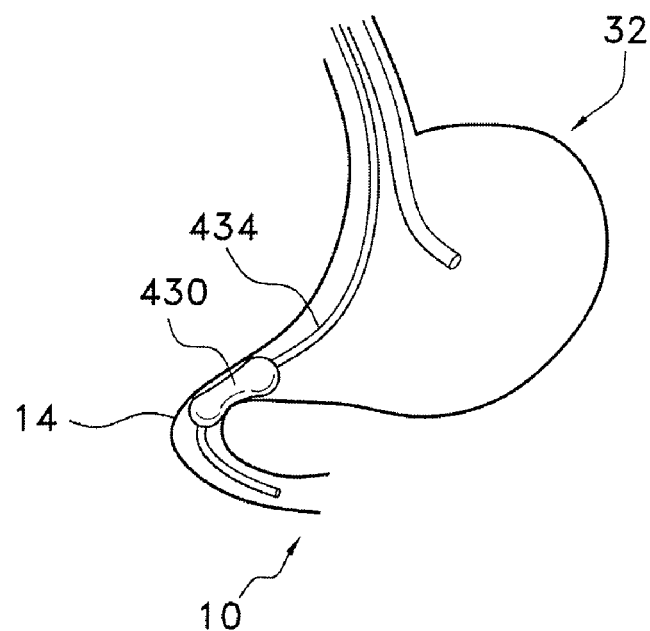
FIG. 47A is an alternate embodiment of an obstructing member positioned within the pyloric sphincter.
Figure 50:
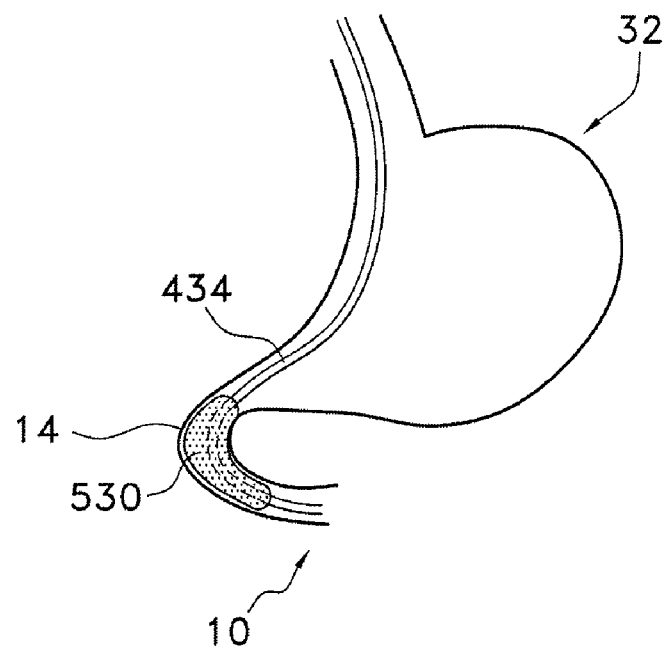
FIG. 50 is a cross sectional view of still another obstructing member positioned within the pyloric sphincter.
Figure 50A:
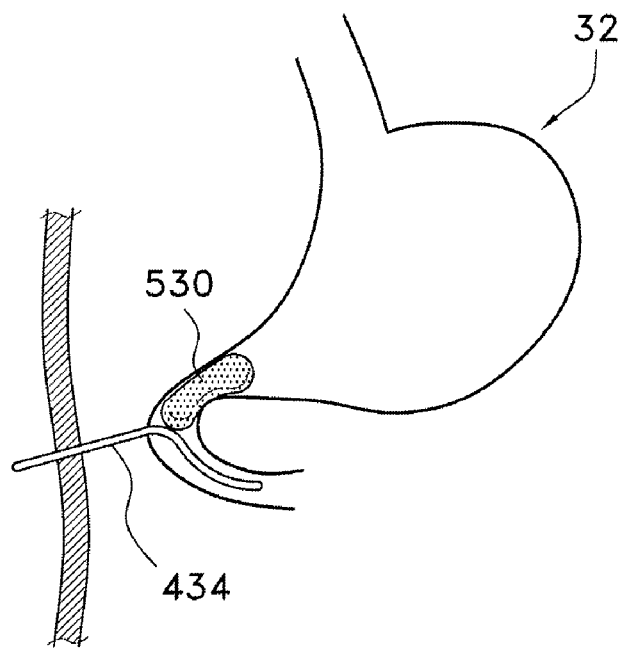
FIG. 50A is a cross sectional view showing a laparoscopically positioned suction tube utilized in conjunction with the obstructing member disclosed with reference to FIG. 50.

Referring to FIG. 50, it is further contemplated the obstructing member 530 may be composed of an endoscopically deployed absorbable material that is hydrophilic, such as, but not limited to, a sponge or other absorbent material. It is also contemplated the material may slowly degrade. As with the embodiment shown with reference to FIG. 48, it is further contemplated a tube 434 may be inserted into and passed through the pyloric sphincter 14 and the obstructing member 530 to vent or suction any gas that passes into the small bowel 10. When such an embodiment is employed it is contemplated the tube 434 may be placed endoscopically (see FIG. 50) or laparoscopically (see FIG. 50A). It is further contemplated vent tubes 434 as described above may similarly be applied to the balloons 430 described above as shown with reference to FIG. 47A.

Figure 51:
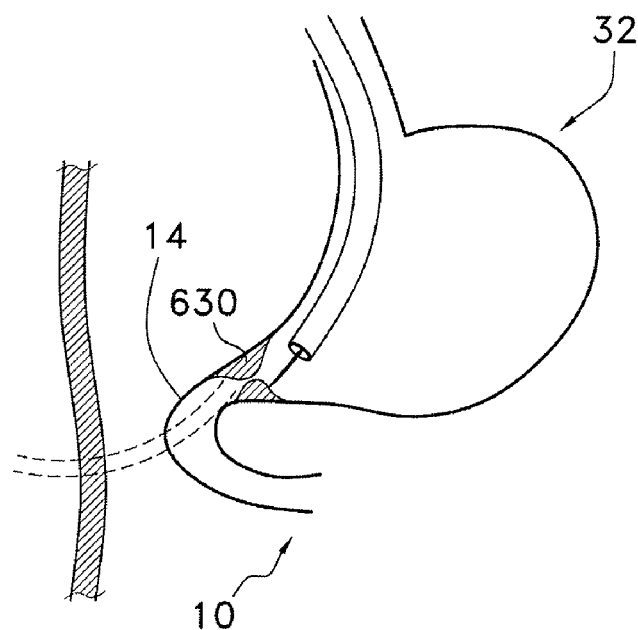
FIG. 51 is a cross sectional view showing yet another obstructing member positioned within the pyloric sphincter.

In accordance with an alternate embodiment, and with reference to FIG. 51, the pyloric sphincter 14 may be blocked through the injection, endoscopically or laparoscopically (shown in dotted lines), of fluid 630 into the pyloric sphincter 14 to occlude the opening and thereby create an obstructing member. It is contemplated the fluid would be an absorbable material, that is, saline, nitrogen gas, $CO_2$ gas, etc., such that it is readily evacuated from the pyloric sphincter 14 upon completion of the procedure.

Figure 52:
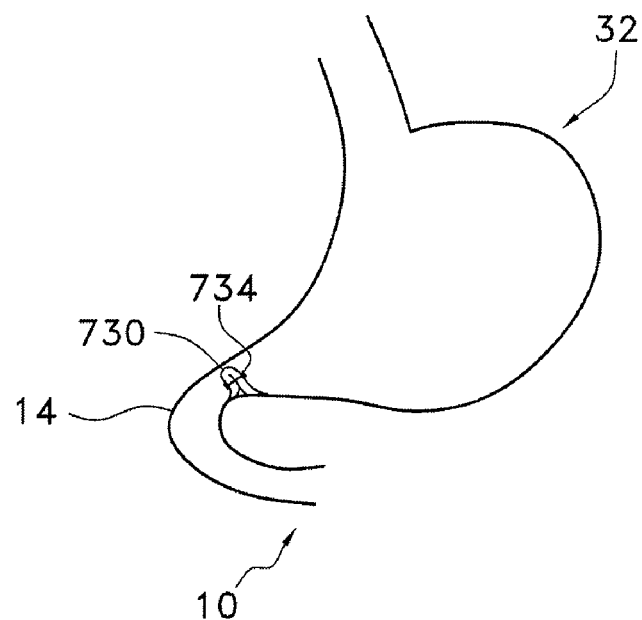
FIG. 52 is a cross sectional view showing a fold utilized as an obstructing member within the pyloric sphincter.
Figure 53:
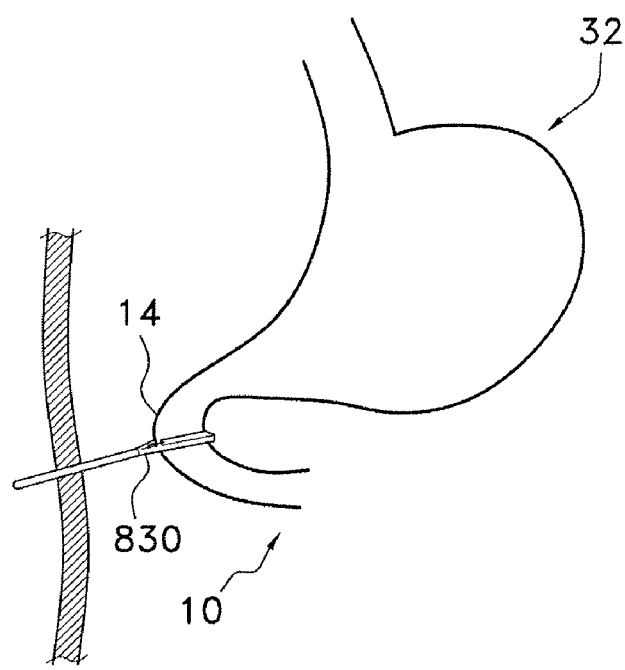
FIG. 53 is a cross sectional view showing laparoscopic attachment of a clamp member in the formation of an obstructing member within the pyloric sphincter.
Figure 54:
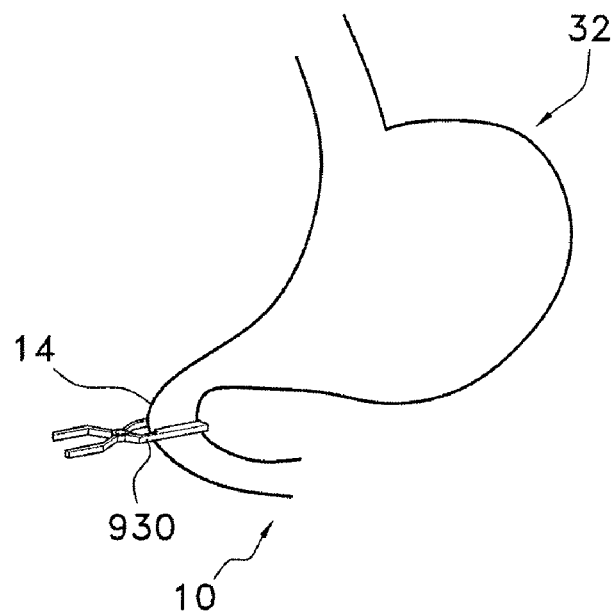
FIG. 54 is a cross sectional view of a yet another clamp member utilized in the creation of an obstructing member along the pyloric sphincter.
Figure 55:
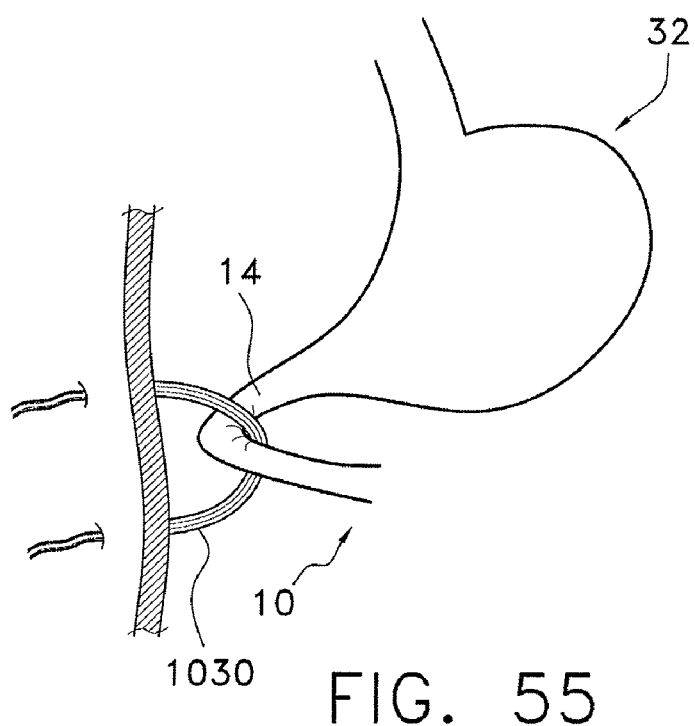
FIG. 55 shows yet another embodiment for laparoscopic creation of an obstructing member within the pyloric sphincter.
Figure 56:
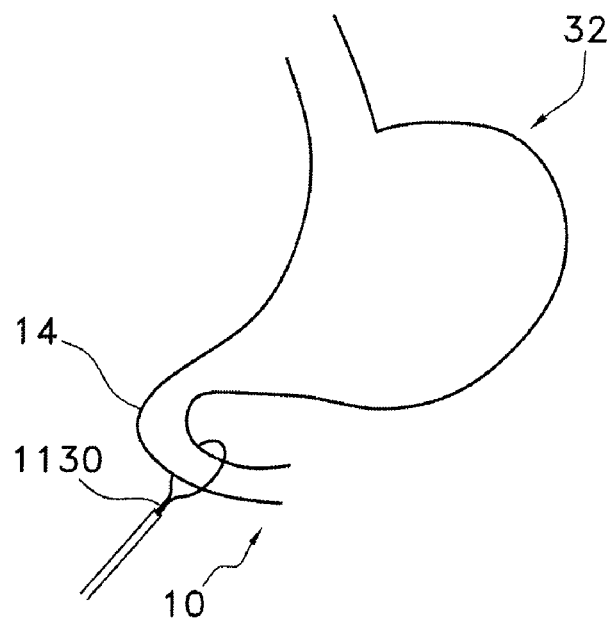
FIG. 56 shows a further embodiment of a laparoscopically positioned obstructing member along the pyloric sphincter.

In addition, and with reference to FIG. 52, the pyloric sphincter 14 may be blocked by the endoscopic or laparoscopic formation of a fold 730 in the tissue of the pyloric sphincter 14. The fold 730 would be constructed to effectively block the passage of gas from the gastric cavity 32 and into the small bowel 10. In accordance with a preferred embodiment, an internal fold 730 is created like an internal plication formed with an endoscopic device like a T-tag applier 734 or internal suturing device. It is also possible to create an external fold within the pyloric region. The external fold is preferably created by placing a sling around the duodenum in a manner creating a fold of tissue to seal the pyloric region and separate the small bowel from the stomach.

Figure 57:
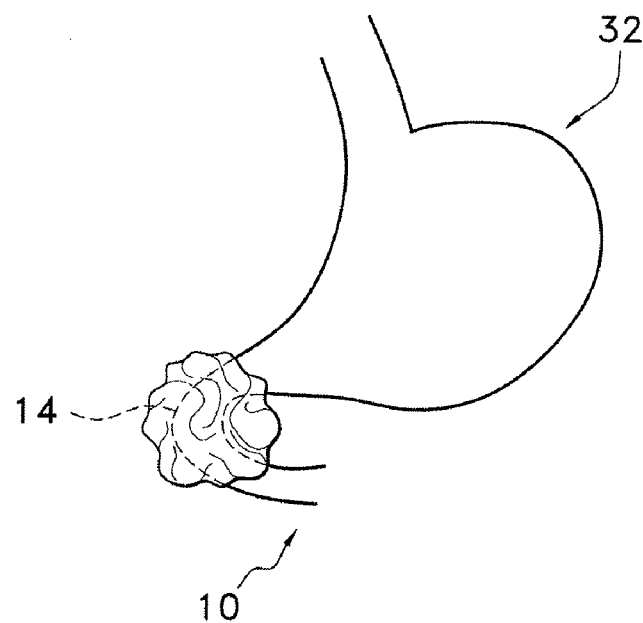
FIG. 57 shows yet another embodiment of an obstructing member positioned along the pyloric sphincter.

In addition to blocking the pyloric region through either the application of an artificial obstructing member or the formation of a natural obstructing member, blockage of the pyloric sphincter 14 may be accomplished through the utilization of a laparoscopically applied external clamp for compression of the pyloric sphincter 14 as shown with reference to FIGS. 53-57. The external clamp applies a compression load on the tissue to seal the small bowel 10 from the gas being applied to the gastric cavity 32. The clamp is preferably provided with the ability to limit the amount of force on the tissue so that there is no tissue damage (such as weighed mass, force limiting clamp, etc.). In accordance with various embodiments contemplated in accordance with the present invention, the clamp may take the form of an atraumatic clamp 830 (FIG. 53), a bulldog clamp 930 (FIG. 54), an externally applied suture loop 1030 secured about the pyloric sphincter 14 which draws the pyloric sphincter 14 into compression toward the external skin (FIG. 55), a continuous/interrupted loop or snare 1130 (FIG. 56) or a weighted sack (or mass) 1230 (FIG. 57).

Figure 58:
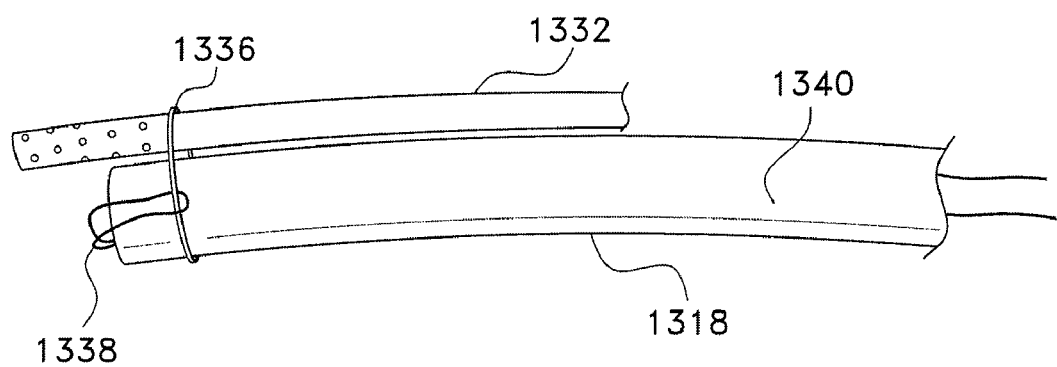
FIG. 58 shows an instrument for the creation of an obstructing member within the pyloric sphincter.

In accordance with an alternate embodiment and as briefly discussed above in conjunction with various embodiments, it is possible to vent gases from within the pyloric sphincter 14 to prevent passage thereof to the small bowel while also substantially blocking the stomach from the small bowel. Referring to FIG. 58, an instrument for the endoscopic deployment of a vent tube 1332 is disclosed. A rubber band 1336 is placed around the endoscope 1318 and a vent tube 1332. A suture 1338 is attached to the rubber band 1336. The suture 1338 extends into the working channel 1340 of the endoscope 30 and, therefore, may be actuated by the medical practitioner during the procedure.

Once the vent tube 1332 is in a desired location beyond the pyloric sphincter 14, the suture 1338 is pulled through the working channel 1340 of the endoscope 1318. The rubber band 1336 is stretched out and breaks off and is pulled inside the working channel 1340 of the endoscope 1318 for retrieval by the medical practitioner performing the procedure. This releases the vent tube 1332 and the endoscope 1318 is retracted leaving the vent tube 1332 in a desired position beyond the pyloric sphincter 14.

Figure 59:
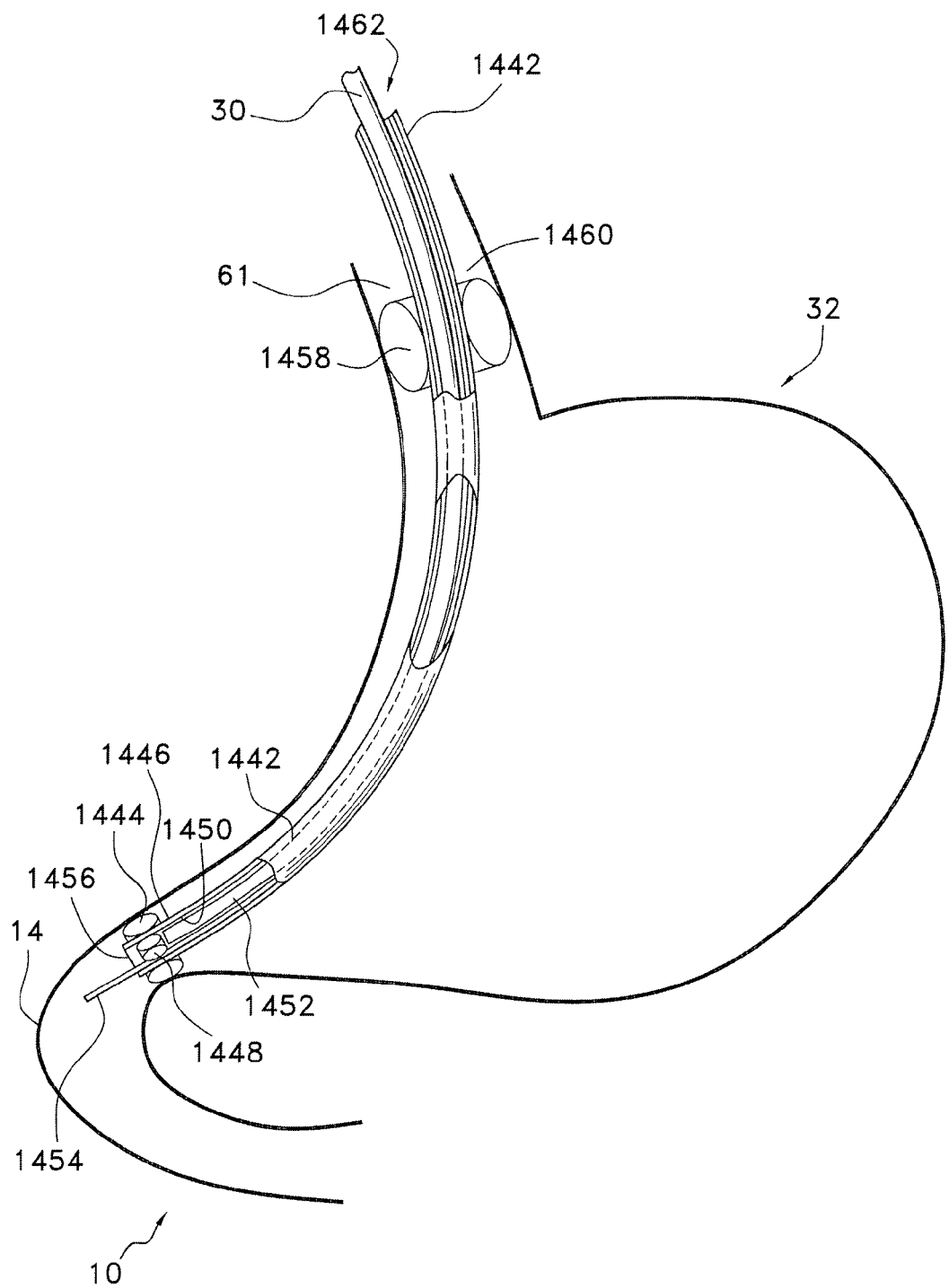
FIG. 59 shows yet another embodiment of an instrument utilized in creating an obstruction within the pyloric sphincter.

In accordance with another embodiment, and with reference to FIG. 59, another mechanism for endoscopic deployment of an obstructing member and vent tube is disclosed. The obstructing member 1430 includes a specialized over tube 1442 that is inserted over the endoscope 30. The endoscope 30 and over tube 1442 together are placed transorally into the esophagus and into the gastric cavity 32. From there, the distal end 1446 of the over tube 1442 is moved to a position within pyloric sphincter 14.

The over tube 1442 is provided with an external balloon 1444 at its distal end 1446. As such, and once the over tube 1442 is positioned fully into the pyloric sphincter 14 with the uninflated external balloon 1444 within the pyloric sphincter 14, the external balloon 1444 is inflated in manner holding the distal end 1446 of the over tube 1442 securely inside the pyloric sphincter 14.

The endoscope 30, which is positioned within the over tube 1442, is then withdrawn a few inches allowing an internal balloon 1448 formed along the inner wall 1450 of the over tube 1442 adjacent to the distal end 1455 of the over tube 1442 to be inflated. The internal balloon 1448 is formed along the internal wall 1450 of the lumen 1452 of the over tube 1442 and inflation of the internal balloon 1448, when combined with inflation of the external balloon 1444 as discussed below, completely blocks the airflow and fluid flow through the distal end 1446 of the over tube 1442.

A drain/vent 1454 integrally found within the over tube 1442 is then extended out of the distal tip 1456 of the over tube 1442 to evacuate/suction the gas from the small bowel 10 that has been created from the endoscope 30. An external balloon 1458 is then inflated on the outside of the over tube 1442 along a central portion of the over tube 1442 in the gastroesophageal junction or gastrointestinal junction 61. This totally blocks the airflow around the endoscope 30 such that air used to insufflate the gastric cavity 32 cannot escape out of the esophagus.

An additional seal may be added to properly seal around the endoscope while allowing movement of the endoscope. This system also allows the interior of the stomach to be attached to suction/insufflation. The pressure and volume of the air supply inside the stomach can be constantly monitored during the procedure. A pre-surgical volume, a post-surgical volume and real-time volume may be taken during the procedure to ensure the stomach is reduced to the desired percentage. A computerized testing system may be used to automate these measurements.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, or steam.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

The invention claimed is:

1. A method for laparoscopically preventing insufflation of a small bowel during gastric procedures, comprising: applying an obstruction member at a pyloric sphincter to block passage of gas from a gastric cavity into the small bowel; insufflating the gastric cavity; and further including the step of inserting a tube into and through the pyloric sphincter, and venting or suctioning any gas that passes into the small bowel.

2. The method according to claim 1, wherein the tube is inserted laparoscopically.

3. The method according to claim 1, wherein the obstruction member consists of a fluid injected into the pyloric sphincter.

4. The method according to claim 3, wherein the fluid is an absorbable material.

5. The method according to claim 1, wherein the step of applying an obstruction member includes forming a fold in tissue of the pyloric sphincter effectively blocking passage of gas from the gastric cavity into the small bowel.

6. The method according to claim 1, wherein the step of applying an obstruction member includes applying an external clamp to the pyloric sphincter, the clamp applying a compression load on tissue to seal the small bowel from gas being applied to gastric cavity.

* * * * *